US007253187B2

United States Patent

(12) United States Patent
Cao et al.

(10) Patent No.: US 7,253,187 B2
(45) Date of Patent: Aug. 7, 2007

(54) HETEROCYCLIC INHIBITORS OF ERK2 AND USES THEREOF

(75) Inventors: Jingrong Cao, Newton, MA (US); Jeremy Green, Burlington, MA (US); Michael Hale, Bedford, MA (US); Francois Maltais, Tewksbury, MA (US); Judy Straub, Cambridge, MA (US); Qing Tang, Cambridge, MA (US); Alex Aronov, Watertown, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 184 days.

(21) Appl. No.: 10/770,814

(22) Filed: Feb. 3, 2004

(65) Prior Publication Data

US 2004/0229875 A1 Nov. 18, 2004

Related U.S. Application Data

(62) Division of application No. 10/071,699, filed on Feb. 8, 2002, now Pat. No. 6,743,791.

(60) Provisional application No. 60/328,768, filed on Oct. 12, 2001, provisional application No. 60/267,818, filed on Feb. 9, 2001.

(51) Int. Cl.
*C07D 401/04* (2006.01)
*A61K 31/4427* (2006.01)

(52) U.S. Cl. ...................... 514/336; 514/340; 514/341; 514/342; 514/343; 546/270.4; 546/271.1; 546/271.4; 546/272.1; 546/272.4; 546/274.1; 546/275.4; 546/279.1; 546/280.4; 546/284.7

(58) Field of Classification Search ............. 546/270.4, 546/271.1, 271.4, 272.1, 272.4, 274.1, 275.4, 546/279.1, 280.4, 284.7; 514/336, 340, 341, 514/342, 343
See application file for complete search history.

(56) References Cited

U.S. PATENT DOCUMENTS 5,792,778 A 8/1998 de Laszlo et al.

FOREIGN PATENT DOCUMENTS

| | | |
|---|---|---|
| WO | WO 95/13067 | 5/1995 |
| WO | WO 97/05878 | 2/1997 |
| WO | WO 97/16442 | 5/1997 |
| WO | WO 99/32121 | 7/1999 |
| WO | WO 99/58523 | 11/1999 |
| WO | WO 00/26209 | 5/2000 |
| WO | WO 01/74811 | * 10/2001 |

OTHER PUBLICATIONS

Damasio, Alzheimer's Disease and Related Dementias, Cecil Textbook of Medicine, 20th Edition, vol. 2, pp. 1992-6, 1996.*

Rogers et al., PubMed Abstract (J Cell Biol. 157(2):219-29) Apr. 2002.*

Tanaka et al., PubMed Abstract (Cell. 108(3):317-29) Feb. 2000.*

Hardt et al., Glycogen Synthase Kinase -3beta: A Novel Regulator of Cardiac Hypertrophy and Development, Circulation Research, 90:1055-1063, 2002.*

* cited by examiner

*Primary Examiner*—Deepak Rao
(74) *Attorney, Agent, or Firm*—Daniel A. Pearson

(57) ABSTRACT

Described herein are compounds that are useful as protein kinase inhibitors having the formula:

I

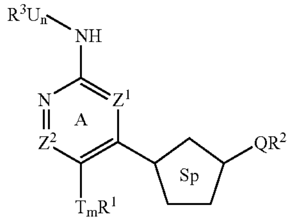

wherein $Z^1$ and $Z^2$ are each independently nitrogen or CH and Ring A, $T_mR^1$, $QR^2$, $U_nR^3$, and Sp are as described in the specification. The compounds are especially useful as inhibitors of ERK2 and for treating diseases in mammals that are alleviated by a protein kinase inhibitor, particularly diseases such as cancer, inflammatory disorders, restenosis, diabetes, and cardiovascular disease.

25 Claims, No Drawings

HETEROCYCLIC INHIBITORS OF ERK2 AND USES THEREOF

CROSS REFERENCE TO RELATED APPLICATIONS

This application is a divisional of U.S. patent application Ser. No. 10/071,699, filed Feb. 8, 2002 now U.S. Pat. No. 6,743,791, which claims priority to U.S. Provisional Application Ser. No. 60/267,818 filed Feb. 9, 2001 and U.S. Provisional Application Ser. No. 60/328,768 filed Oct. 12, 2001, the entirety of which is incorporated herein by reference.

FIELD OF THE INVENTION

The present invention is in the field of medicinal chemistry and relates to pyrazole compounds that are protein kinase inhibitors, especially inhibitors of ERK, compositions containing such compounds and methods of use. The compounds are useful for treating cancer and other diseases that are alleviated by protein kinase inhibitors.

BACKGROUND OF THE INVENTION

Mammalian mitogen-activated protein (MAP)1 kinases are serine/threonine kinases that mediate intracellular signal transduction pathways (Cobb and Goldsmith, 1995, *J Biol. Chem*., 270, 14843; Davis, 1995, *Mol. Reprod. Dev*. 42, 459). Members of the MAP kinase family share sequence similarity and conserved structural domains, and include the ERK2 (extracellular signal regulated kinase), JNK (Jun N-terminal kinase), and p38 kinases. JNKs and p38 kinases are activated in response to the pro-inflammatory cytokines TNF-alpha and interleukin-1, and by cellular stress such as heat shock, hyperosmolarity, ultraviolet radiation, lipopolysaccharides and inhibitors of protein synthesis (Derijard et al., 1994, *Cell* 76, 1025; Han et al., 1994, *Science* 265, 808; Raingeaud et al., 1995, *J Biol. Chem*. 270, 7420; Shapiro and Dinarello, 1995, *Proc. Natl. Acad. Sci. USA* 92, 12230). In contrast, ERKs are activated by mitogens and growth factors (Bokemeyer et al. 1996, *Kidney Int*. 49, 1187).

ERK2 is a widely distributed protein kinase that achieves maximum activity when both Thr183 and Tyr185 are phosphorylated by the upstream MAP kinase kinase, MEK1 (Anderson et al., 1990, *Nature* 343, 651; Crews et al., 1992, *Science* 258, 478). Upon activation, ERK2 phosphorylates many regulatory proteins, including the protein kinases Rsk90 (Bjorbaek et al., 1995, *J. Biol. Chem*. 270, 18848) and MAPKAP2 (Rouse et al., 1994, *Cell* 78, 1027), and transcription factors such as ATF2 (Raingeaud et al., 1996, *Mol. Cell Biol*. 16, 1247), Elk-1 (Raingeaud et al. 1996), c-Fos (Chen et al., 1993 *Proc. Natl. Acad. Sci. USA* 90, 10952), and c-Myc (Oliver et al., 1995, *Proc. Soc. Exp. Biol. Med*. 210, 162). ERK2 is also a downstream target of the Ras/Raf dependent pathways (Moodie et al., 1993, *Science* 260, 1658) and may help relay the signals from these potentially oncogenic proteins. ERK2 has been shown to play a role in the negative growth control of breast cancer cells (Frey and Mulder, 1997, *Cancer Res*. 57, 628) and hyperexpression of ERK2 in human breast cancer has been reported (Sivaraman et al., 1997, *J Clin. Invest*. 99, 1478). Activated ERK2 has also been implicated in the proliferation of endothelin-stimulated airway smooth muscle cells, suggesting a role for this kinase in asthma (Whelchel et al., 1997, *Am. J. Respir. Cell Mol. Biol*. 16, 589).

Aurora-2 is a serine/threonine protein kinase that has been implicated in human cancer, such as colon, breast and other solid tumors. This kinase is believed to be involved in protein phosphorylation events that regulate the cell cycle. Specifically, Aurora-2-may play a role in controlling the accurate segregation of chromosomes during mitosis. Misregulation of the cell cycle can lead to cellular proliferation and other abnormalities. In human colon cancer tissue, the aurora-2 protein has been found to be overexpressed. See Bischoff et al., *EMBO J*., 1998, 17, 3052–3065; Schumacher et al., *J. Cell Biol*., 1998, 143, 1635–1646; Kimura et al., *J. Biol. Chem*., 1997, 272, 13766–13771.

Glycogen synthase kinase-3 (GSK-3) is a serine/threonine protein kinase comprised of α and β isoforms that are each encoded by distinct genes [Coghlan et al., *Chemistry & Biology*, 7, 793–803 (2000); Kim and Kimmel, *Curr. Opinion Genetics Dev*., 10, 508–514 (2000)]. GSK-3 has been implicated in various diseases including diabetes, Alzheimer's disease, CNS disorders such as manic depressive disorder and neurodegenerative diseases, and cardiomyocete hypertrophy [WO 99/65897; WO 00/38675; and Haq et al., *J. Cell Biol*. (2000) 151, 117]. These diseases may be caused by, or result in, the abnormal operation of certain cell signaling pathways in which GSK-3 plays a role. GSK-3 has been found to phosphorylate and modulate the activity of a number of regulatory proteins. These proteins include glycogen synthase which is the rate limiting enzyme necessary for glycogen synthesis, the microtubule associated protein Tau, the gene transcription factor β-catenin, the translation initiation factor e1F2B, as well as ATP citrate lyase, axin, heat shock factor-1, c-Jun, c-Myc, c-Myb, CREB, and CEPBα. These diverse protein targets implicate GSK-3 in many aspects of cellular metabolism, proliferation, differentiation and development.

In a GSK-3 mediated pathway that is relevant for the treatment of type II diabetes, insulin-induced signaling leads to cellular glucose uptake and glycogen synthesis. Along this pathway, GSK-3 is a negative regulator of the insulin-induced signal. Normally, the presence of insulin causes inhibition of GSK-3 mediated phosphorylation and deactivation of glycogen synthase. The inhibition of GSK-3 leads to increased glycogen synthesis and glucose uptake [Klein et al., *PNAS*, 93, 8455–9 (1996); Cross et al., *Biochem. J.,* 303, 21–26 (1994); Cohen, *Biochem. Soc. Trans.,* 21, 555–567 (1993); Massillon et al., *Biochem J.* 299, 123–128 (1994)]. However, in a diabetic patient where the insulin response is impaired, glycogen synthesis and glucose uptake fail to increase despite the presence of relatively high blood levels of insulin. This leads to abnormally high blood levels of glucose with acute and long term effects that may ultimately result in cardiovascular disease, renal failure and blindness. In such patients, the normal insulin-induced inhibition of GSK-3 fails to occur. It has also been reported that in patients with type II diabetes, GSK-3 is overexpressed [WO 00/38675]. Therapeutic inhibitors of GSK-3 therefore are considered to be useful for treating diabetic patients suffering from an impaired response to insulin.

GSK-3 activity has also been associated with Alzheimer's disease. This disease is characterized by the well-known β-amyloid peptide and the formation of intracellular neurofibrillary tangles. The neurofibrillary tangles contain hyperphosphorylated Tau protein where Tau is phosphorylated on abnormal sites. GSK-3 has been shown to phosphorylate these abnormal sites in cell and animal models. Furthermore, inhibition of GSK-3 has been shown to prevent hyperphosphorylation of Tau in cells [Lovestone et al., *Current Biology* 4, 1077–86 (1994); Brownlees et al., *Neu-*

*roreport* 8, 3251–55 (1997)]. Therefore, it is believed that GSK-3 activity may promote generation of the neurofibrillary tangles and the progression of Alzheimer's disease.

Another substrate of GSK-3 is β-catenin which is degradated after phosphorylation by GSK-3. Reduced levels of β-catenin have been reported in schizophrenic patients and have also been associated with other diseases related to increase in neuronal cell death [Zhong et al., *Nature*, 395, 698–702 (1998); Takashima et al., *PNAS*, 90, 7789–93 (1993); Pei et al., *J. Neuropathol. Exp*, 56, 70–78 (1997)].

As a result of the biological importance of GSK-3, there is current interest in therapeutically effective GSK-3 inhibitors. Small molecules that inhibit GSK-3 have recently been reported [WO 99/65897 (Chiron) and WO 00/38675 (SmithKline Beecham)].

Aryl substituted pyrroles are known in the literature. In particular, tri-aryl pyrroles (U.S. Pat. No. 5,837,719) have been described as having glucagon antagonist activity. 1,5-Diarylpyrazoles have been described as p38 inhibitors (WO 9958523).

There is a high unmet medical need to develop new therapeutic treatments that are useful in treating the various conditions associated with ERK2 activation. For many of these conditions the currently available treatment options are inadequate.

Accordingly, there is great interest in new and effective inhibitors of protein kinase, including ERK2 inhibitors, that are useful in treating various conditions associated with protein kinase activation.

DESCRIPTION OF THE INVENTION

It has now been found that compounds of this invention and compositions thereof are effective as protein kinase inhibitors, especially as inhibitors of ERK2. These compounds have the general formula I:

I

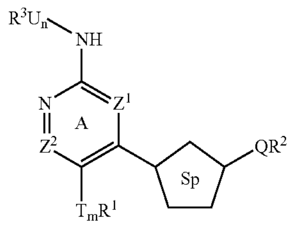

or a pharmaceutically acceptable derivative thereof, wherein:,

Sp is a spacer group comprising a 5-membered heteroaromatic ring, wherein Ring A and $QR^2$ are attached to Sp at non-adjacent positions; and wherein Sp has up to two $R^6$ substituents, provided that two substitutable carbon ring atoms in Sp are not simultaneously substituted by $R^6$;

$Z^1$ and $Z^2$ are each independently selected from N or CH;

T and Q are each an independently selected linker group;

U is selected from $—NR^7—$, $—NR^7CO—$, $—NR^7CONR^7—$, $—NR^7CO_2—$, —O—, $—CONR^7—$, —CO—, $—CO_2—$, —OC(O)—, $—NR^7SO_2—$, $—SO_2NR^7—$, $—NR^7SO_2NR^7—$, or $—SO_2—$;

m and n are each independently selected from zero or one;

$R^1$ is selected from hydrogen, CN, halogen, R, $N(R^7)_2$, OR, or OH;

$R^2$ is selected from $—(CH_2)_yR^5$, $—(CH_2)_yCH(R^5)_2$, $—(CH_2)_yCH(R^8)CH(R^5)_2$, $—N(R^4)_2$, or $—NR^4(CH_2)_yN(R^4)_2$;

y is 0–6;

$R^3$ is selected from $R^7$, R, $—(CH_2)_yCH(R^8)R$, CN, $—(CH_2)_yCH(R^8)CH(R^5)_2$, or $—(CH_2)_yCH(R^8)N(R^4)_2$;

each R is independently selected from an optionally substituted group selected from $C_{1-6}$ aliphatic, $C_{6-10}$ aryl, a heteroaryl ring having 5–10 ring atoms, or a heterocyclyl ring having 3–10 ring atoms;

each $R^4$ is independently selected from R, $R^7$, $—COR^7$, $—CO_2R$, $—CON(R^7)_2$, $—SO_2R^7$, $—(CH_2)_yR^5$, or $—(CH_2)_yCH(R^5)_2$;

each $R^5$ is independently selected from R, OR, $CO_2R$, $(CH_2)_yN(R^7)_2$, $N(R^7)_2$, $OR^7$, $SR^7$, $NR^7COR^7$, $NR^7CON(R^7)_2$; $CON(R^7)_2$, $SO_2R^7$, $NR^7SO_2R^7$, $COR^7$, CN, or $SO_2N(R^7)_2$;

each $R^6$ is independently selected from $R^7$, F, Cl, $(CH_2)_yN(R^7)_2$, $N(R^7)_2$, $OR^7$, $SR^7$, $NR^7COR^7$, $NR^7CON(R^7)_2$, $CON(R^7)_2$, $SO_2R^7$, $NR^7SO_2R^7$, $COR^7$, CN, or $SO_2N(R^7)_2$;

each $R^7$ is independently selected from hydrogen or an optionally substituted $C_{1-6}$ aliphatic group, or two $R^7$ on the same nitrogen are taken together with the nitrogen to form a 5–8 membered heterocyclyl or heteroaryl ring;

$R^8$ is selected from R, $(CH_2)_wOR^7$, $(CH_2)_wN(R^4)_2$, or $(CH_2)_wSR^7$; and each w is independently selected from 0–4.

As used herein, the following definitions shall apply unless otherwise indicated. The phrase "optionally substituted" is used interchangeably with the phrase "substituted or unsubstituted" or with the term "(un)substituted." Unless otherwise indicated, an optionally'substituted group may have a substituent at each substitutable position of the group, and each substitution is independent of the other.

The term "aliphatic" or "aliphatic group" as used herein means a straight-chain or branched $C_1$–$C_{12}$ hydrocarbon chain that is completely saturated or that contains one or more units of unsaturation, or a monocyclic $C_3$–$C_8$ hydrocarbon or bicyclic $C_8$–$C_{12}$ hydrocarbon that is completely saturated or that contains one or more units of unsaturation, but which is not aromatic (also referred to herein as "carbocycle" or "cycloalkyl"), that has a single point of attachment to the rest of the molecule wherein any individual ring in said bicyclic ring system has 3–7 members. For example, suitable aliphatic groups include, but are not limited to, linear or branched or alkyl, alkenyl, alkynyl groups and hybrids thereof such as (cycloalkyl)alkyl, (cycloalkenyl) alkyl or (cycloalkyl)alkenyl.

The terms "alkyl", "alkoxy", "hydroxyalkyl", "alkoxyalkyl", and "alkoxycarbonyl", used alone or as part of a larger moiety includes both straight and branched chains containing one to twelve carbon atoms. The terms "alkenyl" and "alkynyl" used alone or as part of a larger moiety shall include both straight and branched chains containing two to twelve carbon atoms.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0–3 heteroatoms selected from oxygen, sulfur or nitrogen, the nitrogen may be N (as in 3,4-dihydro-2H-pyrrolyl), NH (as in pyrrolidinyl) or $NR^+$ (as in N-substituted pyrrolidinyl).

The term "aryl" used alone or as part of a larger moiety as in "aralkyl", "aralkoxy", or "aryloxyalkyl", refers to monocyclic, bicyclic and tricyclic ring systems having a total of five to fourteen ring members, wherein at least one ring in the system is aromatic and wherein each ring in the system contains 3 to 7 ring members. The term "aryl" may be used interchangeably with the term "aryl ring".

The term "heterocycle", "heterocyclyl", or "heterocyclic" as used herein means non-aromatic, monocyclic, bicyclic or tricyclic ring systems having five to fourteen ring members in which one or more ring members is a heteroatom, wherein each ring in the system contains 3 to 7 ring members.

The term "heteroaryl", used alone or as part of a larger moiety as in "heteroaralkyl" or "heteroarylalkoxy", refers to monocyclic, bicyclic and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl, heteroaryl, aralkyl, or heteroaralkyl group are selected from halogen, —R°, —OR°, —SR°, 1,2-methylene-dioxy, 1,2-ethylenedioxy, protected OH (such as acyloxy), phenyl (Ph), Ph substituted with R°, —O(Ph), O-(Ph) substituted with R°, $—CH_2(Ph)$, $—CH_2(Ph)$ substituted with R°, $—CH_2CH_2(Ph)$, $—CH_2CH_2(Ph)$ substituted with R°, $—NO_2$, —CN, $—N((R°)_2$, —NR°C(O)R°, $—NR°C(O)N(R)_2$, $—NR°CO_2R°$, —NR°NR°C(O)R°, $—NR°NR°C(O)N(R°)_2$, $—NR°NR°CO_2R°$, —C(O)C(O)R°, $—C(O)CH_2C(O)R°$, $—CO_2R°$, —C(O)R°, $—C(O)N(R°)_2$, $—OC(O)N(R°)_2$, $—S(O)_2R°$, $—SO_2N(R°)_2$, —S(O)R°, $—NR°SO_2N(R°)_2$, $—NR°SO_2R°$, $—C(=S)N(R°)_2$, $—C(=NH)—N(R°)_2$, $—(CH_2)_yNHC(O)R°$, or $—(CH_2)_yNHC(O)CH(V—R°)(R°)$, wherein each R° is independently selected from hydrogen, optionally substituted $C_{1-6}$ aliphatic, an unsubstituted 5–6 membered heteroaryl or heterocyclic ring, phenyl (Ph), —O(Ph), or $—CH_2(Ph)—CH_2(Ph)$, wherein y is 0–6; and V is a&linker group. Substituents on the aliphatic group of R° are selected from $NH_2$, $NH(C_{1-4}$ aliphatic), $N(C_{1-4}$ aliphatic$)_2$, halogen, $C_{1-4}$ aliphatic, OH, $O—(C_{1-4}$ aliphatic), $NO_2$, CN, $CO_2H$, $CO_2(C_{1-4}$ aliphatic), —O(halo $C_{1-4}$ aliphatic), or halo $C_{1-4}$ aliphatic.

An aliphatic group or a non-aromatic heterocyclic ring may contain one or more substituents. Suitable substituents on the saturated carbon of an aliphatic group or of a non-aromatic heterocyclic ring are selected from those listed above for the unsaturated carbon of an aryl or heteroaryl-group and the following: =O, =S, =NNHR*, $=NN(R^*)_2$, =N—, =NNHC(O)R*, $=NNHCO_2$(alkyl), $=NNHSO_2$(alkyl), or =NR*, where each R* is independently selected from hydrogen or an optionally substituted $C_{1-6}$ aliphatic. Substituents on the aliphatic group of R* are selected from $NH_2$, $NH(C_{1-4}$ aliphatic), $N(C_{1-4}$ aliphatic$)_2$, halogen, $C_{1-4}$ aliphatic, OH, $O—(C_{1-4}$ aliphatic), $NO_2$, CN, $CO_2H$, $CO_2(C_{1-4}$ aliphatic), —O(halo $C_{1-4}$ aliphatic), or halo $C_{1-4}$ aliphatic.

Substituents on the nitrogen of a non-aromatic heterocyclic ring are selected from $—R^+$, $—N(R^+)_2$, $—C(O)R^+$, $—CO_2R^+$, $—C(O)C(O)R^+$, $—C(O)CH_2C(O)R^+$, $—SO_2R^+$, $—SO_2N(R^+)_2$, $—C(=S)N(R^+)_2$, $—C(=NH)—N(R^+)_2$, or $—NR^+SO_2R^+$; wherein $R^+$is hydrogen, an optionally substituted $C_{1-6}$ aliphatic, optionally substituted phenyl (Ph), optionally substituted —O(Ph), optionally substituted $—CH_2(Ph)$, optionally substituted $—CH_2CH_2(Ph)$, or an unsubstituted 5–6 membered heteroaryl or heterocyclic ring. Substituents on the aliphatic group or the phenyl ring of $R^+$ are selected from $NH_2$, $NH(C_{1-4}$ aliphatic), $N(C_{1-4}$ aliphatic$)_2$, halogen, $C_{1-4}$ aliphatic, OH, $O—(C_{1-4}$ aliphatic), $NO_2$, CN, $CO_2H$, $CO_2(C_{1-4}$ aliphatic), —O(halo $C_{1-4}$ aliphatic), or halo $C_{1-4}$ aliphatic.

The term "alkylidene chain" refers to an optionally substituted, straight or branched carbon chain that may be fully saturated or have one or more units of unsaturation. The optional substituents are as described above for an aliphatic group.

The term "spacer group" refers to a group that separates and orients other parts of the molecule attached thereto, such that the compound favorably interacts with functional groups in the active site of an enzyme. As used herein, the spacer group separates and orients ring A and $QR^2$ within the active site such that they may form favorable interactions with functional groups which exist within the active site of the ERK2 enzyme. When the spacer group is a 5-membered heteroaromatic ring, ring A and $QR^2$ are attached at non-adjacent positions "B" and "C", and the 5-membered ring is attached to ring A at point "D" and to $QR^2$ at point "E" as illustrated below.

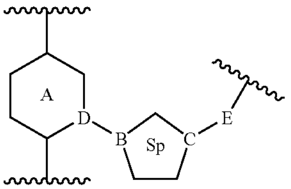

Preferably, the distance between "D" and "C" is 3.7 Å, the distance between "D" and "E" is 5.0 Å, the distance between "B" and "C" is 2.2 Å, and the distance between "B" and "E" is 3.5 Å, wherein each of the above described distances is plus/minus 0.2 Å.

The spacer group itself may also form additional interactions within the active site to further enhance inhibitory activity of the compounds. For example, when Sp is a pyrrole the pyrrole-NH may form an additional hydrogen bond within the active site of the ERK2 enzyme.

The term "linker group" means an organic moiety that connects two parts of a compound. Linkers are typically comprised of an atom such as oxygen or sulfur, a unit such as —NH—, $—CH_2—$, —CO—, or a chain of atoms, such as an alkylidene chain. The molecular mass of a linker is typically in the range of about 14 to 200. Examples of linkers include a saturated or unsaturated $C_{1-6}$ alkylidene chain which is optionally substituted, and wherein up to two saturated carbons of the chain are optionally replaced by —C(O)—, —C(O)C(O)—, $—CONR^7—$, $—CONR^7NR^7—$, $—CO_2—$, OC(O)—, $—NR^7CO_2—$, —O—, $—NR^7CONR^7—$, $—OC(O)NR^7—$, $—NR^7NR^7—$, $—NR^7CO—$, —S—, —SO—, $—SO_2—$, $—NR^7—$, $—SO_2NR^7—$, or $—NR^7SO_2—$.

As used herein, linker group Q connects Sp with $R^2$. Q may also form additional interactions within the ERK2 binding site to further enhance the inhibitory activity of the compound. When Q is a carbonyl-containing moeity such as —C(O)—, —$CO_2$—, —OC(O)—, —C(O)C(O)—, —CONH—, —$CO_2$NH—, —CONHNH—, —NHCO—, —OC(O)NH—, or —$NHCO_2$—, or a sulfonyl-containing moeity such as —$SO_2$—, —$SO_2$NH—, or —$NHSO_2$—, the carbonyl or sulfonyl oxygen forms a hydrogen-bond with lysine 54 in the ERK2 binding site. When Q is an NH-containing moeity such as —$CH_2$NH— or —NHNH—, the NH-group forms a hydrogen-bond with aspartic acid residue 167 in the ERK2 binding site. When Q is a hydrophobic group such as an alkyl chain, —O—, or —S—, Q forms additional hydrophobic interactions within the ERK2 binding site.

$R^2$ forms hydrophobic interactions within the binding site of ERK2, especially with the side-chain carbons of lysine 54 and aspartic acid 167. $R^2$ may also form hydrophobic interactions with the glycine-rich loop which is made up of amino-acid residues 33-38. When $R^2$ is substituted, the substituents may form further interactions within the binding site to enhance the inhibitory activity of the compound. For example, when a substituent on R is a hydrogen-bond donor or a hydrogen-bond acceptor, said substituent forms a hydrogen bond with enzyme-bound water molecules that exist in the binding site.

As used herein, linker group T, when present, connects Sp with $R^1$. T may also form additional interactions within the ERK2 binding site to further enhance the inhibitory activity of the compound. When T is carbonyl-containing such as —CO—, —$CO_2$—, —OCO—, —COCO—, —CONH—, —$CO_2$NH—, —CONHNH—, —NHCO—, or —$NHCO_2$—, or sulfonyl-containing such as —$SO_2$—, —$SO_2$NH—, or —$NHSO_2$—, the carbonyl or sulfonyl oxygen forms a hydrogen-bond with the NH of glutamine 105 in the ERK2 binding site. When T is NH-containing such as —$CH_2$NH— or —NHNH—, the NH-group forms a hydrogen-bond with the carbonyl of glutamine 105. When T is a hydrophobic group such as an alkyl chain, —O—, or —S—, T forms additional hydrophobic interactions with the side-chain carbons of glutamine 105 as well as isoleucine 84.

The binding interactions described herein between the compounds of this invention and the ERK2 binding-site have been determined by molecular modeling programs that are known to those of ordinary skill in the art. These molecular modeling programs include QUANTA [Molecular Simulations, Inc., Burlington, Mass., 1992] and SYBYL [Molecular Modeling Software, Tripos Associates, Inc., St. Louis, Mo., 1992]. As used herein, the amino acid numbering for the ERK2 enzyme corresponds to the Swiss-Prot database entry for accession #P28482. The Swiss-Prot database is an international protein sequence database distributed by the European Bioinformatics Institute (EBI) in Geneva, Switzerland. The database can be found at www.ebi.ac.uk/swissprot.

The compounds of this invention are limited to those that are chemically feasible and stable. Therefore, a combination of substituents or variables in the compounds described above is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least a week.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention.

Compounds of formula I or salts thereof may be formulated into compositions. In a preferred embodiment, the composition is a pharmaceutically acceptable composition. In one embodiment, the composition comprises an amount of the protein kinase inhibitor effective to inhibit a protein kinase, particularly ERK-2, in a biological sample or in a patient. In another embodiment, compounds of this invention and pharmaceutical compositions thereof, which comprise an amount of the protein kinase inhibitor effective to treat or prevent an ERK-2-mediated condition and a pharmaceutically acceptable carrier, adjuvant, or vehicle, may be formulated for administration to a patient.

The term "patient" includes human and veterinary subjects.

The term "biological sample", as used herein, includes, without limitation, cell cultures or extracts thereof; preparations of an enzyme suitable for in vitro assay; biopsied material obtained from a mammal or extracts thereof; and blood, saliva, urine, feces, semen, tears, or other body fluids or extracts thereof.

Another aspect of this invention relates to a method of treating or preventing an ERK-2-mediated disease, which method comprises administering to a patient in need of such a treatment a therapeutically effective amount of a compound of formula I or a pharmaceutically acceptable comprising said compound.

The term "ERK-2-mediated condition" or "disease", as used herein, means any disease or other deleterious condition in which ERK-2 is known to play a role. The term "ERK-2-mediated condition" or "disease" also means those diseases or conditions that are alleviated by treatment with an ERK-2 inhibitor. Such conditions include, without limitation, cancer, stroke, diabetes, hepatomegaly, cardiovascular disease including cardiomegaly, Alzheimer's disease, cystic fibrosis, viral disease, autoimmune diseases, atherosclerosis restenosis, psoriasis, allergic disorders including asthma, inflammation, neurological disorders and hormone-related diseases. The term "cancer" includes, but is not limited to the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia.

The present method is especially useful for treating a disease that is alleviated by the use of an inhibitor of ERK2 or other protein kinases. Although the present compounds were designed as ERK2 inhibitors, it has been found that certain compounds of this invention also inhibit other protein kinases such as GSK3, Aurora2, Lck, CDK2, and AKT3.

Another aspect of the invention relates to inhibiting ERK-2 activity in a biological sample, which method comprises contacting the biological sample with a compound of formula I, or a pharmaceutically acceptable composition comprising said compound.

Another aspect of this invention relates to a method of inhibiting ERK-2 activity in a patient, which method comprises administering to the patient a compound of formula I or a pharmaceutically acceptable composition comprising said compound.

Another aspect of this invention relates to a method of treating or preventing an Aurora-2-mediated disease, which method comprises administering to a patient in need of such a treatment a therapeutically effective amount of a compound of formula I or a pharmaceutically acceptable comprising said compound.

The term "Aurora-2-mediated condition" or "disease", as used herein, means any disease or other deleterious condition in which Aurora is known to play a role. The term "Aurora-2-mediated condition" or "disease" also means those diseases or conditions that are alleviated by treatment with an Aurora-2 inhibitor. Such conditions include, without limitation, cancer. The term "cancer" includes, but is not limited to the following cancers: colon, breast, stomach, and ovarian.

Another aspect of the invention relates to inhibiting Aurora-2 activity in a biological sample, which method comprises contacting the biological sample with a compound of formula I, or a pharmaceutically acceptable composition comprising said compound.

Another aspect of this invention relates to a method of inhibiting Aurora-2 activity in a patient, which method comprises administering to the patient a compound of formula I or a pharmaceutically acceptable composition comprising said compound.

Another aspect of this invention relates to a method of treating or preventing a GSK-3-mediated disease, which method comprises administering to a patient in need of such a treatment a therapeutically effective amount of a compound of formula I or a pharmaceutically acceptable comprising said compound.

The term "GSK-3-mediated condition" or "disease", as used herein, means any disease or other deleterious condition or state in which GSK-3 is known to play a role. Such diseases or conditions include, without limitation, diabetes, Alzheimer's disease, Huntington's Disease, Parkinson's Disease, AIDS-associated dementia, amyotrophic lateral sclerosis (AML), multiple sclerosis (MS), schizophrenia, cardiomycete hypertrophy, reperfusion/ischemia, and baldness.

One aspect of this invention relates to a method of enhancing glycogen synthesis and/or lowering blood levels of glucose in a patient in need thereof, which method comprises administering to the patient a therapeutically effective amount of a compound of formula I or a pharmaceutically acceptable thereof. This method is especially useful for diabetic patients. Another method relates to inhibiting the production of hyperphosphorylated Tau protein, which is useful in halting or slowing the progression of Alzheimer's disease. Another method relates to inhibiting the phosphorylation of β-catenin, which is useful for treating schizophrenia.

Another aspect of the invention relates to inhibiting GSK-3 activity in a biological sample, which method comprises contacting the biological sample with a compound of formula I.

Another aspect of this invention relates to a method of inhibiting GSK-3 activity in a patient, which method comprises administering to the patient a compound of formula I or a pharmaceutically acceptable composition comprising said compound.

Inhibition of ERK2, Aurora2, CDK2, GSK-3, Lck, or AKT3 kinase activity in a biological sample is useful for a variety of purposes which are known to one of skill in the art. Examples of such purposes include; but are not limited to, blood transfusion, organ-transplantation, biological specimen storage, and biological assays.

The term "pharmaceutically acceptable carrier, adjuvant, or vehicle" refers to a non-toxic carrier, adjuvant, or vehicle that may be administered to a patient, together with a compound of this invention, and which does not destroy the pharmacological activity thereof.

The amount effective to inhibit protein kinase, for example, Aurora-2 and GSK-3, is one that measurably inhibits the kinase activity where compared to the activity of the enzyme in the absence of an inhibitor. Any method may be used to determine inhibition, such as, for example, the Biological Testing -Examples described below.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids; such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In addition to the compounds of this invention, pharmaceutically acceptable derivatives of the compounds of this invention may also be employed in compositions to treat or prevent the above-identified diseases or disorders.

A "pharmaceutically acceptable derivative" means any pharmaceutically acceptable salt, ester, salt of an ester or other derivative of a compound of this invention which, upon administration to a recipient, is capable of providing, either directly or indirectly, a compound of this invention or an inhibitorily active metabolite or residue thereof. Particularly favored derivatives are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}\ alkyl)_4$ salts. This invention also envisions the quaternization of any basic nitrogen-containing groups of the compounds disclosed herein. Water or oil-soluble or dispersible products may be obtained by such quaternization.

The amount of the protein kinase inhibitor that may be combined with the carrier materials to produce a single dosage form will vary depending upon the patient treated and the particular mode of administration. Preferably, the compositions should be formulated so that a dosage of between 0.01–100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of the inhibitor will also depend upon the particular compound in the composition.

The kinase inhibitors of this invention or pharmaceutical compositions thereof may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by precoating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition. Implantable devices coated with a kinase inhibitor of this invention are another embodiment of the present invention.

Depending upon the particular protein kinase-mediated condition to be treated or prevented, additional therapeutic agents, which are normally administered to treat or prevent that condition, may be administered together with the inhibitors of this invention. For example, in the treatment of cancer other chemotherapeutic agents or other anti-proliferative agents may be combined with the protein kinase inhibitors of this invention to treat cancer. These agents include, without limitation, adriamycin, dexamethasone, vincristine, cyclophosphamide, fluorouracil, topotecan, taxol, interferons, and platinum derivatives.

Other examples of agents the inhibitors of this invention may also be combined with include, without limitation, agents for treating diabetes such as insulin or insulin analogues, in injectable or inhalation form, glitazones, alpha glucosidase inhibitors, biguanides, insulin sensitizers, and sulfonyl ureas; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

Those additional agents may be administered separately from the protein kinase inhibitor-containing composition, as part of a multiple dosage regimen. Alternatively, those agents may be part of a single dosage form, mixed together with the protein kinase inhibitor of this invention in a single composition.

Compounds of this invention may exist in alternative tautomeric forms. Unless otherwise indicated, the representation of either tautomer is meant to include the other.

Accordingly, the present invention relates to compounds of formula I wherein Ring A is a pyridine (II), pyrimidine (III), or triazine (IV) ring as shown below:

II

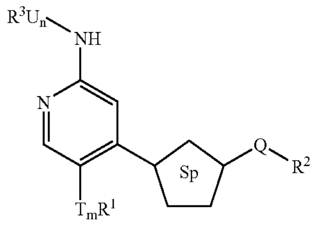

III

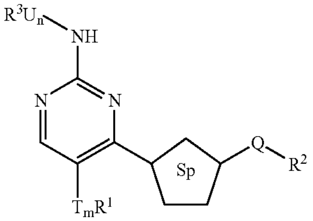

IV

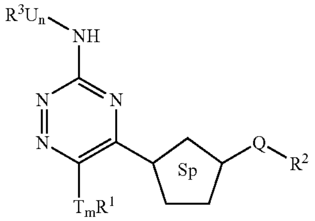

or a pharmaceutically acceptable derivative thereof, wherein Sp, $T_mR^1$, $R^2$, $U_nR^3$, Q, and T are as described above.

Examples of suitable Sp groups of formula I include pyrrole (a), imidazole (b), pyrazole (c), triazole (d), oxazole (e), isoxazole (f), 1,3-thiazole (g), 1,2-thiazole (h), furan (i), and thiophene (j), as shown below:

a

b

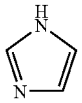

c

d

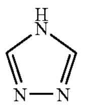

e

f

-continued

g

h

i

j wherein each of a through j is optionally substituted with $R^6$.

Preferred $T_mR^1$ groups of formula I are selected from hydrogen, $N(R^4)_2$, OH, 3–6 membered carbocyclyl, or an optionally substituted group selected from $C_{1-6}$ aliphatic or a 5–6 membered aryl or heteroaryl ring. When $R^1$ is an optionally substituted phenyl or aliphatic group, preferred substituents on the phenyl or aliphatic group are $R^7$, halo, nitro, alkoxy, and amino. Preferred $T_mR^1$ groups are methyl, ethyl, propyl, cyclopropyl, cyclohexyl, $CH_2OCH_3$, $CH_2OH$, $NH_2$, $NHCH_3$, NHAc, $NHC(O)NHCH_3$, and $CH_2NHCH_3$. More preferred $T_mR^1$ groups of formula I are those listed in Table 1 below.

Preferred $R^3$ groups of formula I are hydrogen, carbocyclyl, —$CH(R^8)R$, or an optionally substituted group selected from $C_{1-4}$ aliphatic, 3–6 membered heterocyclic, or a 5–6 membered aryl or heteroaryl ring. Examples of such groups include methyl, ethyl, propyl, cyclopropyl, cyclohexyl, benzyl, isoxazolyl, tetrahydrofuranyl, and isopropyl. When $R^3$ is optionally substituted phenyl, preferred substituents on the phenyl ring are halogen, alkyl, alkoxy, haloalkyl, Obenzyl, Ophenyl, $OCF_3$, OH, $SO_2NH_2$, and methylene dioxy. When $R^3$ is —$CH(R^8)R$, examples of such groups include —$CH(CH_2OH)$phenyl, —$CH(CH_2OH)$ethyl, —$CH(CH_2OH)_2$, —$CH(CH_2OH)$isopropyl, and —$CH(CH_2OH)CH_2$cyclopropyl. Preferred $U_n$ groups, when present, are —$CH_2$—, —O—, —$NR^7$—, —NHCO—, and —$NHCO_2$—. More preferred $U_nR^3$ groups of formula I are those listed in Table 1 below.

When $R^2$ is $R^5$, preferred $R^5$ groups are pyrrolidin-1-yl, morpholin-4-yl, piperidin-1-yl, and piperazin-1-yl, 4-methyl [1,4]diazepan-1-yl, 4-phenyl-piperazine-1-yl, wherein each group is optionally substituted. When $R^2$ is $(CH_2)_yR^5$, $(CH_2)_y$ $CH(R^5)_2$, or —$N(R^4)_2$, preferred $R^5$ groups are further selected from pyridin-3-yl, pyridin-4-yl, imidazolyl, furan-2-yl, 1,2,3,4-tetrahydroisoquinoline, tetrahydrofuran-2-yl, cyclohexyl, phenyl, benzyl, —$CH_2OH$, —$(CH_2)_2OH$, and isopropyl, wherein each group is optionally substituted. Preferred substituents on $R^5$ are —OH, pyridyl, piperidinyl, and optionally substituted phenyl. When $R^2$ is —$(CH_2)_yCH(R^8)CH(R^5)_2$, preferred $R^8$ groups are $R^7$ and $OR^7$ such as OH and $CH_2OH$ and preferred $R^5$ are as described above. Preferred —$(CH_2)_yCH(R^8)CH(R^5)_2$ groups of formula I are —CH(OH)CH(OH)phenyl and —CH(Me)CH(OH)phenyl. Other preferred —$QR^2$ groups are those listed in Table 1 below.

Preferred compounds of formula I are those having one or more, more preferably more than one, and most preferably all, of the features selected from the group consisting of:

(a) $R^3$ is hydrogen, carbocyclyl, —$CH(R^8)R$, or an optionally substituted group selected from $C_{1-4}$ aliphatic, 3–6 membered heterocyclic, or a 5–6 membered aryl or heteroaryl ring;

(b) $T_mR^1$ is hydrogen, amino, OH, 3–6-membered carbocyclyl, or an optionally substituted group selected from $C_{1-6}$ aliphatic or a 5–6 membered aryl or heteroaryl ring;

(c) Q is —CO—, —$CO_2$—, —CONH—, —$SO_2$—, —$SO_2NH$—, —OC(O)NH—, —C(O)ONH—, or —CONHNH—;

(d) $R^2$ is —$NR^4(CH_2)_yN(R^4)_2$, —$(CH_2)_yR^5$, —$(CH_2)_yCH(R^5)_2$, or —$(CH_2)_yCH(R^8)CH(R^5)_2$;

(f) $R^4$ is R, $R^7$, or —$(CH_2)_yCH(R^5)_2$; and (g) $R^5$ is an optionally substituted group selected from $C_{1-6}$ aliphatic, phenyl, 5–6 membered heteroaryl, or 5–6 membered heterocyclyl.

More preferred compounds of formula I are those having one or more, more preferably more than one, or most preferably all, of the features selected from the group consisting of:

(a) $R^3$ is selected from hydrogen, methyl, ethyl, propyl, cyclopropyl, cyclohexyl, isopropyl, —$CH(CH_2OH)$phenyl, —$CH(CH_2OH)$ethyl, —$CH(CH_2OH)_2$, —$CH(CH_2OH)$isopropyl, —$CH(CH_2OH)CH_2$cyclopropyl, or an optionally substituted phenyl, benzyl, or isoxazolyl group;

(b) $T_mR^1$ is selected from optionally substituted phenyl, methyl, ethyl, propyl, cyclopropyl, cyclohexyl, $CH_2OCH_3$, $CH_2OH$, OH, $NH_2$, $NHCH_3$, NHAc, $NHC(O)NHCH_3$, or $CH_2NHCH_3$;

(c) Q is —CO—, —CONH—, —$SO_2$—, or —$SO_2NH$—;

(d) $R^2$ is —$(CH_2)_yR^5$, —$(CH_2)_yCH(R^5)_2$, or —$(CH_2)_yCH(R^8)CH(R^5)_2$, wherein $R^8$ is OH or $CH_2OH$; and (e) $R^5$ is —$CH_2OH$, —$(CH_2)_2OH$, isopropyl, or an optionally substituted group selected from pyrrolidin-1-yl, morpholin-4-yl, piperidin-1-yl, piperazin-1-yl, 4-methyl[1,4]diazepan-1-yl, 4-phenyl-piperazine-1-yl, pyridin-3-yl, pyridin-4-yl, imidazolyl, furan-2-yl, 1,2,3,4-tetrahydroisoquinoline, tetrahydrofuran-2-yl, cyclohexyl, phenyl, or benzyl.

A preferred embodiment of this invention relates to compounds of formula I':

I'

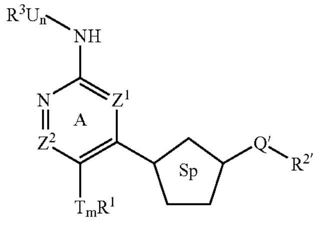

or a pharmaceutically acceptable derivative thereof, wherein:

Sp is a spacer group comprising a 5-membered heteroaromatic ring, wherein Ring A and $Q'R^{2'}$ are attached to Sp at non-adjacent positions; and wherein Sp has up to two $R^6$ substituents, provided that two substitutable carbon ring atoms in Sp are not simultaneously substituted by $R^6$;

$Z^1$ and $Z^2$ are each independently selected from N or CH;

Q' is selected from —$CO_2$—, —$C(O)NR^7$— or —$SO_2NR^7$—;

T is a linker group;

U is selected from —$NR^7$—, —$NR^7CO$—, —$NR^7CONR^7$—, —$NR^7CO_2$—, —O—, —$CONR^7$—, —CO—, —$CO_2$—, —OC(O)—, —$NR^7SO_2$—, —$SO_2NR^7$—, —NR $SO_2NR^7$—, or —$SO_2$—;

m and n are each independently selected from zero or one;

R' is selected from hydrogen, CN, halogen, R, $N(R^7)_2$, OR, or OH;

$R^{2'}$ is selected from —$(CH_2)_yCH(R^5)_2$ or —$(CH_2)_yCH(R^8)CH(R^5)_2$;

y is 0–6;

$R^3$ is selected from $R^7$, R, —$(CH_2)_yCH(R^8)R$, CN, —$(CH_2)_yCH(R^8)CH(R^5)_2$, or —$(CH_2)_yCH(R^8)N(R^4)_2$;

each R is independently selected from an optionally substituted group selected from $C_{1-6}$ aliphatic, $C_{6-10}$ aryl, a heteroaryl ring having 5–10 ring atoms, or a heterocyclyl ring having 3–10 ring atoms;

each $R^4$ is independently selected from R, $R^7$, —$COR^7$, —$CO_2R$, —$CON(R^7)_2$, —$SO_2R^7$, —$(CH_2)_yR^5$, or —$(CH_2)_yCH(R^5)_2$;

each $R^5$ is independently selected from R, OR, $CO_2R$, $(CH_2)_yN(R^7)_2$, $N(R^7)_2$, $OR^7$, $SR^7$, $NR^7COR^7$, $NR^7CON(R^7)_2$, $CON(R^7)_2$, $SO_2R^7$, $NR^7SO_2R^7$, $COR^7$, CN, or $SO_2N(R^7)_2$;

each $R^6$ is independently selected from $R^7$, F, Cl, $(CH_2)_yN(R^7)_2$, $N(R^7)_2$, $OR^7$, $SR^7$, $NR^7COR^7$, $NR^7CON(R^7)_2$, $CON(R^7)_2$, $SO_2R^7$, $NR^7SO_2R^7$, $COR^7$, CN, or $SO_2N(R^7)_2$;

each $R^7$ is independently selected from hydrogen or an optionally substituted $Cl_6$ aliphatic group, or two $R^7$ on the same nitrogen are taken together with the nitrogen to form a 5–8 membered heterocyclyl or heteroaryl ring;

$R^8$ is selected from R, $(CH_2)_wOR^7$, $(CH_2)_wN(R^4)_2$, or $(CH_2)_wSR^7$; and each w is independently selected from 0–4.

Examples of suitable Sp groups of formula I' include pyrrole (a), imidazole (b), pyrazole (c), triazole (d), oxazole (e), isoxazole (f), 1,3-thiazole (g), 1,2-thiazole (h), furan (i), and thiophene (j), as shown below:

a

b

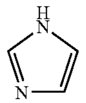

c

d

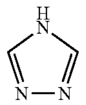

e

-continued f

g

h

i

j

wherein each of a through j is optionally substituted with $R^6$.

Accordingly, the present invention relates to compounds of formula I' wherein Ring A is a pyridine (II'), pyrimidine (III'), or triazine (IV') ring as shown below:

II'

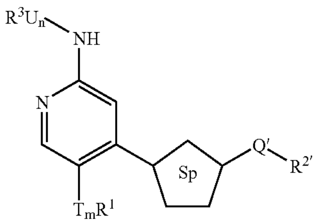

III'

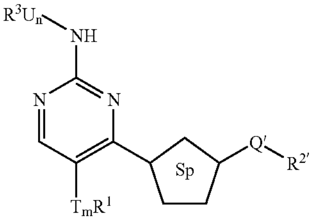

IV'

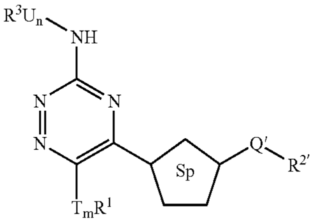

or a pharmaceutically acceptable derivative thereof, wherein Sp, $T_mR^1$, $Q'R^{2'}$, and $U_nR^3$ are as described above.

Preferred $R^5$ groups of formula I' are R or $OR^7$. Examples of such groups include OH, $CH_2OH$, carbocyclic, or optionally substituted 5 or 6-membered aryl or heteroaryl rings, such as phenyl, pyridyl, and cyclohexyl. Preferred $R^8$ groups of formula I' are R and $OR^7$, wherein R is an optionally substituted group selected from $C_{1-4}$ aliphatic, 3–6 membered heterocyclic, or a 5–6 membered aryl or heteroaryl ring. Examples of such groups include phenyl, methyl, ethyl, OH, and $CH_2OH$. Preferred substituents on the $R^5$ aryl or heteroaryl ring are halogen, haloalkyl, OR°, and R°.

Preferred $T_mR^1$ groups of formula I' are hydrogen, $N(R^4)_2$, OH, 3–6 membered carbocyclyl, or an optionally substituted group selected from $C_{1-6}$ aliphatic or a 5–6 membered aryl or heteroaryl ring. When $R^1$ is an optionally substituted phenyl or aliphatic group, preferred substituents on the phenyl or aliphatic group are $R^7$, halo, nitro, alkoxy, and amino. Preferred $T_mR^1$ groups include methyl, ethyl, propyl, cyclopropyl, cyclohexyl, $CH_2OCH_3$, $CH_2OH$, $NH_2$, $NHCH_3$, NHAc, $NHC(O)NHCH_3$, and $CH_2NHCH_3$. More preferred $T_mR^1$ groups of formula I' are those listed in Table 1 below.

Preferred $R^3$ groups of formula I' are hydrogen, carbocyclyl, —$CH(R^8)R$, or an optionally substituted group selected from $C_{1-4}$ aliphatic, 3–6 membered heterocyclic, or a 5–6 membered aryl or heteroaryl ring. Examples of such groups include methyl, ethyl, propyl, cyclopropyl, cyclohexyl, benzyl, isoxazolyl, tetrahydrofuranyl, and isopropyl. When $R^3$ is optionally substituted phenyl, preferred substituents on the phenyl ring are halogen, alkyl, alkoxy, haloalkyl, Obenzyl, Ophenyl, $OCF_3$, OH, $SO_2NH_2$, and methylene dioxy. When $R^3$ is —$CH(R^8)R$, examples of such groups include —$CH(CH_2OH)$phenyl, —$CH(CH_2OH)$ethyl, —$CH(CH_2OH)_2$, —$CH(CH_2OH)$isopropyl, and —$CH(CH_2OH)CH_2$cyclopropyl. Preferred $U_n$ groups, when present, are —$CH_2$—, —O—, —$NR^7$—, —NHCO—, and —$NHCO_2$—. More preferred $U_nR^3$ groups of formula I' are those listed in Table 1 below.

Preferred compounds of formula I' are those having one or more, more preferably more than one, and most preferably all, of the features selected from the group consisting of:

(a) $R^3$ is hydrogen, carbocyclyl, —$CH(R^8)R$, or an optionally substituted group selected from $C_{1-4}$ aliphatic, 3–6 membered heterocyclic, or a 5–6 membered aryl or heteroaryl ring;

(b) $T_mR^1$ is hydrogen, amino, OH, 3–6 membered carbocyclyl, or an optionally substituted group selected from $C_{1-6}$ aliphatic or a 5–6 membered aryl or heteroaryl ring; and (c) $R^5$ is R or $OR^7$, wherein R is carbocyclic, or an optionally substituted 5 or 6-membered aryl or heteroaryl ring.

More preferred compounds of formula I' are those having one or more, more preferably more than one, and most preferably all, of the features selected from the group consisting of:

(a) $R^3$ is selected from hydrogen, methyl, ethyl, propyl, cyclopropyl, cyclohexyl, isopropyl, —$CH(CH_2OH)$phenyl, —$CH(CH_2OH)$ethyl, —$CH(CH_2OH)_2$, —$CH(CH_2OH)$isopropyl, —$CH(CH_2OH)CH_2$cyclopropyl, or an optionally substituted phenyl, benzyl, or isoxazolyl group;

(b) $T_mR^1$ is selected from optionally substituted phenyl, methyl, ethyl, propyl, cyclopropyl, cyclohexyl, $CH_2OCH_3$, $CH_2OH$, OH, $NH_2$, $NHCH_3$, NHAc, $NHC(O)NHCH_3$, or $CH_2NHCH_3$; and (c) $R^5$ is OH, $CH_2OH$, carbocyclic, or an optionally substituted phenyl or pyridyl ring, and Q' is C(O)NH.

Another preferred embodiment of this invention relates to compounds of formula I'':

I''

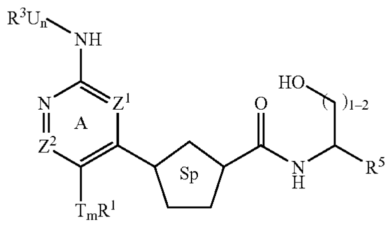

or a pharmaceutically acceptable derivative thereof, wherein:

Sp is a spacer group comprising a 5-membered heteroaromatic ring, wherein Ring A and $C(O)NHCH[(CH_2)_{1-2}OH]R^5$ are attached to Sp at non-adjacent positions; and wherein Sp has up to two $R^6$ substituents, provided that two substitutable carbon ring atoms in Sp are not simultaneously substituted by $R^6$;

$Z^1$ and $Z^2$ are each independently selected from N or CH;

T is a linker group;

U is selected from —$NR^7$—, —$NR^7CO$—, —$NR^7CONR^7$—, —$NR^7CO_2$—, —O—, —$CONR^7$—, —CO—, —$CO_2$—, —OC(O)—, —$NR^7SO_2$—, —$SO_2NR^7$—, —$NR^7SO_2NR^7$—, or —$SO_2$—;

m and n are each independently selected from zero or one;

$R^1$ is selected from hydrogen, CN, halogen, R, $N(R^7)_2$, OR, or OH;

$R^3$ is selected from $R^7R$, —$(CH_2)_yCH(R^8)R$, CN, —$(CH_2)_yCH(R^8)CH(R^5)_2$, or —$(CH_2)_yCH(R^8)N(R^4)_2$;

each R is independently selected from an optionally substituted group selected from $C_{1-6}$ aliphatic, $C_{6-10}$ aryl, a heteroaryl ring having 5–10 ring atoms, or a heterocyclyl ring having 3–10 ring atoms;

each $R^4$ is independently selected from R, $R^7$, —$COR^7$, —$CO_2R$, —$CON(R^7)_2$, —$SO_2R^7$, —$(CH_2)_yR^5$, or —$(CH_2)_yCH(R^5)_2$, each $R^5$ is independently selected from R, OR, $CO_2R$, $(CH_2)_yN(R^7)_2$, $N(R^7)_2$, $OR^7$, $SR^7$, $NR^7COR^7$, $NR^7CON(R^7)_2$, $CON(R^7)_2$, $SO_2R^7$, $NR^7SO_2R^7$, $COR^7$, CN, or $SO_2N(R^7)_2$, each $R^6$ is independently selected from $R^7$, F, Cl, $(CH_2)_yN(R^7)_2$, $N(R^7)_2$, $OR^7$, $SR^7$, $NR^7COR^7$, $NR^7CON(R^7)_2$, $CON(R^7)_2$, $SO_2R^7$, $NR^7SO_2R^7$, $COR^7$, CN, or $SO_2N(R^7)_2$;

each $R^7$ is independently selected from hydrogen or an optionally substituted $C_{1-6}$ aliphatic group, or two $R^7$ on the same nitrogen are taken together with the nitrogen to form a 5–8 membered heterocyclyl or heteroaryl ring;

$R^8$ is selected from R, $(CH_2)_wOR^7$, $(CH_2)_wN(R^4)_2$, or $(CH_2)_wSR^7$; and each w is independently selected from 0–4.

Examples of suitable Sp groups of formula I'' include pyrrole (a), imidazole (b), pyrazole (c), triazole (d), oxazole (e), isoxazole (f), 1,3-thiazole (g), 1,2-thiazole (h), furan (i), and thiophene (j), as shown below:

a

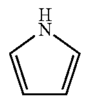

-continued b

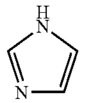

c

d

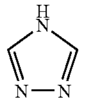

e

f

g

h

i

j

wherein each of a through j is optionally substituted with $R^6$.

Accordingly, the present invention relates to compounds of formula I" wherein Ring A is a pyridine (II"), pyrimidine (III"), or triazine (IV") ring as shown below:

II"

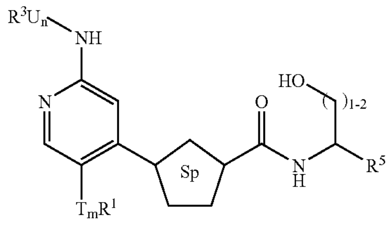

III"

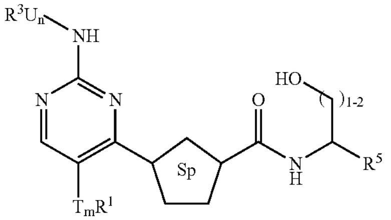

-continued

IV"

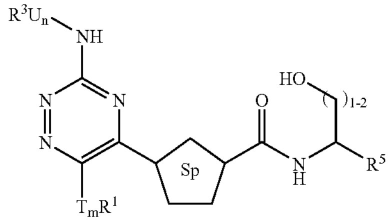

or a pharmaceutically acceptable derivative thereof, wherein Sp, $T_mR^1$, $U_nR^3$, and $R^5$ are as described above.

Preferred $T_mR^1$ groups of formula I" are hydrogen, $N(R^4)_2$, OH, 3–6 membered carbocyclyl, or an optionally substituted group selected from $C_{1-6}$ aliphatic or a 5–6 membered aryl or heteroaryl ring. When $R^1$ is an optionally substituted phenyl or aliphatic group, preferred substituents on the phenyl or aliphatic group are $R^7$, halo, nitro, alkoxy, and amino. Examples of preferred $T_mR^1$ groups include methyl, ethyl, propyl, cyclopropyl, cyclohexyl, $CH_2OCH_3$, $CH_2OH$, $NH_2$, $NHCH_3$, NHAc, $NHC(O)NHCH_3$, and $CH_2NHCH_3$. More preferred $T_mR^1$ groups of formula I" are those listed below in Table 1.

Preferred $R^3$ groups of formula I" are hydrogen, carbocyclyl, —$CH(R^8)R$, or an optionally substituted group selected from $C_{1-4}$ aliphatic, 3–6 membered heterocyclic, or a 5–6 membered aryl or heteroaryl ring. Examples of such groups include methyl, ethyl, propyl, cyclopropyl, cyclohexyl, benzyl, isoxazolyl, tetrahydrofuranyl, and isopropyl. When $R^3$ is optionally substituted phenyl, preferred substituents on the phenyl ring are halogen, alkyl, alkoxy, haloalkyl, Obenzyl, Ophenyl, $OCF_3$, OH, $SO_2NH_2$, and methylene dioxy. When $R^3$ is —$CH(R^8)R$, examples of such groups include —CH ($CH_2OH$)phenyl, —CH ($CH_2OH$)ethyl, —$CH(CH_2OH)_2$, —$CH(CH_2OH)$isopropyl, and —$CH(CH_2OH)CH_2$cyclopropyl. Preferred $U_n$ groups, when present, are —$CH_2$—, —O—, —$NR^7$—, —NHCO—, and —$NHCO_2$—. More preferred $U_nR^3$ groups of formula I" are those listed in Table 1 below.

Preferred $R^5$ groups of formula I" are optionally substituted 6-membered aryl, heteroaryl, and carbocyclic rings, such as phenyl, pyridyl, and cyclohexyl.

Preferred compounds of formula I" are those having one or more, more preferably more than one, and most preferably all, of the features selected from the group consisting of:

(a) $R^3$ is hydrogen, carbocyclyl, —$CH(R^8)R$, or an optionally substituted group selected from $C_{1-4}$ aliphatic, 3–6 membered heterocyclic, or a 5–6 membered aryl or heteroaryl ring;

(b) $T_mR^1$ is hydrogen, $N(R^4)_2$, OH, 3–6 membered carbocyclyl, or an optionally substituted group selected from $C_{1-6}$ aliphatic or a 5–6 membered aryl or heteroaryl ring; and (c) $R^5$ is an optionally substituted 6-membered aryl, heteroaryl, or carbocyclic ring.

More preferred compounds of formula I" are those having one or more, more preferably more than one, and most preferably all, of the features selected from the group consisting of:

(a) $R^3$ is selected from hydrogen, methyl, ethyl, propyl, cyclopropyl, cyclohexyl, isopropyl, —$CH(CH_2OH)$phenyl, —$CH(CH_2OH)$ethyl, —$CH(CH_2OH)_2$, —CH (b) $T_mR^1$ is selected from optionally substituted phenyl, methyl, ethyl, propyl, cyclopropyl, cyclohexyl, $CH_2OCH_3$, $CH_2OH$, $NH_2$, $NHCH_3$, NHAc, NHC(O) $NHCH_3$, or $CH_2NHCH_3$; and (c) $R^5$ is cyclohexyl or an optionally substituted phenyl or pyridylring.

Another preferred embodiment of this invention relates to compounds of formula I°:

I°

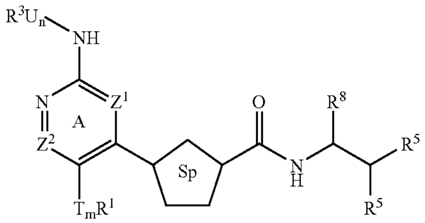

or a pharmaceutically acceptable derivative thereof, wherein:

Sp is a spacer group comprising a 5-membered heteroaromatic ring, wherein Ring A and $C(O)NNHCH(R_8)CH(R^5)_2$ are attached to Sp at non-adjacent positions; and wherein Sp has up to two $R^6$ substituents, provided that two substitutable carbon ring atoms in Sp are not simultaneously substituted by $R^6$;

$Z^1$ and $Z^2$ are each independently selected from N or CH;

T is a linker group;

U is selected from —$NR^7$—, —$NR^7CO$—, —$NR^7CONR^7$—, —$NR^7CO_2$—, —O—, —$CONR^7$—, —CO—, —$CO_2$—, —OC(O)—, —$NR^7SO_2$—, —$SO_2NR^7$—, —$NR^7SO_2NR^7$—, or —$SO_2$—;

m and n are each independently selected from zero or one;

$R^1$ is selected from hydrogen, CN, halogen, R, $N(R^7)_2$, OR, or OH;

y is 0–6;

$R^3$ is selected from $R^7R$, —$(CH_2)_yCH(R^8)R$, CN, —$(CH_2)_yCH(R^8)CH(R^5)_2$, or —$(CH_2)_yCH(R^8)N(R^4)_2$;

each R is independently selected from an optionally substituted group selected from $C_{1-6}$ aliphatic, $C_{6-10}$ aryl, a heteroaryl ring having 5–10 ring atoms, or a heterocyclyl ring having 3–10 ring atoms;

each $R^5$ is independently selected from R, OR, $CO_2R$, $(CH_2)_yN(R^7)_2$, $N(R^7)_2$, $OR^7$, $SR^7$, $NR^7COR^7$, $NR^7CON(R^7)_2$; $CON(R^7)_2$, $SO_2R^7$, $NR^7SO_2R^7$, $COR^7$, CN, or $SO_2N(R^7)_2$;

each $R^6$ is independently selected from $R^7$, F, Cl, $(CH_2)_yN(R^7)_2$, $N(R^7)_2$, $OR^7$, $SR^7$, $NR^7COR^7$, $NR^7CON(R^7)_2$, $CON(R^7)_2$, $SO_2R^7$, $NR^7SO_2R^7$, $COR^7$, CN, or $SO_2N(R^7)_2$;

each $R^7$ is independently selected from hydrogen or an optionally substituted $C_{1-6}$ aliphatic group, or two $R^7$ on the same nitrogen are taken together with the nitrogen to form a 5–8 membered heterocyclyl or heteroaryl ring;

$R^8$ is selected from R, $(CH_2)_wOR^7$, $(CH_2)_wN(R^4)_2$, or $(CH_2)_wSR^7$; and each w is independently selected from 0–4.

Examples of suitable Sp groups of formula I° include pyrrole (a), imidazole (b), pyrazole (c), triazole (d), oxazole (e), isoxazole (f), 1,3-thiazole (g), 1,2-thiazole (h), furan (i), and thiophene (j), as shown below:

a

b

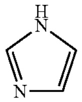

c

d

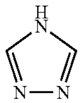

e

f

g

h

i

j

wherein each of a through j is optionally substituted with $R^6$.

Accordingly, the present invention relates to compounds of formula I° wherein Ring A is a pyridine (II°), pyrimidine (III°), or triazine (IV°) ring as shown below:

II°

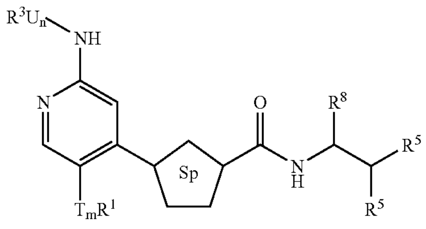

-continued

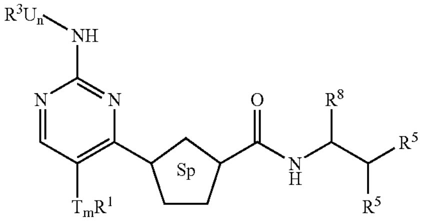

III°

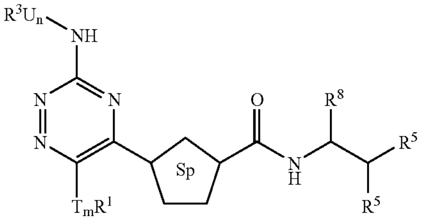

IV° or a pharmaceutically acceptable derivative thereof, wherein Sp, $T_mR^1$, $R^5$, $U_nR^3$, and $R^8$ are as described above.

Preferred $R^5$ groups of formula I° are R or $OR^7$. Examples of such groups include OH, $CH_2OH$, carbocyclic, or optionally substituted5 or 6-membered aryl or heteroaryl rings, such as phenyl, pyridyl, and cyclohexyl. Preferred $R^8$ groups of formula I° are R and $OR^7$; wherein R is an optionally substituted group selected from $C_{1-4}$ aliphatic, 3–6 membered heterocyclic, or a 5–6 membered aryl or heteroaryl ring. Examples of such groups include phenyl, methyl, ethyl, OH, and $CH_2OH$. Preferred substituents on the $R^5$ aryl or heteroaryl ring are halogen, haloalkyl, OR°, and R°.

Preferred $T_mR^1$ groups of formula I° are hydrogen, $N(R^4)_2$, OH, 3–6 membered carbocyclyl, or an optionally substituted group selected from $C_{1-6}$ aliphatic or a 5–6 membered aryl or heteroaryl ring. When $R^1$ is an optionally substituted phenyl or aliphatic group, preferred substituents on the phenyl or aliphatic group are $R^7$, halo, nitro, alkoxy, and amino. More preferred $T_mR^1$ groups are methyl, ethyl, propyl, cyclopropyl, cyclohexyl, $CH_2OCH_3$, $CH_2OH$, $NH_2$, $NHCH_3$, NHAc, $NHC(O)NHCH_3$, and $CH_2NHCH_3$. Most preferred $T_mR^1$ groups of formula I° are those listed in Table 1 below.

Preferred $R^3$ groups of formula I° are hydrogen, carbocyclyl, —$CH(R^8)R$, or an optionally substituted group selected from $C_{1-4}$ aliphatic, 3–6 membered heterocyclic, or a 5–6 membered aryl or heteroaryl ring. Examples of such groups include methyl, ethyl, propyl, cyclopropyl, cyclohexyl, benzyl, isoxazolyl, tetrahydrofuranyl, and isopropyl. When $R^3$ is optionally substituted phenyl, preferred substituents on the phenyl ring are halogen, alkyl, alkoxy, haloalkyl, Obenzyl, Ophenyl, $OCF_3$, OH, $SO_2NH_2$, and methylene dioxy. When $R^3$ is —$CH(R^8)R$, examples of such groups include —$CH(CH_2OH)$phenyl, —$CH(CH_2OH)$ethyl, —$CH(CH_2OH)_2$, —$CH(CH_2OH)$isopropyl, and —$CH(CH_2OH)CH_2$cyclopropyl. Preferred $U_n$ groups, when present, are —$CH_2$—, —O—, —$NR^7$—, —NHCO—, and —$NHCO_2$—. More preferred $U_nR^3$ groups of formula I° are those listed in Table 1 below.

Preferred compounds of formula I° are those having one or more, more preferably more than one, and most preferably all, of the features selected from the group consisting of:

(a) $R^3$ is hydrogen, carbocyclyl, —$CH(R^8)R$, or an optionally substituted group selected from $C_{1-4}$ aliphatic, 3–6 membered heterocyclic, or a 5–6 membered aryl or heteroaryl ring;

(b) $T_mR^1$ is hydrogen, amino, OH, 3–6 membered carbocyclyl, or an optionally substituted group selected from $C_{1-6}$ aliphatic or a 5–6 membered aryl or heteroaryl ring; and (c) $R^5$ is R or $OR^7$, wherein R is carbocyclic, or an optionally substituted5 or 6-membered aryl or heteroaryl ring.

More preferred compounds of formula I° are those having one or more, more preferably more than one, and most preferably all, of the features selected from the group consisting of:

(a) $R^3$ is selected from hydrogen, methyl, ethyl, propyl, cyclopropyl, cyclohexyl, isopropyl, —$CH(CH_2OH)$phenyl, —$CH(CH_2OH)$ethyl, —$CH(CH_2OH)_2$, —$CH(CH_2OH)$isopropyl, —$CH(CH_2OH)CH_2$cyclopropyl, or an optionally substituted phenyl, benzyl, or isoxazolyl group;

(b) $T_mR^3$ is selected from optionally substituted phenyl, methyl, ethyl, propyl, cyclopropyl, cyclohexyl, $CH_2OCH_3$, $CH_2OH$, OH, $NH_2$, $NHCH_3$, NHAc, $NHC(O)NHCH_3$, or $CH_2NHCH_3$; and (c) $R^5$ is OH, $CH_2OH$, carbocyclic, or an optionally substitutedphenyl or pyridyl ring.

A preferred embodiment relates to compounds of formula III-a:

III-a

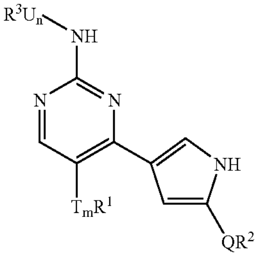

or a pharmaceutically acceptable derivative thereof.

Preferred $T_mR^1$ groups of formula III-a are hydrogen, $N(R^4)_2$, OH, 3–6 membered carbocyclyl, or an optionally substituted group selected from $C_{1-6}$ aliphatic or a 5–6 membered aryl or heteroaryl ring. When $R^1$ is an optionally substituted phenyl or aliphatic group, preferred substituents on the phenyl or aliphatic group are $R^7$, halo, nitro, alkoxy, and amino. Examples of such preferred $T_mR^1$ groups include methyl, ethyl, propyl, cyclopropyl, cyclohexyl, $CH_2OCH_3$, $CH_2OH$, $NH_2$, $NHCH_3$, NHAc, $NHC(O)NHCH_3$, and $CH_2NHCH_3$. More preferred $T_mR^1$ groups of formula III-a are those listed in Table 1 below.

Preferred $R^3$ groups of formula III-a are hydrogen, carbocyclyl, —$CH(R^8)R$, or an optionally substituted group selected from $C_{1-4}$ aliphatic, 3–6 membered heterocyclic, or a 5–6 membered aryl or heteroaryl ring. Examples of such groups include methyl, ethyl, propyl, cyclopropyl, cyclohexyl, benzyl, isoxazolyl, tetrahydrofuranyl, and isopropyl. When $R^3$ is optionally substituted phenyl, preferred substituents on the phenyl ring are halogen, alkyl, alkoxy, haloalkyl, Obenzyl, Ophenyl, $OCF_3$, OH, $SO_2NH_2$, and methylene dioxy. When $R^3$ is —$CH(R^8)R$, examples of such groups are —$CH(CH_2OH)$phenyl, —$CH(CH_2OH)$ethyl, —CH $(CH_2OH)_2$, —$CH(CH_2OH)$isopropyl, and —$CH(CH_2OH)$ $CH_2$cyclopropyl. Preferred $U_n$ groups, when present, are —$CH_2$—, —O—, —$NR^7$—, —NHCO—, and —$NHCO_2$—. More preferred $U_nR^3$ groups of formula III-a are those listed in Table 1 below.

When $R^2$ is $R^5$, preferred $R^5$ groups are pyrrolidin-1-yl, morpholin-4-yl, piperidin-1-yl, and piperazin-1-yl, 4-methyl [1,4]diazepan-1-yl, 4-phenyl-piperazine-1-yl, wherein each group is optionally substituted. When $R^2$ is $(CH_2)_yR^5$, $(CH_2)_y$ $CH(R^5)_2$, or —$N(R^4)_2$, preferred $R^5$ groups are pyridin-3-yl, pyridin-4-yl, imidazolyl, furan-2-yl, 1,2,3,4-tetrahydroisoquinoline, tetrahydrofuran-2-yl, cyclohexyl, phenyl, benzyl, —$CH_2OH$, —$(CH_2)_2OH$, and isopropyl, wherein each group is optionally substituted. Preferred substituents on $R^5$ are —OH, pyridyl, piperidinyl, and optionally substituted phenyl. When $R^2$ is —$(CH_2)_yCH(R^8)CH$ $(R^5)_2$, preferred $R^3$ groups are $R^7$ and $OR^7$ such as OH and $CH_2OH$. More preferred —$QR^2$ groups are those listed in Table 1 below.

Preferred compounds of formula III-a are those having one or more, more preferably more than one, and most preferably all, of the features selected from the group consisting of:

(a) $R^3$ is hydrogen, carbocyclyl, —$CH(R^8)R$, or an optionally substituted group selected from $C_{1-4}$ aliphatic, 3-6 membered heterocyclic, or a 5-6 membered aryl or heteroaryl ring;

(b) $T_mR^1$ is hydrogen, $N(R^4)_2$, OH, 3-6 membered carbocyclyl, or an optionally substituted group selected from $C_{1-6}$ aliphatic or a 5-6 membered aryl or heteroaryl ring;

(c) Q is —CO—, —$CO_2$—, —CONH—, —$SO_2$—, —$SO_2NH$—, —OC(O)NH—, —C(O)ONH—, or —CONHNH—;

(d) $R^2$ is —$NR^4(CH_2)_yN(R^4)_2$, —$(CH_2)_yR^5$, —$(CH_2)_yCH$ $(R^5)_2$, or —$(CH_2)_yCH(R^8)CH(R^5)_2$;

(f) $R^4$ is R, $R^7$, or —$(CH_2)_yCH(R^5)_2$; and (g) $R^5$ is an optionally substituted group selected from phenyl, 5-6 membered heteroaryl, or 5-6 membered heterocyclyl.

More preferred compounds of formula III-a are those having one or more, more preferably more than one, or most preferably all, of the features selected from the group consisting of:

(a) $R^3$ is selected from hydrogen, methyl, ethyl, propyl, cyclopropyl, cyclohexyl, isopropyl, —$CH(CH_2OH)$ phenyl, —$CH(CH_2OH)$ethyl, —$CH(CH_2OH)_2$, —CH $(CH_2OH)$isopropyl, —$CH(CH_2OH)CH_2$cyclopropyl, or an optionally substituted phenyl or benzyl group;

(b) $T_mR^1$ is selected from optionally substituted phenyl, methyl, ethyl, propyl, cyclopropyl, cyclohexyl, $CH_2OCH_3$, $CH_2OH$, OH, $NH_2$, $NHCH_3$, NHAc, NHC $(O)NHCH_3$, or $CH_2NHCH_3$;

(c) Q is —CO—, —CONH—, —$SO_2$—, or —$SO_2NH$—;

(d) $R^2$ is —$(CH_2)_yR^5$, —$(CH_2)_yCH(R^5)_2$, or —$(CH_2)_yCH$ $(R^8)CH(R^5)_2$, wherein $R^8$ is OH or $CH_2OH$; and (e) $R^5$ is —$CH_2OH$, —$(CH_2)_2OH$, isopropyl, or an optionally substituted group selected from pyrrolidin-1-yl, morpholin-4-yl, piperidin-1-yl, piperazin-1-yl, 4-methyl[1,4]diazepan-1-yl, 4-phenyl-piperazine-1-yl, pyridin-3-yl, pyridin-4-yl, imidazolyl, furan-2-yl, 1,2,3,4-tetrahydroisoquinoline, tetrahydrofuran-2-yl, cyclohexyl, phenyl, or benzyl.

Preferred compounds of formula III-a include those of formula III-a':

III-a'

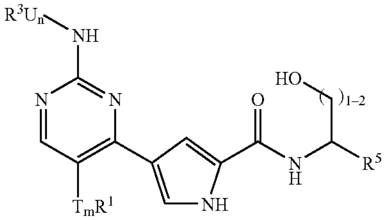

or a pharmaceutically acceptable derivative thereof.

Preferred $R^5$ groups of formula III-a' are optionally substituted6-membered aryl, heteroaryl, and carbocyclic rings, such as phenyl, pyridyl, and cyclohexyl.

Preferred $T_mR^1$ groups of formula III-a' are hydrogen, $N(R^4)_2$, OH, 3-6 membered carbocyclyl, or an optionally substituted group selected from $C_{1-6}$ aliphatic or a 5-6 membered aryl or heteroaryl ring. When R' is an optionally substituted phenyl or aliphatic group, preferred substituents on the phenyl or aliphatic group are $R^7$, halo, nitro, alkoxy, and amino. Preferred $T_mR^1$ groups are methyl, ethyl, propyl, cyclopropyl, cyclohexyl, $CH_2OCH_3$, $CH_2OH$, $NH_2$, $NHCH_3$, NHAc, $NHC(O)NHCH_3$, $CH_2NHCH_3$, and those listed in Table 1 below.

Preferred $R^3$ groups of formula III-a' are hydrogen, carbocyclyl, —$CH(R^8)R$, or an optionally substituted group selected from $C_{1-4}$ aliphatic, 3-6 membered heterocyclic, or a 5-6 membered aryl or heteroaryl ring. Examples of such groups include methyl, ethyl, propyl, cyclopropyl, cyclohexyl, benzyl, isoxazolyl, tetrahydrofuranyl, and isopropyl. When $R^3$ is optionally substituted phenyl, preferred substituents on the phenyl ring are halogen, alkyl, alkoxy, haloalkyl, Obenzyl, Ophenyl, $OCF_3$, OH, $SO_2NH_2$, and methylene dioxy, When $R^3$ is —$CH(R^8)R$, examples of such groups include —$CH(CH_2OH)$phenyl, —$CH(CH_2OH)$ethyl; —CH $(CH_2OH)_2$, —$CH(CH_2OH)$ isopropyl, and —$CH(CH_2OH)$ $CH_2$cyclopropyl. Preferred $U_n$ groups, when present, are —$CH_2$—, —O—, —$NR^7$—, —NHCO—, and —$NHCO_2$—. More preferred $U_nR^3$ of formula III-a' are those listed in Table 1 below.

Preferred compounds of formula III-a' are those having one or more, more preferably more than one, and most preferably all, of the features selected from the group consisting of:

(a) $R^3$ is hydrogen, carbocyclyl, —$CH(R^8)R$, or an optionally substituted group selected from $C_{1-4}$ aliphatic, 3-6 membered heterocyclic, or a 5-6 membered aryl or heteroaryl ring;

(b) $T_mR^1$ is hydrogen, $N(R^4)_2$, OH, 3-6 membered carbocyclyl, or an optionally substituted group selected from $C_{1-6}$ aliphatic or a 5-6 membered aryl or heteroaryl ring; and (c) $R^5$ is an optionally substituted6-membered aryl, heteroaryl, or carbocyclic ring.

More preferred compounds of formula III-a' are those having one or more, more preferably more than one, and most preferably all, of the features selected from the group consisting of:

(a) $R^3$ is selected from hydrogen, methyl, ethyl, propyl, cyclopropyl, cyclohexyl, isopropyl, —$CH(CH_2OH)$ phenyl, —$CH(CH_2OH)$ethyl, —$CH(CH_2OH)_2$, —CH $(CH_2OH)$ isopropyl, —$CH(CH_2OH)CH_2$cyclopropyl, or an optionally substituted phenyl or benzyl group;

(b) $T_mR^1$ is selected from optionally substituted phenyl, methyl, ethyl, propyl, cyclopropyl, cyclohexyl, $CH_2OCH_3$, $CH_2OH$, OH, $NH_2$, $NHCH_3$, NHAc, NHC(O)$NHCH_3$, or $CH_2NHCH_3$; and (c) $R^5$ is cyclohexyl or an optionally substituted phenyl or pyridylring.

Preferred compounds of formula III-a are further selected from those of formula III-a°:

III-a°

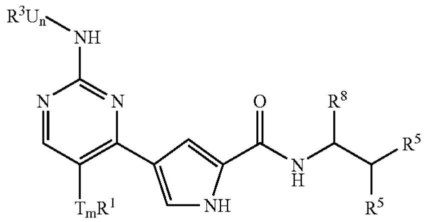

or a pharmaceutically acceptable derivative thereof.

Preferred $R^5$ groups of formula III-a' are R or $OR^7$. Examples of such groups include OH, $CH_2OH$, or optionally substituted6-membered aryl, heteroaryl, and carbocyclic rings, such as phenyl, pyridyl, and cyclohexyl. Preferred $R^8$ groups of formula III-a° are R and $OR^7$, wherein R is an optionally substituted group selected from $C_{1-4}$ aliphatic, 3-6 membered heterocyclic, or a 5-6 membered aryl or heteroaryl ring. Examples of such groups include phenyl, methyl, ethyl, OH, and $CH_2OH$.

Preferred $T_mR^1$ groups of formula III-a° are hydrogen, $N(R^4)_2$, OH, 3-6 membered carbocyclyl, or an optionally substituted group selected from $C_{1-6}$ aliphatic or a 5-6 membered aryl or heteroaryl ring. When $R^1$ is an optionally substituted phenyl or aliphatic group, preferred substituents on the phenyl or aliphatic group are $R^7$, halo, nitro, alkoxy, and amino. Preferred $T_mR^1$ groups include methyl, ethyl, propyl, cyclopropyl, cyclohexyl, $CH_2OCH_3$, $CH_2OH$, $NH_2$, $NHCH_3$, NHAc, NHC(O)$NHCH_3$, and $CH_2NHCH_3$. More preferred $T_mR^1$ groups of formula III-a° are those listed in Table 1 below.

Preferred $R^3$ groups of formula III-a° are hydrogen, carbocyclyl, —CH($R^8$)R, or an optionally substituted group selected from $C_{1-4}$ aliphatic, 3-6 membered heterocyclic, or a 5-6 membered aryl or heteroaryl ring. Examples of such groups include methyl, ethyl, propyl, cyclopropyl, cyclohexyl, benzyl, isoxazolyl, tetrahydrofuranyl, and isopropyl. When $R^3$ is optionally substituted phenyl, preferred substituents on the phenyl ring are halogen, alkyl, alkoxy, haloalkyl, Obenzyl, Ophenyl, $OCF_3$, OH, $SO_2NH_2$, and methylene dioxy. When $R^3$ is —CH($R^8$)R, examples of such groups are —CH($CH_2OH$)phenyl, —CH($CH_2OH$)ethyl, —CH($CH_2OH$)$_2$, —CH($CH_2OH$)isopropyl, and —CH($CH_2OH$)$CH_2$cyclopropyl. Preferred $U_n$ groups, when present, are —$CH_2$—, —O—, —$NR^7$—, —NHCO—, and —$NHCO_2$—. More preferred $U_nR^3$ groups of formula III-a° are those listed in Table 1 below.

Preferred compounds of formula III-a° are those having one or more, more preferably more than one, and most preferably all, of the features selected from the group consisting of:

(a) $R^3$ is hydrogen, carbocyclyl, —CH($R^8$)R, or an optionally substituted group selected from $C_{1-4}$ aliphatic, 3-6 membered heterocyclic, or a 5-6 membered aryl or heteroaryl ring;

(b) $T_mR^1$ is hydrogen, $N(R^4)_2$, OH, 3-6 membered carbocyclyl, or an optionally substituted group selected from $C_{1-6}$ aliphatic or a 5-6 membered aryl or heteroaryl ring; and (c) $R^5$ is R or $OR^7$, and $R^8$ is $R^7$ or $OR^7$.

More preferred compounds of formula III-a° are those having one or more, more preferably more than one, and most preferably all, of the features selected from the group consisting of:

(a) $R^3$ is selected from hydrogen, methyl, ethyl, propyl, cyclopropyl, cyclohexyl, isopropyl, —CH($CH_2OH$)phenyl, —CH($CH_2OH$)ethyl, —CH($CH_2OH$)$_2$, —CH($CH_2OH$)isopropyl, —CH($CH_2OH$)$CH_2$cyclopropyl, or an optionally substituted phenyl or benzyl group;

(b) $T_mR^1$ is selected from optionally substituted phenyl, methyl, ethyl, propyl, cyclopropyl, cyclohexyl, $CH_2OCH_3$, $CH_2OH$, OH, $NH_2$, $NHCH_3$, NHAc, NHC(O)$NHCH_3$, or $CH_2NHCH_3$; and (c) $R^5$ is OH, $CH_2OH$, phenyl, pyridyl, or cyclohexyl, and $R^8$ is methyl, ethyl, OH, or $CH_2OH$.

Preferred compounds of formula III-a are set Table 1 below. More preferred compounds in are those of formula III-a' or III-a°.

TABLE 1[A]

| | | Compounds of Formula III-a | |
|---|---|---|---|
| No. III-a- | $R^3U_n$ | $T_mR^1$ | Q-$R^2$ |
| 1 | H | phenyl | CON(Me)$_2$ |
| 2 | H | 3-Cl-phenyl | CO(pyrrolidin-1-yl) |
| 3 | H | 2-F-3-Cl-phenyl | CO(pyrrolidin-1-yl) |
| 4 | H | phenyl | CONH($CH_2$)$_2$pyridin-3-yl |
| 5 | H | phenyl | CO(morpholin-4-yl) |
| 6 | H | phenyl | 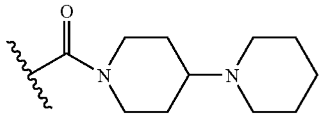 |

TABLE $1^A$-continued
Compounds of Formula III-a
| No. III-a- | $R^3U_n$ | $T_mR^1$ | Q–$R^2$ |
|---|---|---|---|
| 7 | H | 3,4-$(CH_3O)_2$-phenyl | 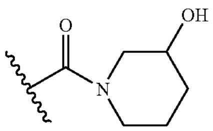 |
| 8 | H | 3,4-$(CH_3O)_2$-phenyl | 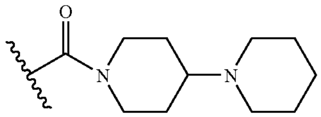 |
| 9 | H | 3-Me-phenyl | 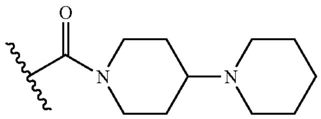 |
| 10 | H | 2-F-3-Cl-phenyl | 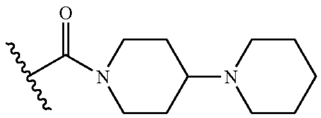 |
| 11 | H | 3-Me-phenyl | 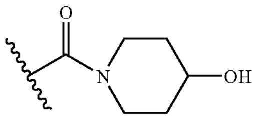 |
| 12 | H | phenyl | 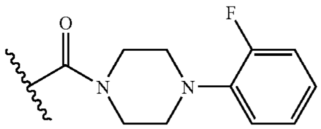 |
| 13 | H | phenyl | 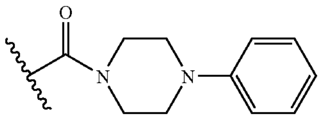 |
| 14 | H | phenyl | 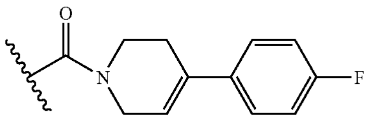 |
| 15 | H | phenyl | 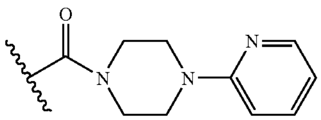 |
| 16 | H | 3,4-$(CH_3O)_2$-phenyl | CO(morpholin-4-yl) |
| 17 | H | 3,4-$(CH_3O)_2$-phenyl | $CONH(CH_2)_2$pyridin-3-yl |
| 18 | H | 3-Me-phenyl | CO(morphohn-4-yl) |
| 19 | H | 3-Me-phenyl | $CONH(CH_2)_2$pyridin-3-yl |
| 20 | H | 3-Cl-phenyl | $CONH(CH_2)_2$pyridin-3-yl |
| 21 | H | 3-Cl-phenyl | 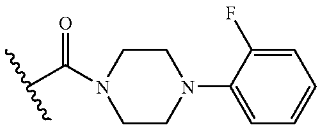 |

TABLE 1^A-continued
Compounds of Formula III-a
| No. III-a- | $R^3U_n$ | $T_mR^1$ | Q–$R^2$ |
|---|---|---|---|
| 22 | H | 3-Cl-phenyl | 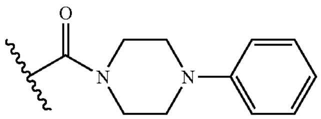 |
| 23 | H | 3-Cl-phenyl | 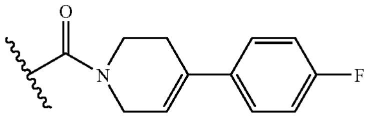 |
| 24 | H | 3-Cl-phenyl | 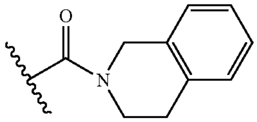 |
| 25 | H | 3-Cl-phenyl | 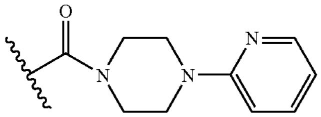 |
| 26 | H | 2-F-3-Cl-phenyl | CO(morpholin-4-yl) |
| 27 | H | 3-Cl-phenyl | CO(4-OH-piperidin-1-yl) |
| 28 | H | 3-Cl-phenyl | 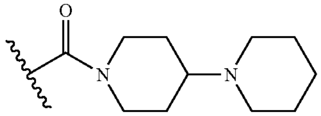 |
| 29 | H | phenyl | CON(Me)$CH_2$Ph |
| 30 | H | phenyl | 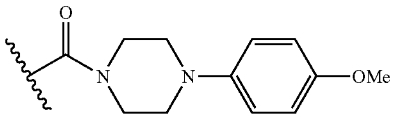 |
| 31 | H | phenyl | 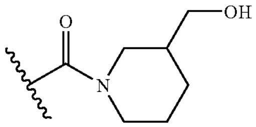 |
| 32 | H | phenyl | 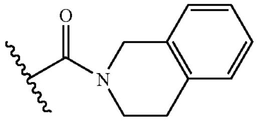 |
| 33 | H | 3,4-$(CH_3O)_2$-phenyl | CON(Me)$CH_2$Ph |
| 34 | H | 3,4-$(CH_3O)_2$-phenyl | 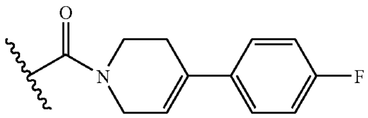 |
| 35 | H | 3,4-$(CH_3O)_2$-phenyl | 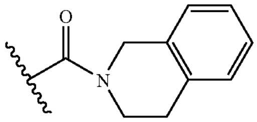 |
| 36 | H | 3-Me-phenyl | CON(Me)$CH_2$Ph |

TABLE $1^A$-continued
Compounds of Formula III-a
| No. III-a- | $R^3U_n$ | $T_mR^1$ | Q–$R^2$ |
|---|---|---|---|
| 37 | H | 3-Me-phenyl | 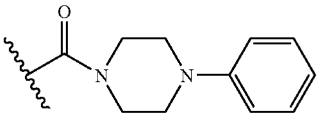 |
| 38 | H | 3-Me-phenyl | 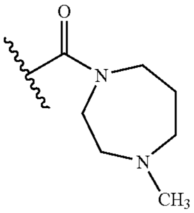 |
| 39 | H | 3-Me-phenyl | 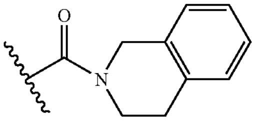 |
| 40 | H | 3-Cl-phenyl | $CON(Me)CH_2Ph$ |
| 41 | H | 3-Cl-phenyl | 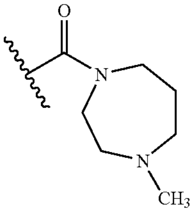 |
| 42 | H | 2-F-3-Cl-phenyl | $CON(Me)CH_2Ph$ |
| 43 | H | 3-Cl-phenyl | 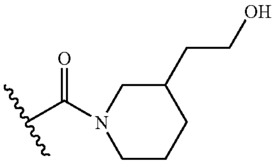 |
| 44 | H | 2-F-3-Cl-phenyl | 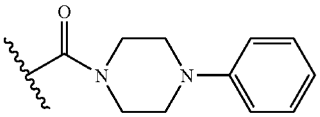 |
| 45 | H | 3-Me-phenyl | 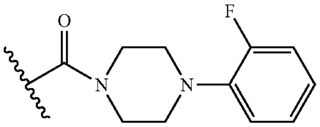 |
| 46 | H | 3-Me-phenyl | 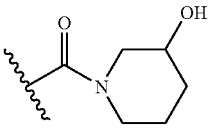 |

TABLE 1^A-continued
Compounds of Formula III-a
| No. III-a- | $R^3U_n$ | $T_mR^1$ | Q–$R^2$ |
|---|---|---|---|
| 47 | H | 3-Me-phenyl | 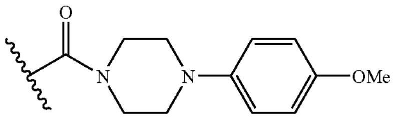 |
| 48 | H | 3-Me-phenyl | 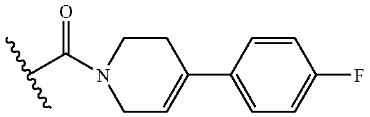 |
| 49 | H | 2-F-3-Cl-phenyl | 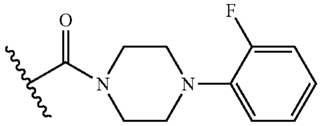 |
| 50 | H | 2-F-3-Cl-phenyl | 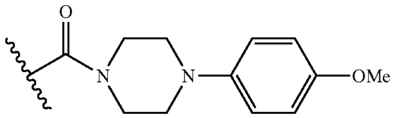 |
| 51 | H | 2-F-3-Cl-phenyl | 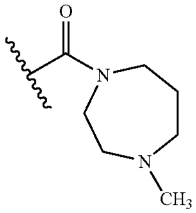 |
| 52 | H | 2-F-3-Cl-phenyl | 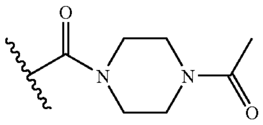 |
| 53 | H | 2-F-3-Cl-phenyl | 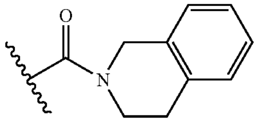 |
| 54 | H | 3-Cl-phenyl | 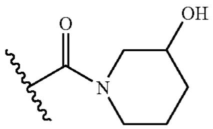 |
| 55 | H | phenyl | 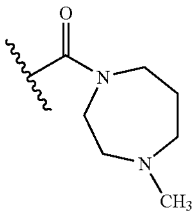 |

TABLE $1^A$-continued
Compounds of Formula III-a
| No. III-a- | $R^3U_n$ | $T_mR^1$ | Q–$R^2$ |
|---|---|---|---|
| 56 | H | 3,4-$(CH_3O)_2$-phenyl | 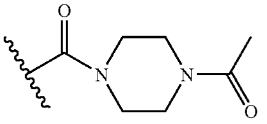 |
| 57 | H | 3,4-$(CH_3O)_2$-phenyl | 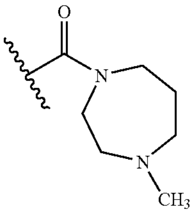 |
| 58 | H | phenyl | 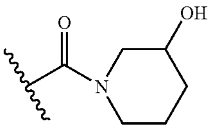 |
| 59 | H | 3-Cl-phenyl | $CONH(CH_2)_2$pyridin-3-yl |
| 60 | H | 3-Me-phenyl | 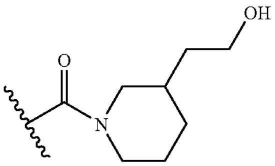 |
| 61 | H | 2-F-3-Cl-phenyl | 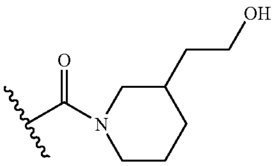 |
| 62 | H | 2-F-3-Cl-phenyl | 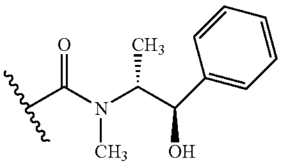 |
| 63 | H | 2-F-3-Cl-phenyl | 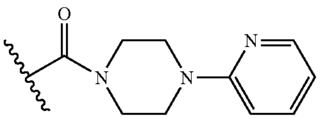 |
| 64 | H | phenyl | 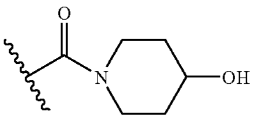 |
| 65 | H | 3,4-$(CH_3O)_2$-phenyl | 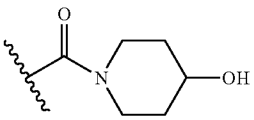 |

TABLE $1^A$-continued

Compounds of Formula III-a

| No. III-a- | $R^3U_n$ | $T_mR^1$ | Q–$R^2$ |
|---|---|---|---|
| 66 | H | 2-F-3-Cl-phenyl | 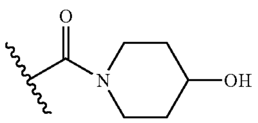 |
| 67 | H | 3,4-$(CH_3O)_2$-phenyl | 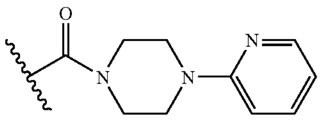 |
| 68 | H | 3-Cl-phenyl | 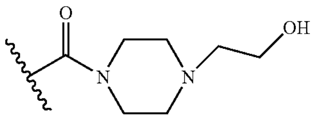 |
| 69 | H | 3-Me-phenyl | 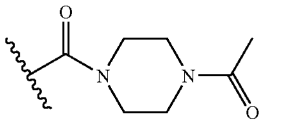 |
| 70 | H | 3,4-$(CH_3O)_2$-phenyl | 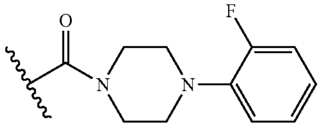 |
| 71 | H | phenyl | CO(pyrrolidin-1-yl) |
| 72 | H | 3-Cl-phenyl | CO(morpholin-4-yl) |
| 73 | H | Methyl | $CONHCH_2Ph$ |
| 74 | H | Methyl | $CONHCH_2$(3,4-$F_2$-phenyl) |
| 75 | H | Methyl | 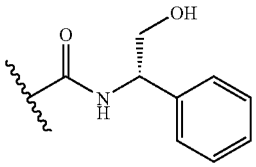 |
| 76 | H | Methyl | $CONHCH_2$(4-F-phenyl) |
| 77 | H | Methyl | $CONHCH_2$(3-Cl-phenyl) |
| 78 | H | Methyl | $CONHCH_2$(4-OMe-phenyl) |
| 79 | H | Methyl | $CONHCH_2$(3-Cl, 4-F-phenyl) |
| 80 | H | Methyl | 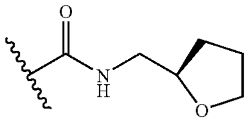 |
| 81 | H | Methyl | 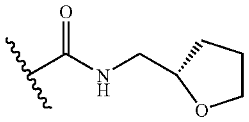 |
| 82 | H | Methyl | 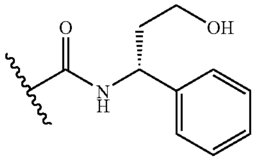 |

TABLE 1^A-continued
Compounds of Formula III-a
| No. III-a- | $R^3U_n$ | $T_mR^1$ | Q–$R^2$ |
|---|---|---|---|
| 83 | H | Methyl | 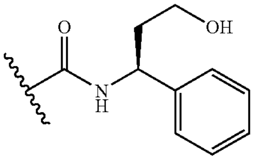 |
| 84 | H | $NH_2$ | 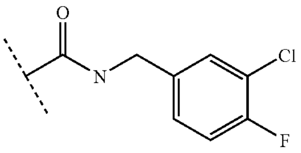 |
| 85 | H | $NHCH_3$ | 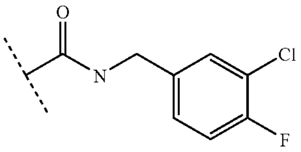 |
| 86 | H | $NHC(O)CH_3$ | 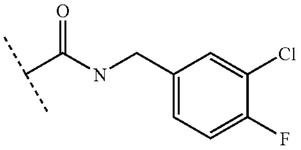 |
| 87 | H | $NHC(O)NHCH_3$ | 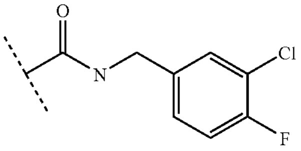 |
| 88 | H | OH | 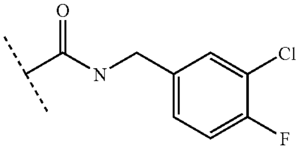 |
| 89 | H | $CH_2NHCH_3$ | 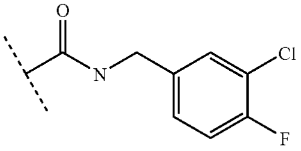 |
| 90 | H | $CH_2OH$ | 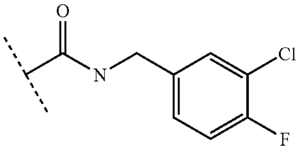 |
| 91 | N-cyclohexyl | $NHC(O)NHCH_3$ | 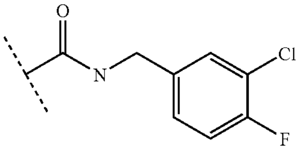 |

TABLE $1^A$-continued
Compounds of Formula III-a
| No. III-a- | $R^3U_n$ | $T_mR^1$ | Q–$R^2$ |
|---|---|---|---|
| 92 | $C(O)CH_3$ | $NHC(O)NHCH_3$ | 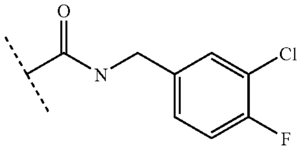 |
| 93 | $SO_2CH_3$ | OH | 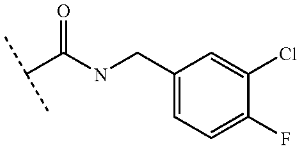 |
| 94 | H | $SO_2CH_3$ | 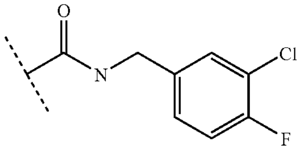 |
| 95 | H | $CH_2OH$ | 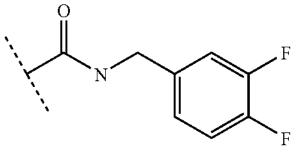 |
| 96 | cyclohexyl | $CH_3$ | 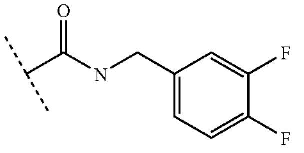 |
| 97 | H | 3,5-$Cl_2$-phenyl | $CONHCH_2$pyridin-4-yl |
| 98 | phenyl | 3,5-$Cl_2$-phenyl | $CONHCH_2$(3-$CF_3$-phenyl) |
| 99 | H | 3,5-$Cl_2$-phenyl | 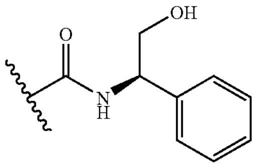 |
| 100 | H | 3,5-$Cl_2$-phenyl | 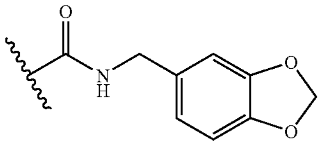 |
| 101 | H | 3,5-$Cl_2$-phenyl | 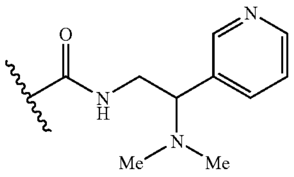 |

TABLE $1^A$-continued

Compounds of Formula III-a

| No. III-a- | $R^3U_n$ | $T_mR^1$ | Q–$R^2$ |
|---|---|---|---|
| 102 | H | 3,5-$Cl_2$-phenyl | 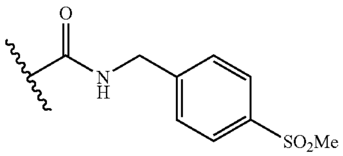 |
| 103 | phenyl | 3,5-$Cl_2$-phenyl | 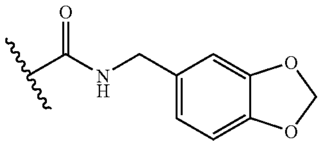 |
| 104 | phenyl | 3,5-$Cl_2$-phenyl | 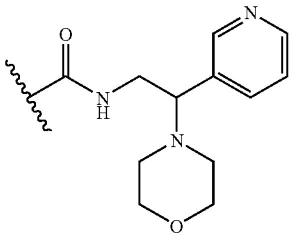 |
| 105 | H | 3-F, 5-$CF_3$-phenyl | 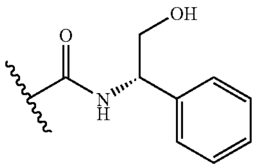 |
| 106 | H | n-propyl | $CONH(CH_2)_2$pyridin-3-yl |
| 107 | H | methyl | $CONH(CH_2)_2$pyridin-3-yl |
| 108 | methyl | methyl | $CONH(CH_2)_2$pyridin-3-yl |
| 109 | methyl | H | $CONH(CH_2)_2$pyridin-3-yl |
| 110 | ethyl | methyl | $CONH(CH_2)_2N(CH_3)_2$ |
| 111 | pheny; | methyl | $CONH(CH_2)_2CH_3$ |
| 112 | phenyl | methyl | $CONH(CH_2)_3$phenyl |
| 113 | ethyl | methyl | 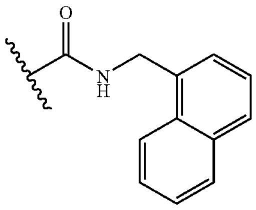 |
| 114 | ethyl | methyl | 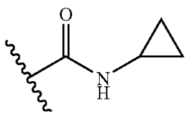 |
| 115 | ethyl | H | $CONHCH_2$(2-$CF_3$-phenyl) |
| 116 | phenyl | methyl | 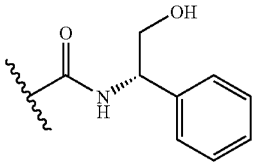 |

TABLE 1^A-continued
Compounds of Formula III-a
| No. III-a- | $R^3U_n$ | $T_mR^1$ | Q–$R^2$ |
|---|---|---|---|
| 117 | ethyl | methyl | 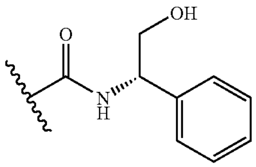 |
| 118 | ethyl | H | 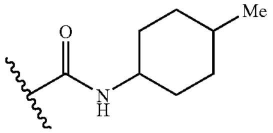 |
| 119 | phenyl | ethyl | $CONHCH(CH_3)_2$ |
| 120 | phenyl | methyl | $CONH(CH_2)_2NH_2$ |
| 121 | H | H | 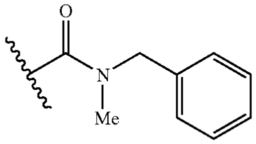 |
| 122 | H | H | 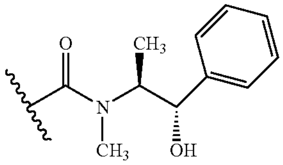 |
| 123 | ethyl | methyl | 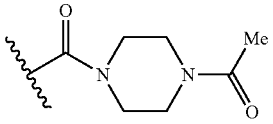 |
| 124 | ethyl | methyl | $CONH(CH_2)_3$phenyl |
| 125 | H | ethyl | 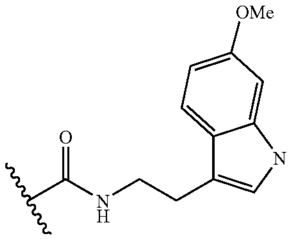 |
| 126 | phenyl | methyl | 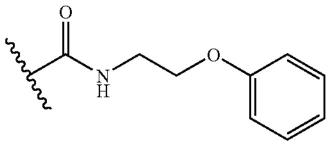 |
| 127 | phenyl | methyl | 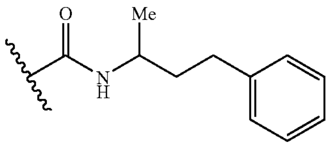 |

TABLE 1^A-continued
Compounds of Formula III-a
| No. III-a- | $R^3U_n$ | $T_mR^1$ | Q–$R^2$ |
|---|---|---|---|
| 128 | methyl | methyl | 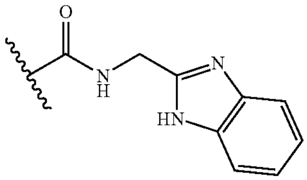 |
| 129 | methyl | methyl | 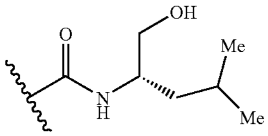 |
| 130 | phenyl | methyl | 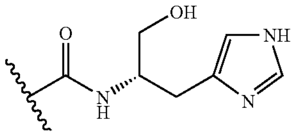 |
| 131 | H | methyl | 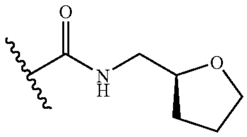 |
| 132 | $(CH_2)_2N(Et)_2$ | methyl | 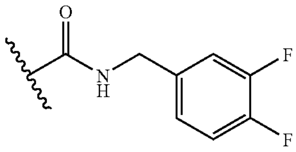 |
| 133 | 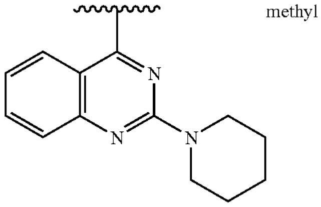 | methyl | 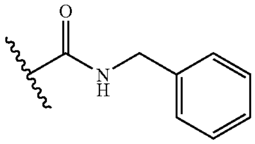 |
| 134 | methyl | methyl | 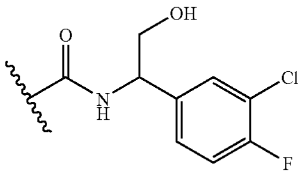 |
| 135 | phenyl | methyl | 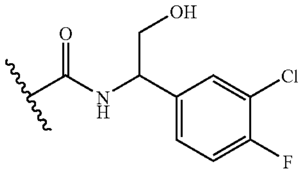 |

TABLE 1$^{A}$-continued
Compounds of Formula III-a
| No. III-a- | $R^3U_n$ | $T_mR^1$ | Q–$R^2$ |
|---|---|---|---|
| 136 | 3-F-phenyl | methyl | 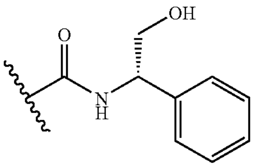 |
| 137 | 3-OMe-phenyl | methyl | 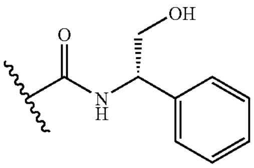 |
| 138 | 3-OH-phenyl | methyl | 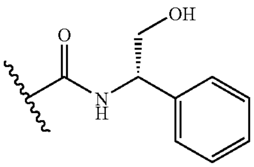 |
| 139 | 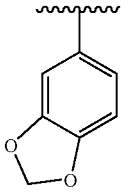 | methyl | 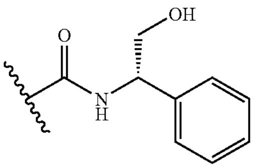 |
| 140 | 4-$SO_2NH_2$-phenyl | methyl | 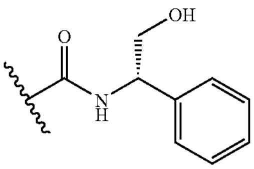 |
| 141 | 3-OBn-phenyl | methyl | 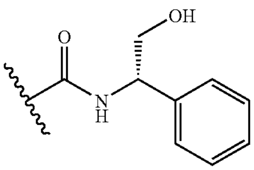 |
| 142 | 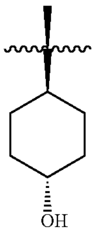 | methyl | 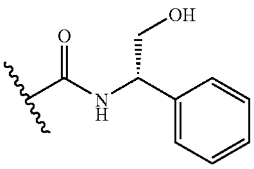 |
| 143 | phenyl | cyclohexyl | 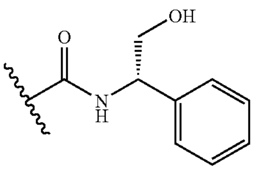 |

TABLE 1^A-continued
Compounds of Formula III-a
| No. III-a- | $R^3U_n$ | $T_mR^1$ | Q–$R^2$ |
|---|---|---|---|
| 144 | phenyl | cyclopropyl | 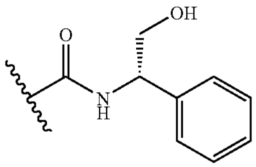 |
| 145 | phenyl | methyl | 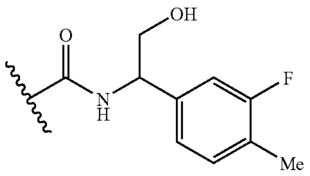 |
| 146 | phenyl | methyl | 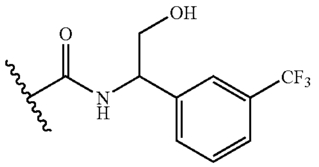 |
| 147 | 3-F-phenyl | methyl | 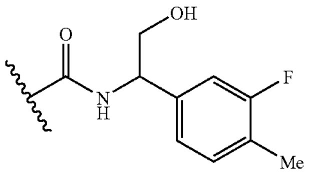 |
| 148 | 3-F-phenyl | methyl | 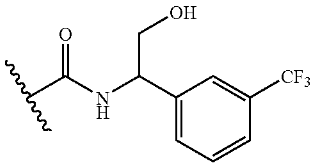 |
| 149 | 3-$CF_3$-phenyl | methyl | 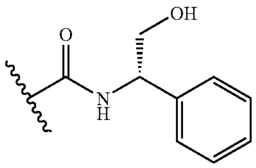 |
| 150 | $CH_2$phenyl | methyl | 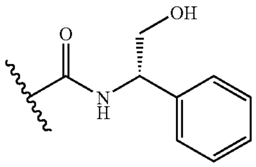 |
| 151 | 3,4-$Me_2$-phenyl | methyl | 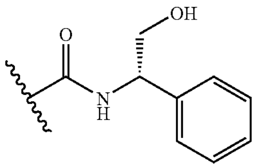 |

TABLE 1^A-continued
Compounds of Formula III-a
| No. III-a- | $R^3U_n$ | $T_mR^1$ | Q–$R^2$ |
|---|---|---|---|
| 152 | 4-OBn-phenyl | methyl | 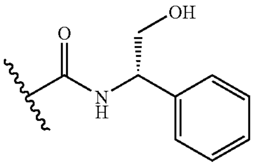 |
| 153 | $CH(CH_3)_2$ | methyl | 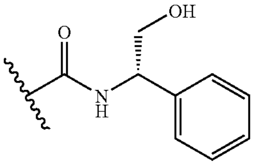 |
| 154 | $CH_2CF_3$ | methyl | 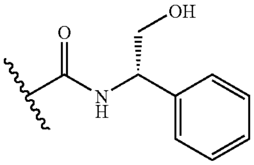 |
| 155 | 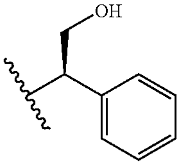 | methyl | 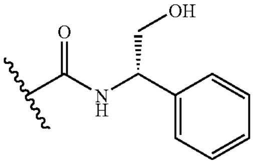 |
| 156 | 2-OMe-phenyl | methyl | 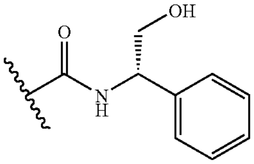 |
| 157 | 4-$OCF_3$-phenyl | methyl | 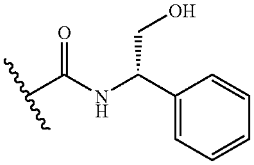 |
| 158 | $CH_2CH(CH_3)_2$ | methyl | 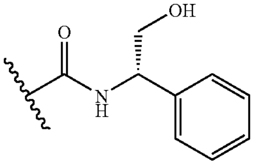 |
| 159 | $CH_2$cyclopropyl | methyl | 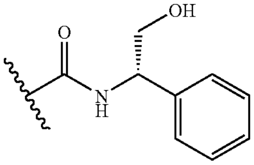 |

TABLE 1$^A$-continued
Compounds of Formula III-a
| No. III-a- | $R^3U_n$ | $T_mR^1$ | Q–$R^2$ |
|---|---|---|---|
| 160 | phenyl | $CH_2OCH_3$ | 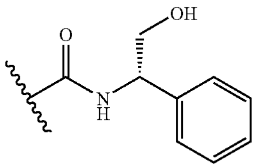 |
| 161 | H | $CH_2OCH_3$ | 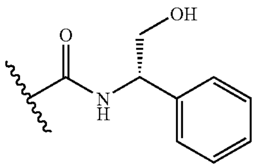 |
| 162 | cyclopropyl | methyl | 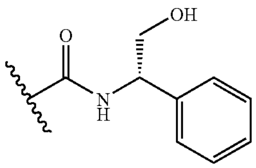 |
| 163 | $(CH_2)_2CH_3$ | methyl | 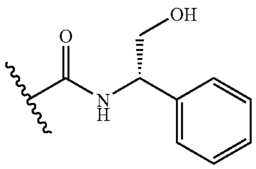 |
| 164 | phenyl | $CH_2OCH_3$ | 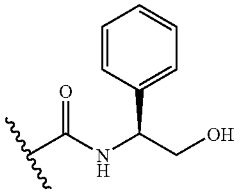 |
| 165 | phenyl | $CH_2OH$ | 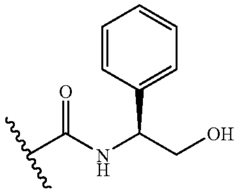 |
| 166 | 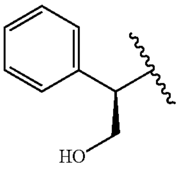 | methyl | 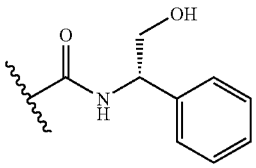 |
| 167 | ethyl | methyl | 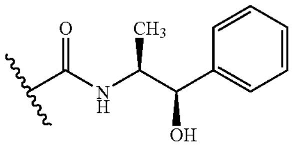 |

TABLE 1^A-continued
Compounds of Formula III-a
| No. III-a- | $R^3U_n$ | $T_mR^1$ | Q–$R^2$ |
|---|---|---|---|
| 168 | ethyl | methyl | 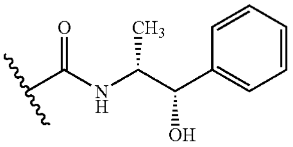 |
| 169 | ethyl | methyl | 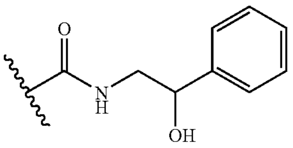 |
| 170 | ethyl | methyl | 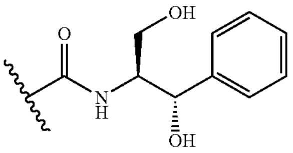 |
| 171 | ethyl | methyl | 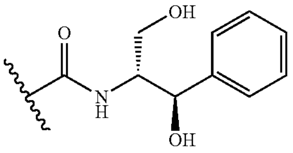 |
| 172 | ethyl | methyl | 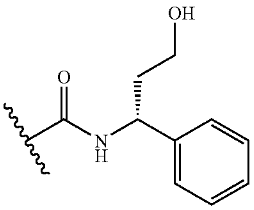 |
| 173 | ethyl | methyl | 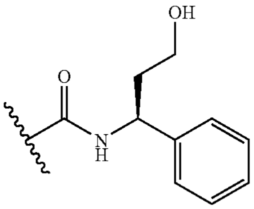 |
| 174 | 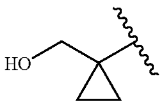 | methyl | 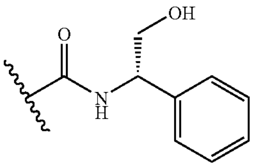 |
| 175 | $CH_2CH_2OH$ | methyl | 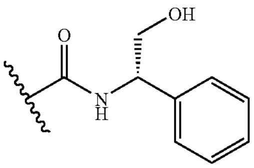 |

TABLE 1$^{A}$-continued
Compounds of Formula III-a
| No. III-a- | $R^3U_n$ | $T_mR^1$ | Q–$R^2$ |
|---|---|---|---|
| 176 | 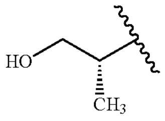 | methyl | 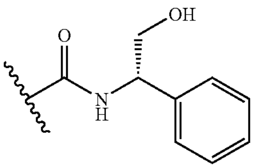 |
| 177 | 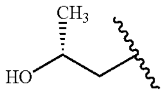 | methyl | 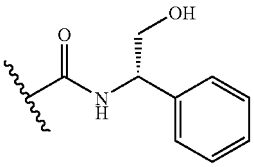 |
| 178 | 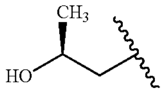 | methyl | 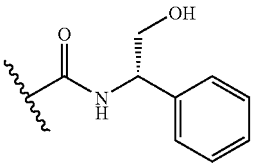 |
| 179 | 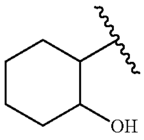 | methyl | 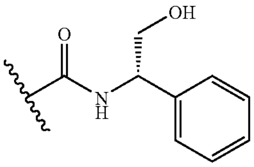 |
| 180 | H | H | 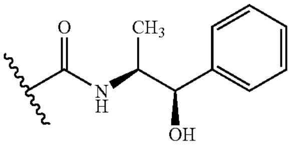 |
| 181 | H | H | 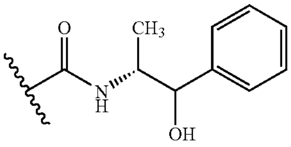 |
| 182 | H | H | 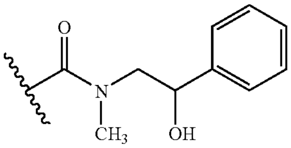 |
| 183 | H | H | 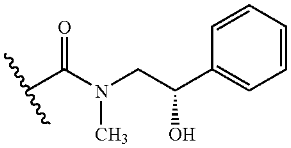 |

TABLE $1^A$-continued
| Compounds of Formula III-a | | | |
|---|---|---|---|
| No. III-a- | $R^3U_n$ | $T_mR^1$ | Q–$R^2$ |
| 184 | ethyl | methyl | 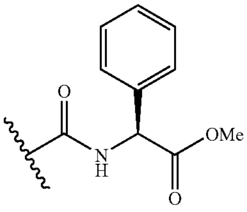 |
| 185 | H | H | 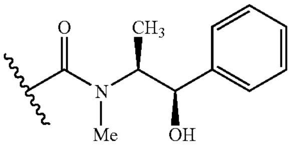 |
| 186 | H | H | 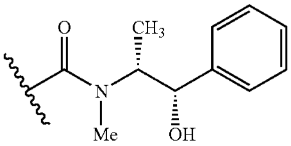 |
| 187 | ethyl | $CH_2OCH_3$ | 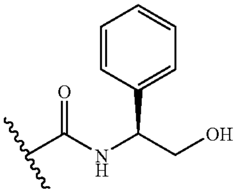 |
| 188 | ethyl | methyl | 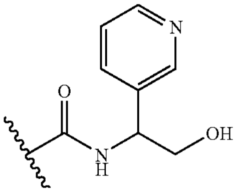 |
| 189 | ethyl | $CH_2OH$ | 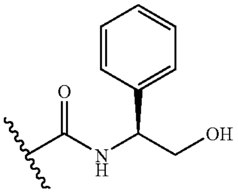 |
| 190 | ethyl | methyl | 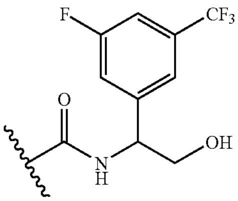 |

TABLE 1$^A$-continued
Compounds of Formula III-a
| No. III-a- | $R^3U_n$ | $T_mR^1$ | Q–$R^2$ |
| --- | --- | --- | --- |
| 191 | ethyl | methyl | 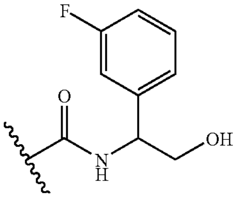 |
| 192 | ethyl | methyl | 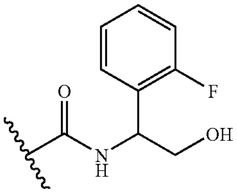 |
| 193 | 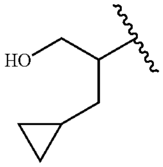 | methyl | 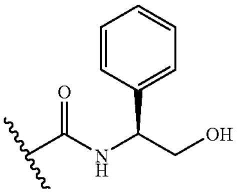 |
| 194 | 2,3-$Me_2$-phenyl | methyl | 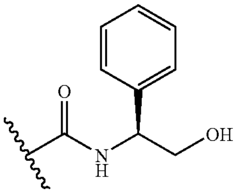 |
| 195 | $OCH_2CH_3$ | methyl | 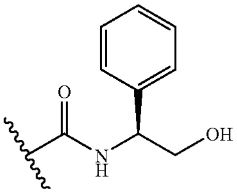 |
| 196 | 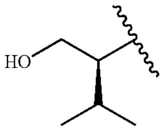 | methyl | 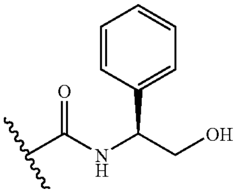 |
| 197 | ethyl | methyl | 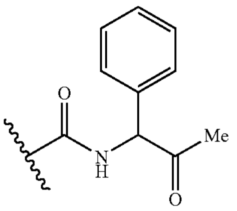 |

TABLE 1^A-continued
Compounds of Formula III-a
| No. III-a- | $R^3U_n$ | $T_mR^1$ | Q–$R^2$ |
| --- | --- | --- | --- |
| 198 | ethyl | methyl | 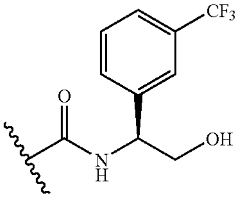 |
| 199 | 3-fluorophenyl | methyl | 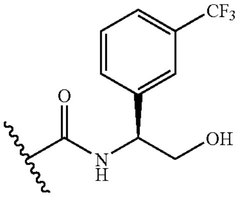 |
| 200 | 2-Cl-phenyl | methyl | 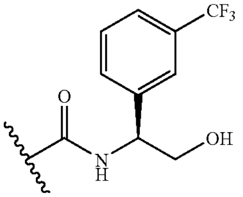 |
| 201 | 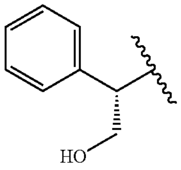 | methyl | 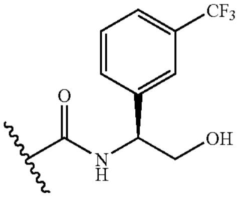 |
| 202 | cyclopropyl | methyl | 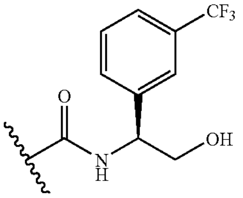 |
| 203 | cyclopropyl | methyl | 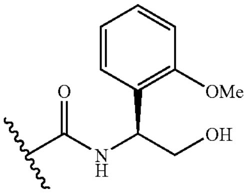 |
| 204 | cyclopropyl | methyl | 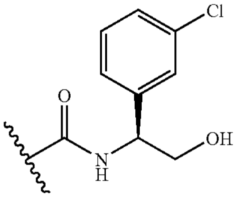 |

TABLE 1$^A$-continued
Compounds of Formula III-a
| No. III-a- | $R^3U_n$ | $T_mR^1$ | Q–$R^2$ |
|---|---|---|---|
| 205 | cyclopropyl | methyl | 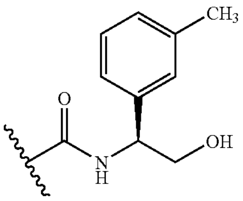 |
| 206 | O-Me | methyl | 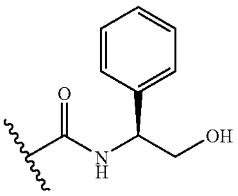 |
| 207 | O-isopropyl | methyl | 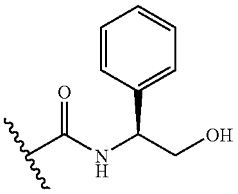 |
| 208 | 3-N(Me)$_2$-phenyl | methyl | 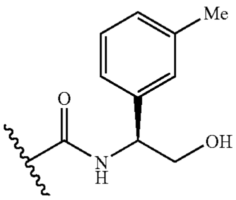 |
| 209 | 2-OH-phenyl | methyl | 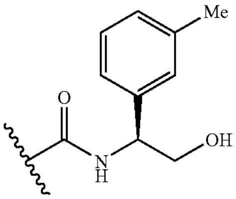 |
| 210 | 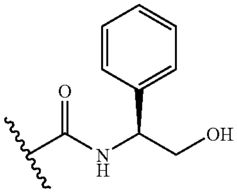 | methyl | 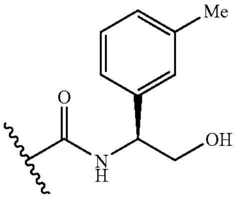 |
| 211 | 2,3-Me$_2$-phenyl | methyl | 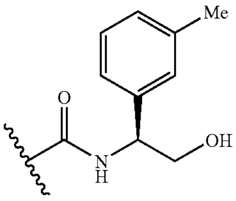 |

TABLE $1^A$-continued
Compounds of Formula III-a
| No. III-a- | $R^3U_n$ | $T_mR^1$ | Q–$R^2$ |
| --- | --- | --- | --- |
| 212 | 3-fluoro-phenyl | methyl | 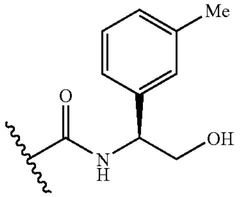 |
| 213 | acetyl | methyl | 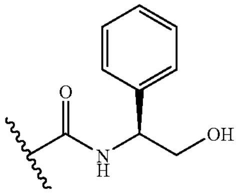 |
| 214 | 2-Me-phenyl | methyl | 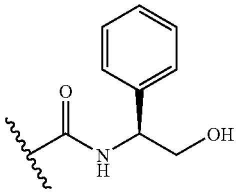 |
| 215 | pyridin-3-yl | methyl | 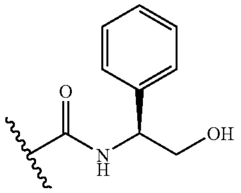 |
| 216 | 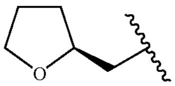 | methyl | 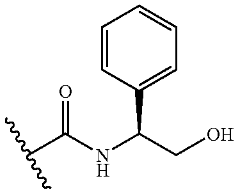 |
| 217 | 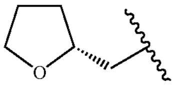 | methyl | 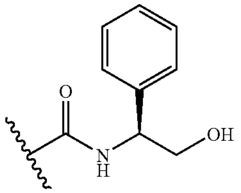 |
| 218 | NC(O)OEt | methyl | 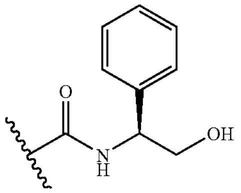 |

TABLE 1^A-continued
Compounds of Formula III-a
| No. III-a- | $R^3U_n$ | $T_mR^1$ | Q–$R^2$ |
|---|---|---|---|
| 219 | $CH_2$pyridin-3-yl | methyl | 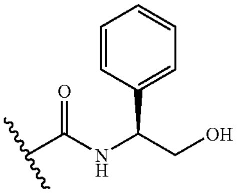 |
| 220 | 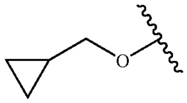 | methyl | 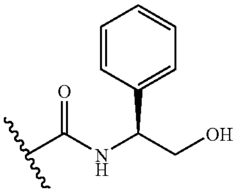 |
| 221 | isoxazol-3-yl | methyl | 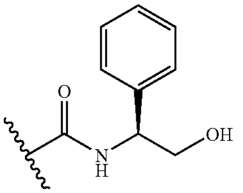 |
| 222 | 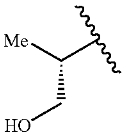 | methyl | 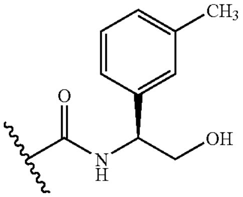 |
| 223 | 2-Me-phenyl | methyl | 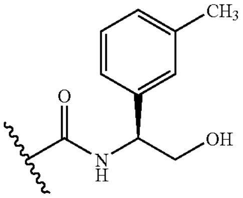 |
| 224 | 2-Me-phenyl | methyl | 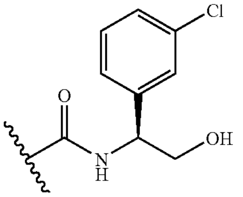 |
| 225 | $O(CH_2)_2OH$ | methyl | 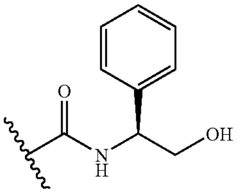 |

TABLE 1^A-continued
Compounds of Formula III-a
| No. III-a- | $R^3U_n$ | $T_mR^1$ | Q–$R^2$ |
|---|---|---|---|
| 226 | $N(Me)_2$ | methyl | 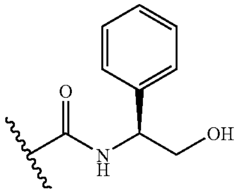 |
| 227 | 2-$CF_3$-phenyl | methyl | 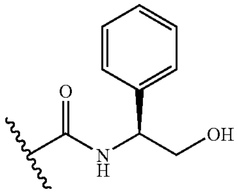 |
| 228 | 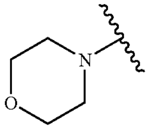 | methyl | 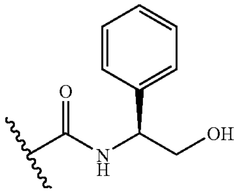 |
| 229 | 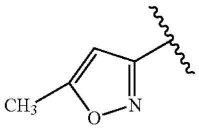 | methyl | 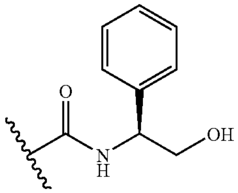 |
| 230 | 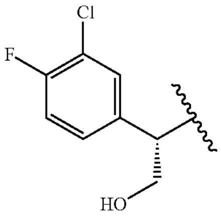 | methyl | 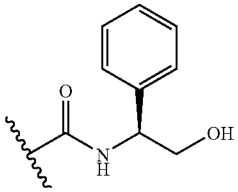 |
| 231 | phenyl | methyl | 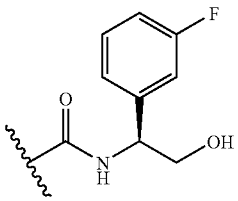 |
| 232 | 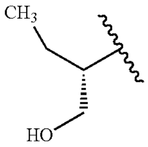 | methyl | 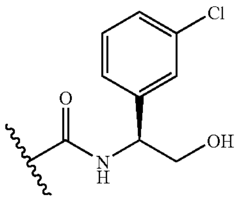 |

TABLE 1[A]-continued

Compounds of Formula III-a

| No. III-a- | $R^3U_n$ | $T_mR^1$ | Q–$R^2$ |
|---|---|---|---|
| 233 | 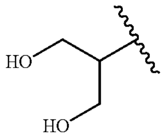 | methyl | 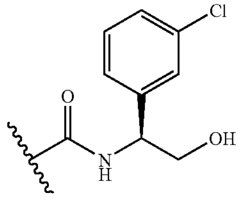 |
| 234 | 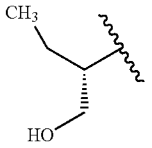 | methyl | 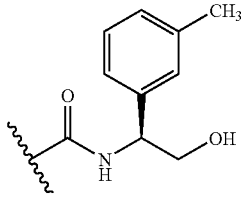 |
| 235 | 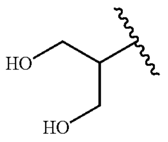 | methyl | 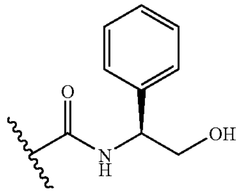 |
| 236 | 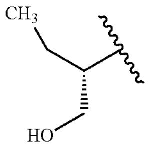 | methyl | 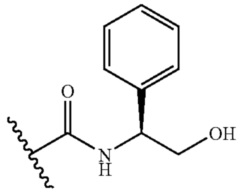 |
| 237 | 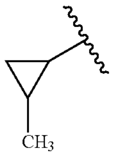 | methyl | 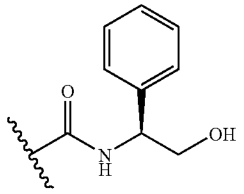 |
| 238 | CN | methyl | 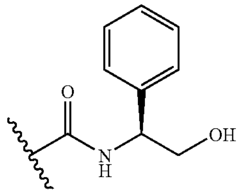 |

[A]Compound names for the compounds of formula III-a shown above in Table 1 are set forth in Appendix A.

The above formula III-a compounds are those wherein Ring A is a pyrimidine ring and Sp is a pyrrole ring. Inhibitors of formula I wherein Ring A is a pyridine, pyrimidine, or triazine ring having the other Sp rings shown above are otherwise structurally similar to the formula III-a compounds and are represented by the following general formulae II-b through II-j, III-b through III-j, and IV-b through IV-j shown below in Table 2;

TABLE 2
II-b
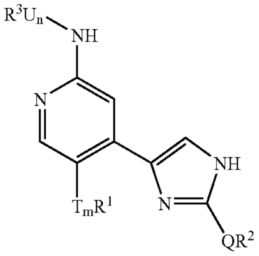
III-b
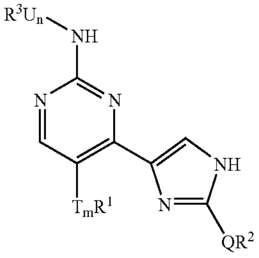
IV-b
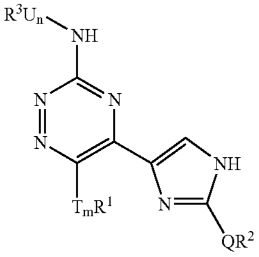
II-b'
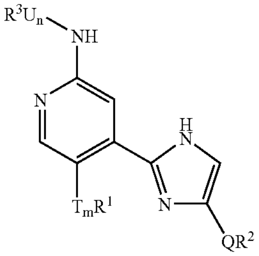
III-b'
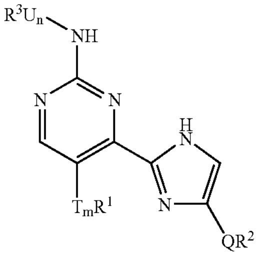
IV-b'
TABLE 2-continued
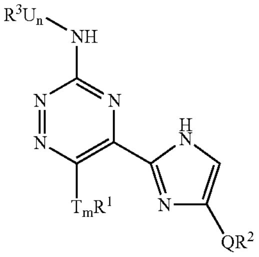
II-c
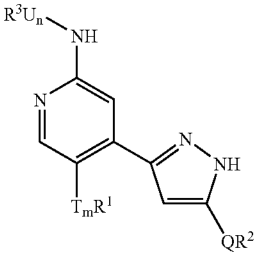
III-c
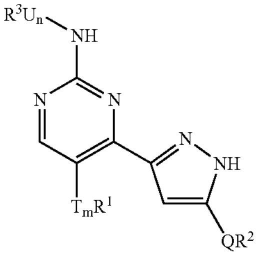
IV-c
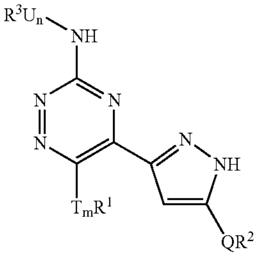
II-d
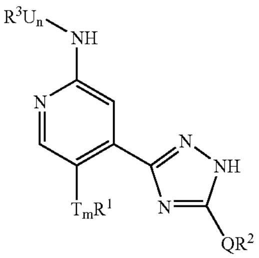
III-d TABLE 2-continued
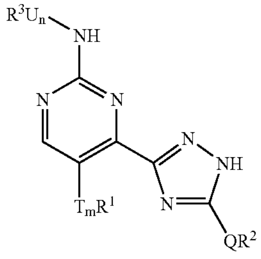
IV-d
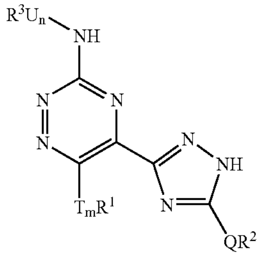
II-e
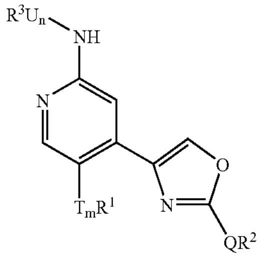
III-e
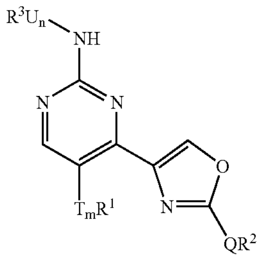
IV-e
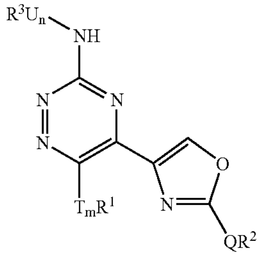
II-e'
TABLE 2-continued
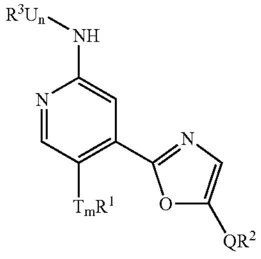
III-e'
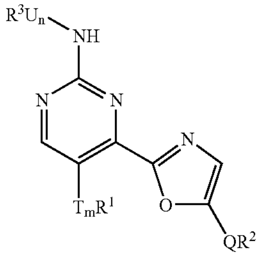
IV-e'
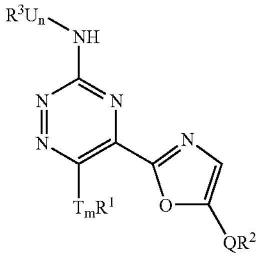
II-f
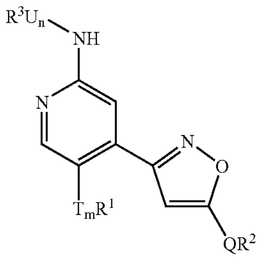
III-f
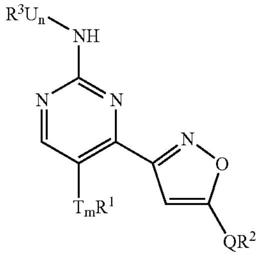
IV-f TABLE 2-continued
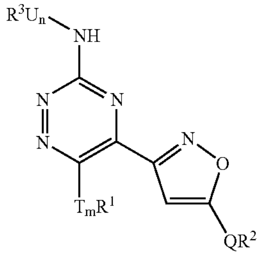
II-g
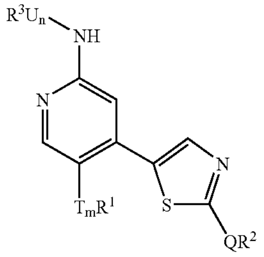
III-g
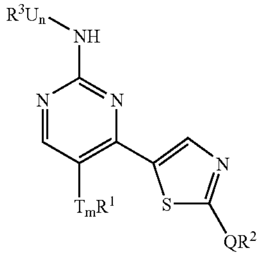
IV-g
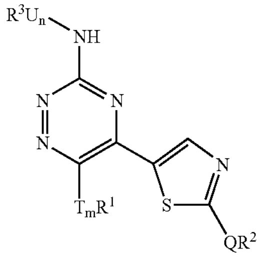
II-g'
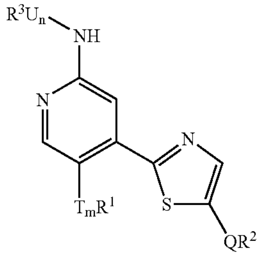
III-g'
TABLE 2-continued
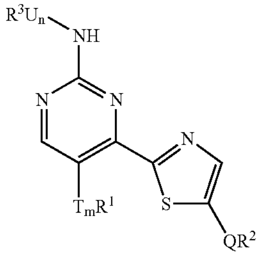
IV-g'
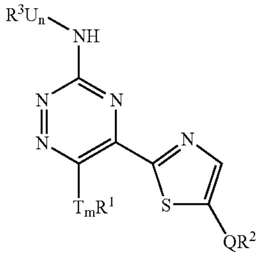
II-h
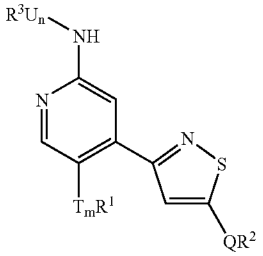
III-h
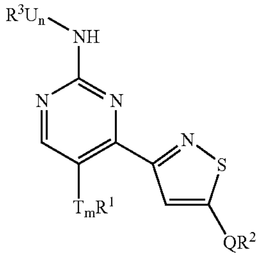
IV-h
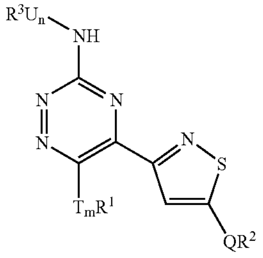
II-h'

TABLE 2-continued
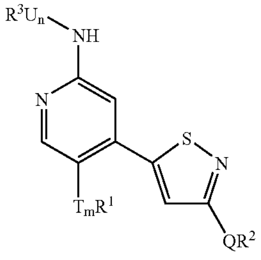
III-h'
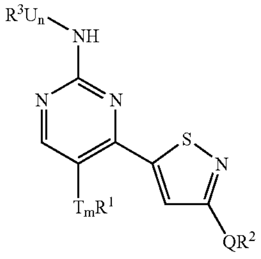
IV-h'
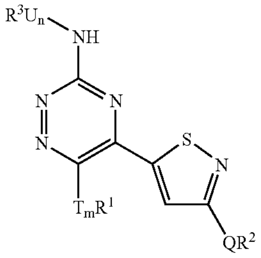
II-i
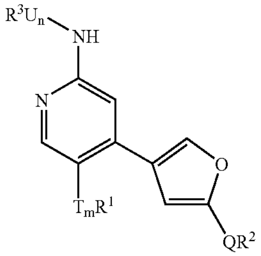
III-i
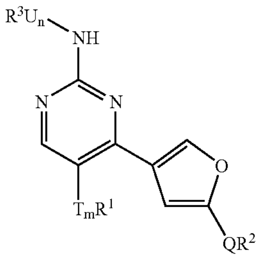
IV-i
TABLE 2-continued
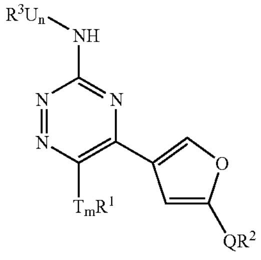
II-i'
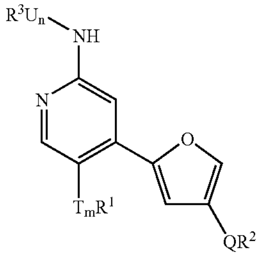
III-i'
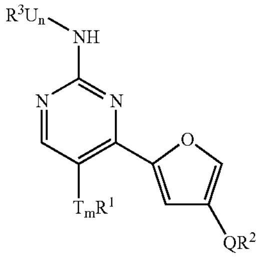
IV-i'
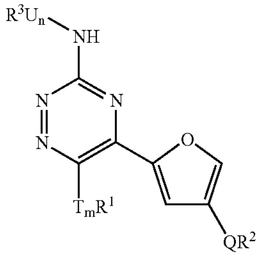
II-j
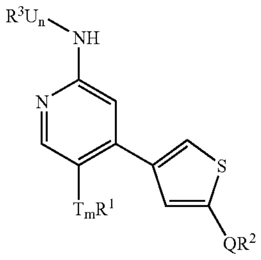
III-j TABLE 2-continued

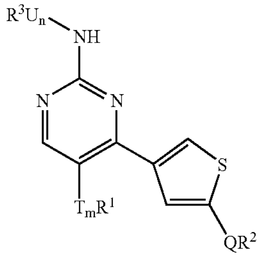

IV-j

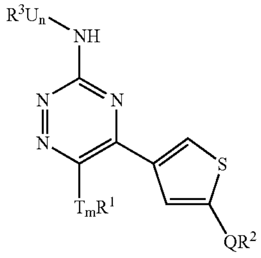

II-j'

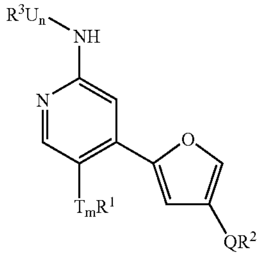

III-j'

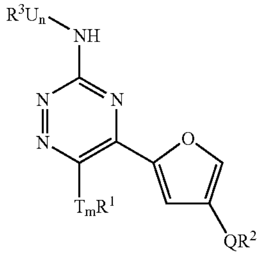

IV-j'

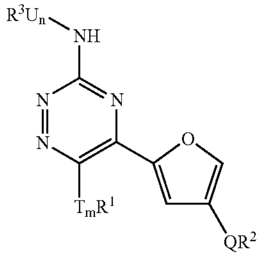

The compounds shown above in Table 2 are structurally similar to compounds of formula III-a where the pyrrole ring of formula III-a is replaced by each of the following Sp rings: imidazole (b), pyrazole (c), triazole (d), oxazole (e), isoxazole (f), 1,3-thiazole (g), 1,2-thiazole (h), furan (i), and thiophene (j). Accordingly, preferred $QR^2$, $T_mR^1$, and $U_nR^3$ groups of the compounds shown above in Table 2 are as described above for the formula III-a compounds.

In another embodiment, this invention provides a pharmaceutically acceptable composition comprising a compound shown above in Table 2 and a pharmaceutically acceptable carrier.

Another aspect of this invention relates to a method of treating or preventing an ERK2-mediated disease, which method comprises administering to a patient in need of such a treatment a therapeutically effective amount of a compound shown above in Table 2 or a pharmaceutically acceptable composition comprising said compound.

Another aspect of this invention relates to a method of inhibiting ERK2 activity in a patient, which method comprises administering to the patient a compound shown above in Table 2 or a pharmaceutically acceptable composition comprising said compound.

Another aspect of this invention relates to a method of treating or preventing an Aurora-2-mediated disease, which method comprises administering to a patient in need of such a treatment a therapeutically effective amount of a compound shown above in Table 2 or a pharmaceutically acceptable comprising said compound.

Another aspect of this invention relates to a method of inhibiting Aurora-2 activity in a patient, which method comprises administering to the patient a compound shown above in Table 2 or a pharmaceutically acceptable composition comprising said compound.

Another aspect of this invention relates to a method of treating or preventing a GSK-3-mediated disease, which method comprises administering to a patient in need of such treatment a therapeutically effective amount of a compound shown above in Table 2 or a pharmaceutically acceptable comprising said compound.

One aspect of this invention relates to a method of enhancing glycogen synthesis and/or lowering blood levels of glucose in a patient in need thereof, which method comprises administering to the patient a therapeutically effective amount of a compound shown above in Table 2 or a pharmaceutically acceptable composition comprising said compound. This method is especially useful for diabetic patients. Another method relates to inhibiting the production of hyperphosphorylated Tau protein, which is useful in halting or slowing the progression of Alzheimer's disease. Another method relates to inhibiting the phosphorylation of β-catenin, which is useful for treating schizophrenia.

Another aspect of this invention relates to a method of inhibiting GSK-3 activity in a patient, which method comprises administering to the patient a compound shown above in Table 2 or a pharmaceutically acceptable composition comprising said compound.

Another method relates to inhibiting ERK2, Aurora-2, or GSK-3 activity in a biological sample, which method comprises contacting the biological sample with a compound shown above in Table 2, or a pharmaceutically acceptable composition thereof, in an amount effective to inhibit ERK2, Aurora-2, or GSK-3.

Each of the aforementioned methods directed to the inhibition of ERK2, Aurora-2 or GSK-3, or the treatment of a disease alleviated thereby, is preferably carried out with a preferred compound shown above in Table 2, as described above.

The present compounds may be prepared in general by methods known to those skilled in the art for analogous compounds, as illustrated by the general Schemes I through XII and the synthetic examples shown below.

Scheme I

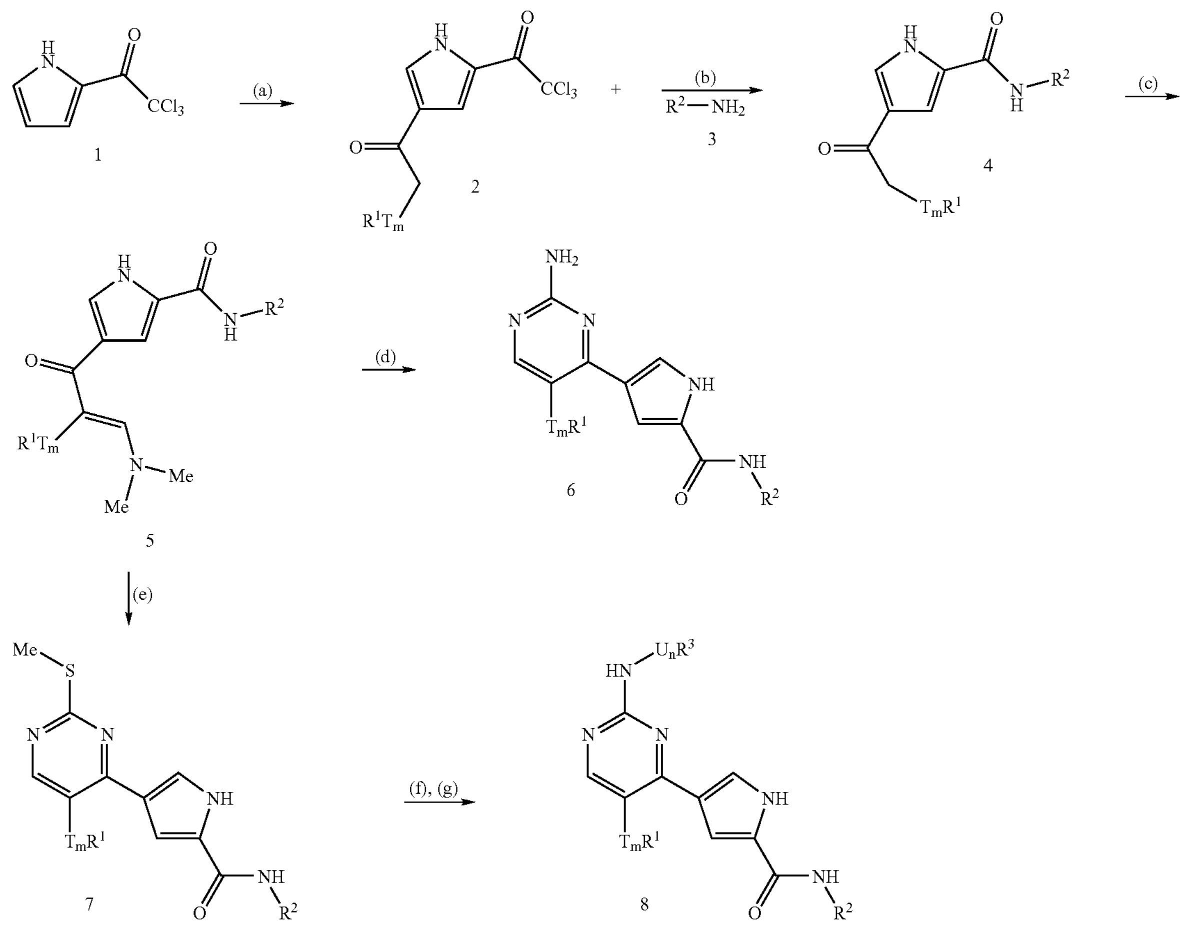

Reagents and conditions:
(a) T$_m$R$^1$CH$_2$COCl, AlCl$_3$, CH$_2$Cl$_2$, 2 hours, RT;
(b) DMF, 24 hrs, room temperature;
(c) (Me$_2$N)$_2$—CHOt-Bu, THF, 24 hrs, room temperature;
(d) guanidine, EtOH, 12 hours, reflux;
(e) thiourea, EtOH, K$_2$CO$_3$, 12 hrs reflux;
(f) m-CPBA, EtOH;
(g) U$_n$R$^3$—NH$_2$, DMSO, 130° C.

Scheme I above shows a general synthetic route that is used for preparing the pyrrol-3-yl compounds of formula III-a of this invention when R$^2$ is an optionally substituted phenyl group or aliphatic group. In step (a), an optionally substituted acid chloride is combined with compound 1, dichloromethane, and aluminum; trichloride to form compound 2. In cases where benzoyl acid chlorides are used, a wide variety of substituents on the phenyl ring are amenable to this reaction. Aliphatic acid chlorides are also used in many cases. Examples of suitable R$^2$ groups include, but are not limited to, those set forth in Table 1 above.

The formation of amide 4 is achieved by treating compound 2 with an amine 3 in DMF. When amine 3 is a primary amine, the reaction proceeds at ambient temperature. When amine 3 is a secondary amine, the reaction is heated at 50° C. to achieve complete reaction and afford amide 4.

The formation of enamine 5 at step (c) is achieved by treating amide 4 with (Me$_2$N)$_2$-CHOt-Bu at ambient temperature. Alternatively, the reaction to form enamine 5 at step (c) is also achieved by using dimethylformamide-dimethylacetal (DMF-DMA). The reaction using DMF-DMA typically requires elevated temperature to afford enamine 5 whereas using (Me$_2$N)$_2$-OtBu has the advantage of proceeding at ambient temperature to afford the enamine 5 in higher purity.

The formation of the pyrimidine compound 6 at step (d) is achieved by the treatment of enamine 5 with guanidine at elevated temperature. Alternatively, use of a substituted guanidine results in an amino substituent as is illustrated by 8.

As an alternative method, in step (e) intermediate 5 may be cyclized with S-methyl thiourea to form the 2-thiomethylpyrimidine 7 which may in turn be oxidized with m-CPBA to the sulfone. The sulfonyl group may be subsequently displaced by an amine to generate the substituted aminopyrimidine 8.

The compounds of formula III-a synthesized by this method, as exemplified in Table 1, were isolated by preparatory HPLC (reverse phase, 10→90% MeCN in water over 15 minutes). The details of the conditions used for producing these compounds are set forth in the Examples.

Scheme II

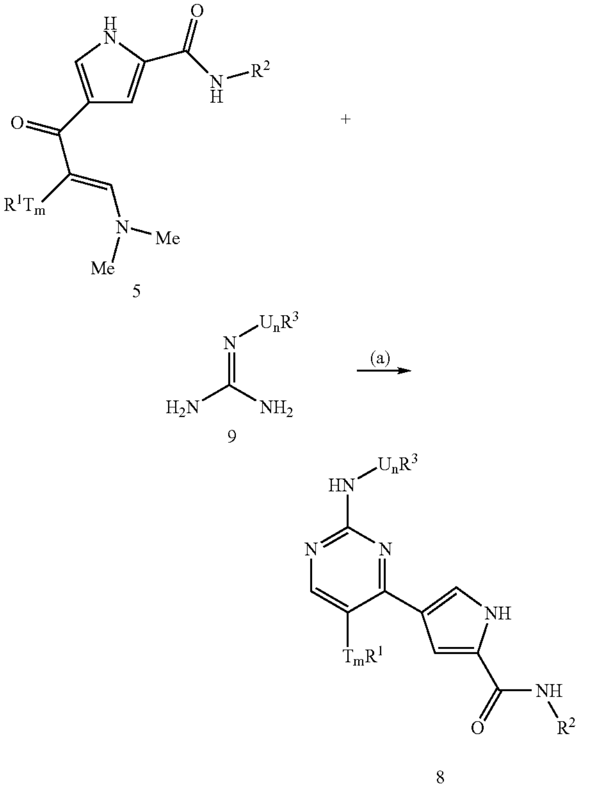

Reagents and conditions: (a) $K_2CO_3$, DMA, 100° C.

Scheme II above shows a general method for preparing compounds 8 from intermediate 5 and an N-substituted guanidine (9). Intermediate 5 may be prepared according to Scheme I steps (a), (b), and (c) shown above. Compound 5 is treated with N-substituted guanidine (9) and potassium carbonate in dimethylacetamide to form compound 8. This reaction is amenable to a variety of N-substituted guanidines to form compounds of formula III-a. The details of the conditions used for producing these compounds are set forth in the Examples.

Scheme III

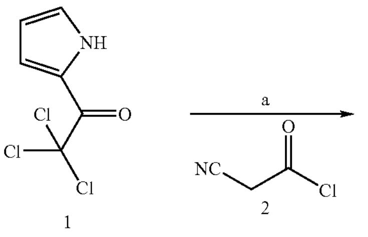

-continued

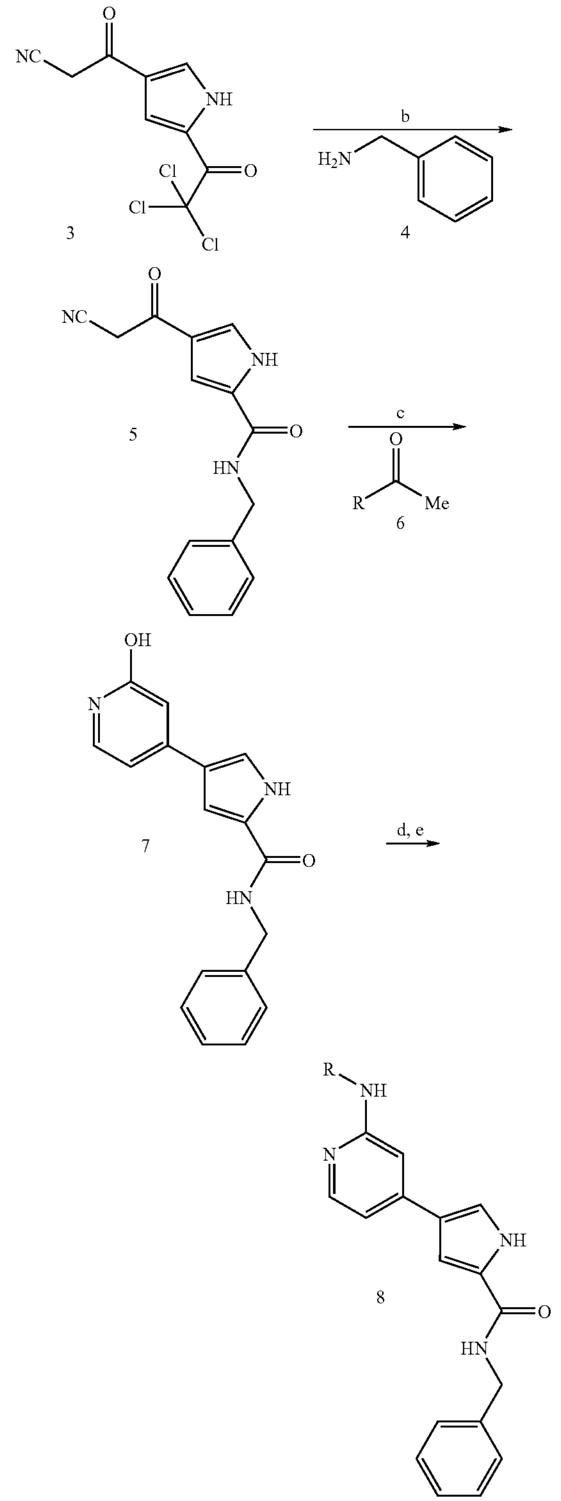

Reagents and conditions:
(a) $AlCl_3$ neat, RT; (b) DMF, 24 hrs, room temperature; (c) polyphosphoric acid, 1 hour, 25-140° C.; (d) $POCl_3$, DMF, reflux; (e) $NH_2$—$U_nR^3$, iPrOH, reflux.

Scheme III above shows a general synthetic route that may be used for preparing the pyrrol-3-yl compounds of formula II-a of this invention. The conversion of intermediate 5 to product 8 may be achieved through steps (c), (d), and (e) according to the method described in JACS, 1957, pp 79.

Scheme IV

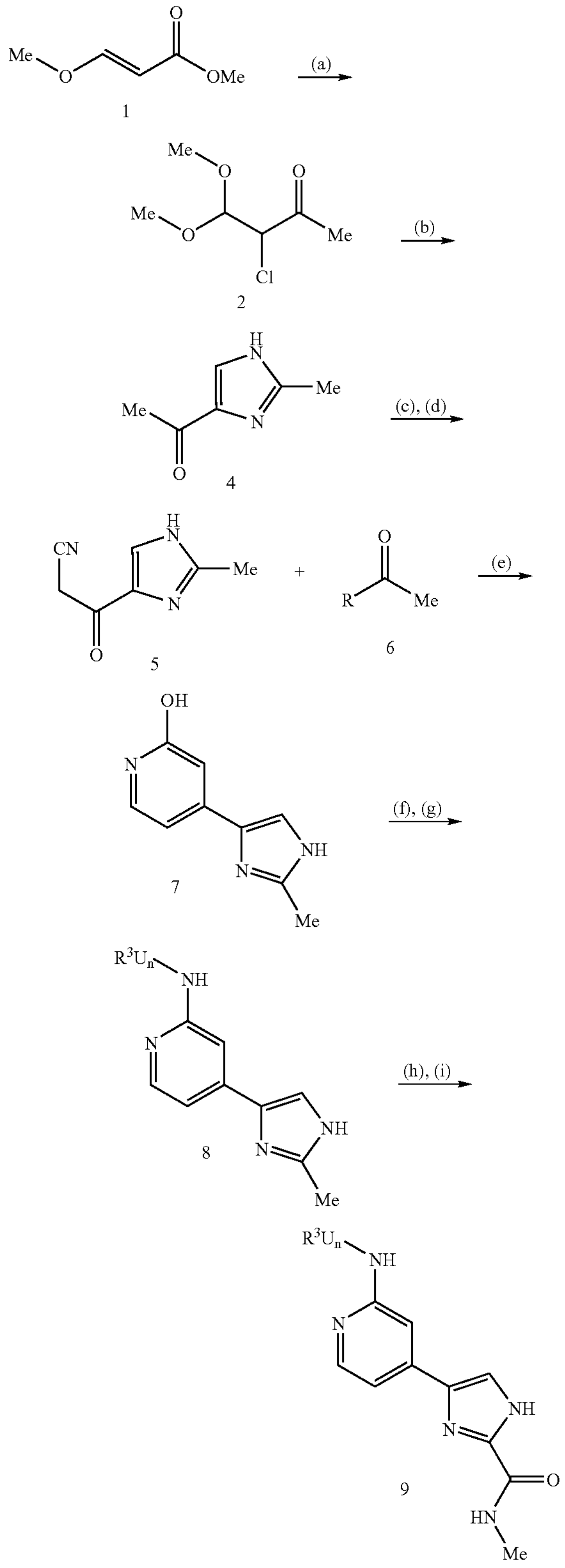

-continued

Reagents and conditions:
(a) MeOH, pyridine, $Cl_2$; (b) guanidine; (c) bromine, acetic acid;
(d) NaCN, DMF; (e) 6, polyphosphoric acid, 1 hour, 25–140° C.;
(f) $POCl_3$, DMF, reflux; (g) $NH_2$—$U_nR^3$, iPrOH, reflux; (h) $SeO_2$;
(i) MeNH.

Scheme IV above shows a general synthetic route that may be used for preparing the imidazol-4-yl compounds of formula II-b of this invention. The conversion of intermediate 5 to product 8 may be achieved through steps (e), (f), and (g) according to the method described in JACS, 1957, pp 79.

Scheme V

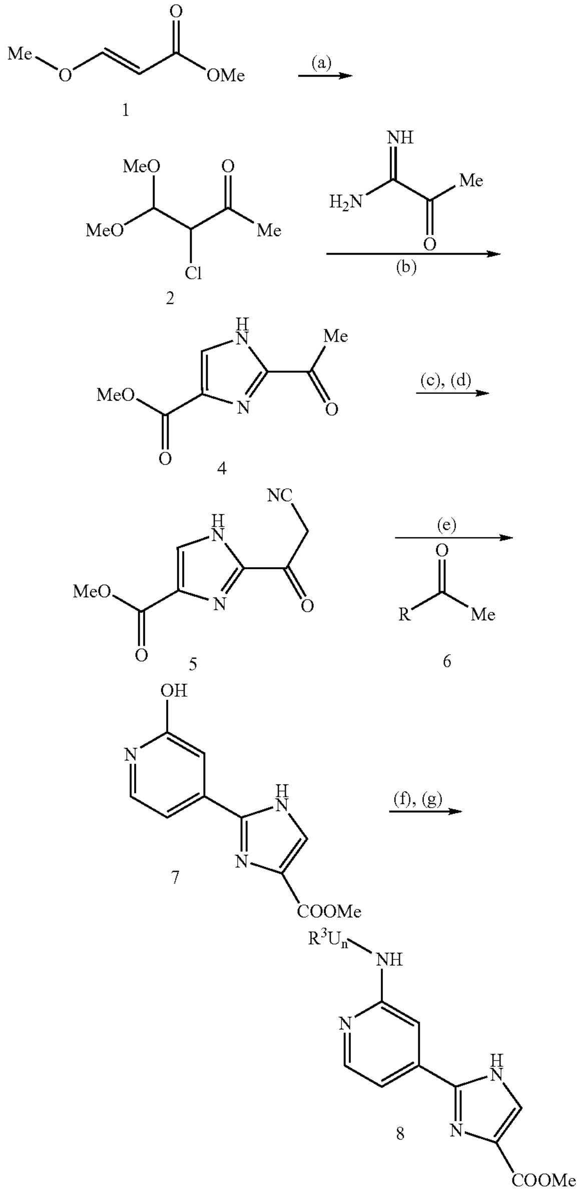

Reagents and conditions:
(a) MeOH, pyridine, $Cl_2$; (b) 3; (c) bromine, acetic acid;
(d) NaCN, DMF; (e) 6, polyphosphoric acid, 1 hour, 25–140° C.;
(f) $POCl_3$, DMF, reflux; (g) $NH_2$—$U_nR^3$, iPrOH, reflux.

Scheme V above shows a general synthetic route that may be used for preparing the imidazol-2-yl compounds of formula II-b' of this invention. The conversion of intermediate 5 to product 8 may be achieved through steps (e), (f), and (g) according to the method described in JACS, 1957, pp 79.

Scheme VI

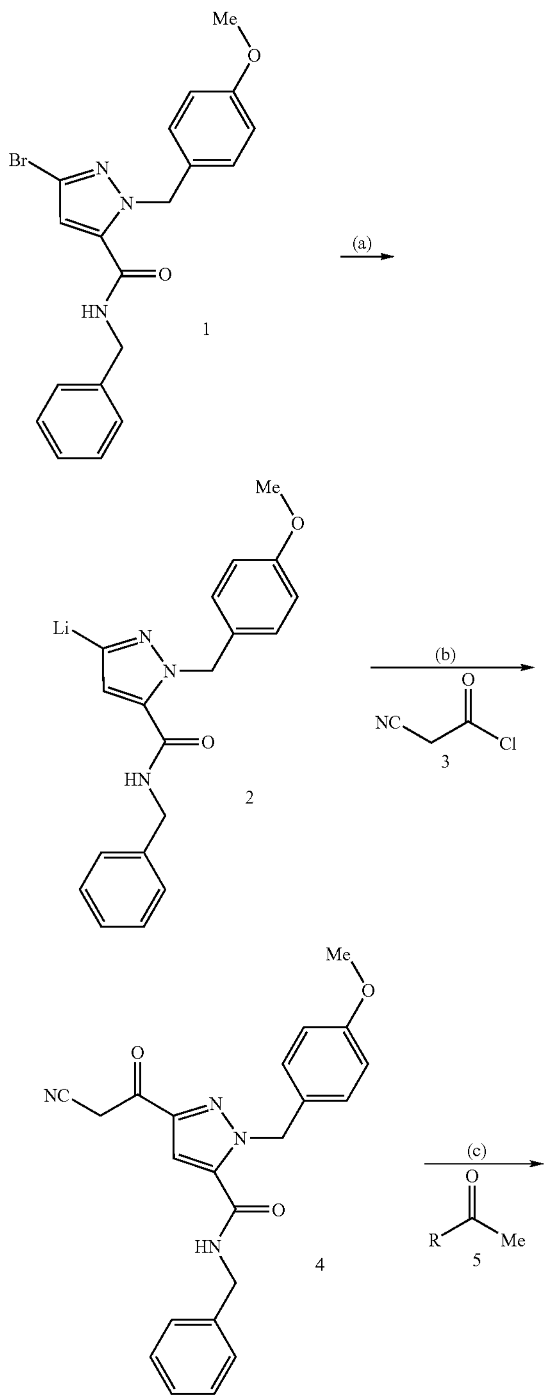

1

2

3

4

5

-continued

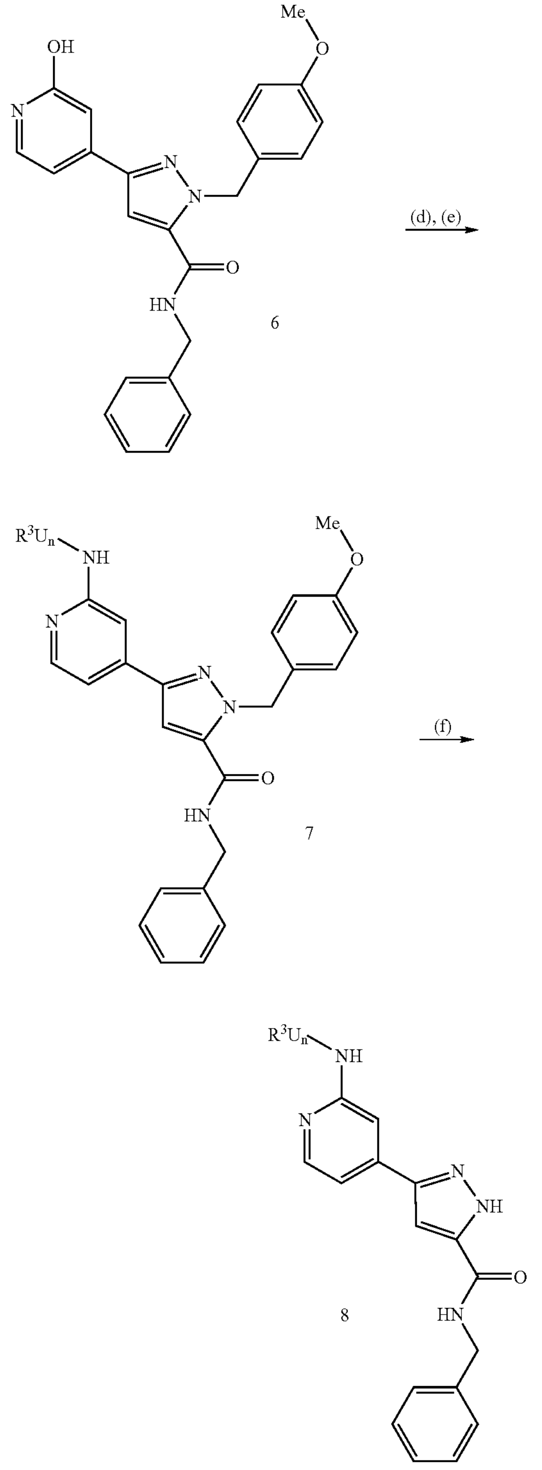

6

7

8

Reagents and conditions:
(a) (b) 3; (c) 5, polyphosphoric acid, 1 hour, 25-140° C.;
(d) $POCl_3$, DMF, reflux; (e) $NH_2$—$U_nR^3$, iPrOH, reflux;
(f) ceric ammonium nitrate.

Scheme VI above shows a general synthetic route that may be used for preparing the pyrazol-3-yl compounds of formula II-c of this invention. The conversion of intermediate 4 to product 7 may be achieved through steps (c), (d), and (e) according to the method described in JACS, 1957, pp 79.

Scheme VII

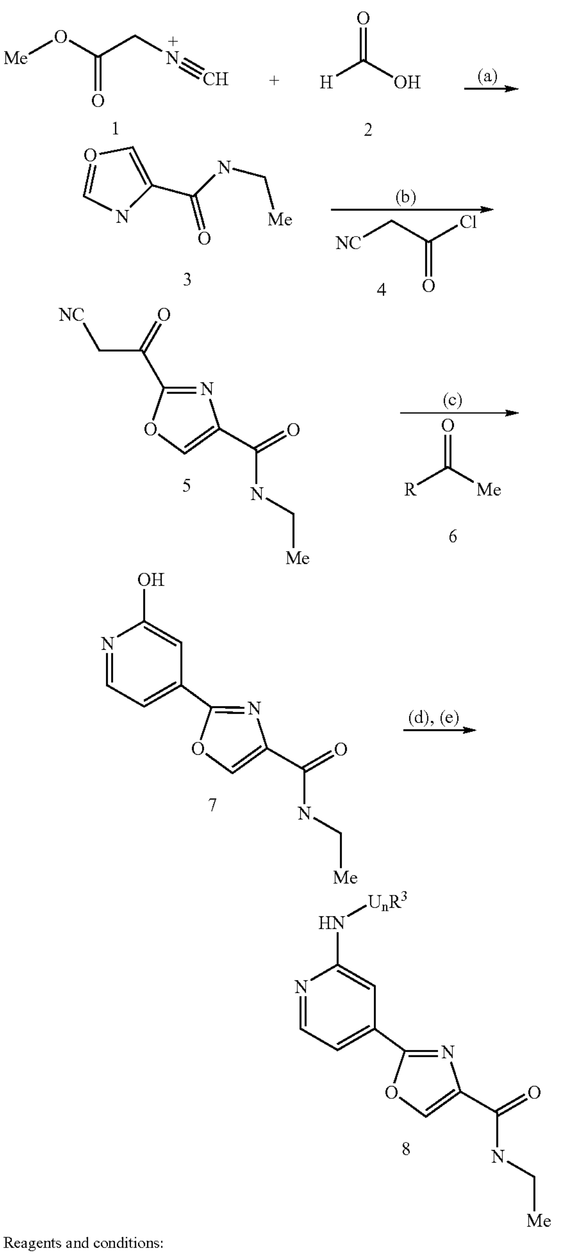

Reagents and conditions:
(a) 1,1′-carbonyldiimidazole (CDI), triethylamine, THF;
(b) N-butyllithium, THF, -78° C.; (c) 6, polyphosphoric acid, 1 hour, 25-140° C.; (d) $POCl_3$, DMF, reflux; (e) $NH_2$—$U_nR^3$, iPrOH, reflux.

Scheme VII above shows a general synthetic route that may be used for preparing the oxazol-2-yl-compounds of formula II-e' of this invention. The conversion of intermediate 5 to product 8 may be achieved through steps (c), (d), and (e) according to the method described in JACS, 1957, pp 79.

Scheme VIII

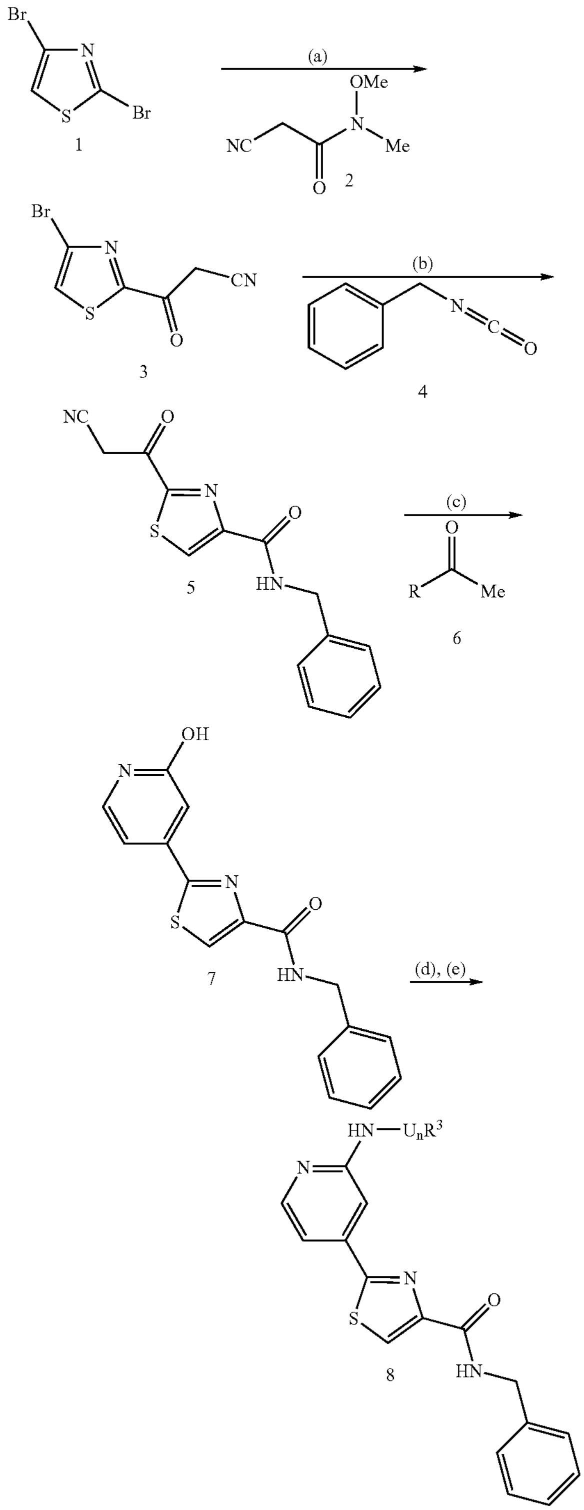

Reagents and conditions:
(a) N-butyllithium, TMEDA, -78° C. (c) 6, polyphosphoric acid, 1 hour, 25-140° C. (d) $POCl_3$, DMF, reflux (e) $NH_2$—R, iPrOH, reflux.

Scheme VIII above shows a general synthetic route that may be used for preparing the thiazol-2-yl compounds of formula II-g' of this invention. The conversion of intermediate 5 to product 8 may be achieved through steps (c), (d), and (e) according to the method described in JACS, 1957, pp 79.

Scheme IX

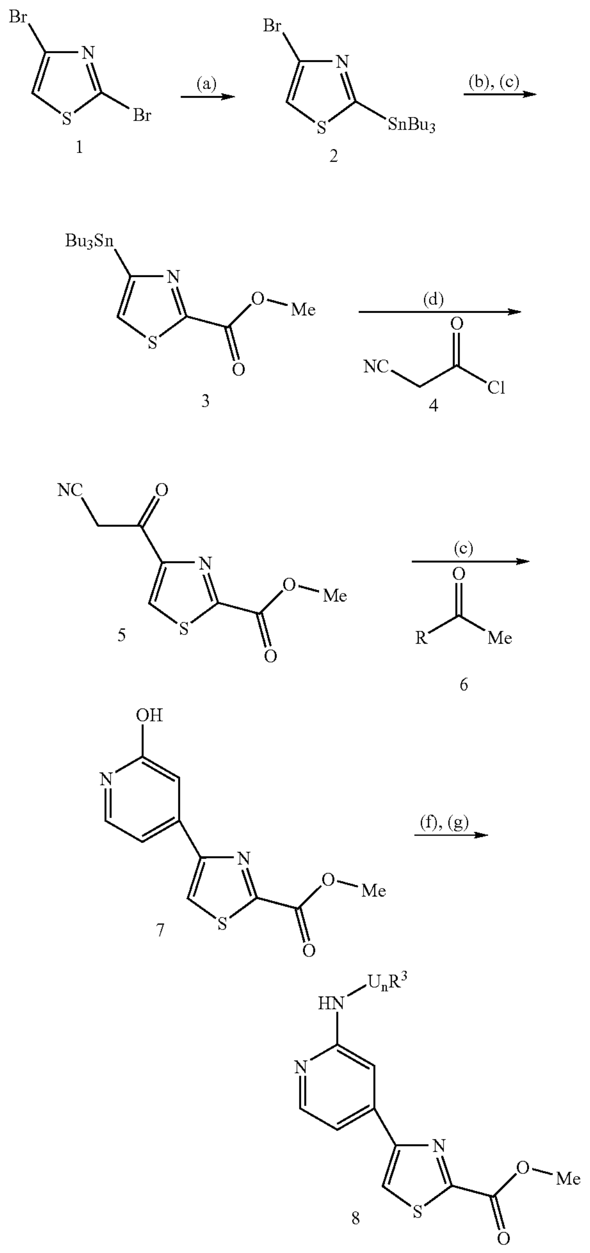

Reagents and conditions:
(a) N-butyllithium, $Bu_3SnCl$; (b) t-butyllithium, THF, -78° C.; (c) $MeOCO_2Me$; (d) 4, Pd(0); (e) 6, polyphosphoric acid, 1 hour, 25-140° C.; (f) $POCl_3$, DMF, reflux; (g) $NH_2$—$U_nR^3$, iPrOH, reflux.

Scheme IX above shows a general synthetic route that may be used for preparing the thiazol-4-yl compounds of formula II-g of this invention. The conversion of intermediate 5 to product 8 may be achieved through steps (e), (f), and (g) according to the method described in JACS, 1957, pp 79.

Scheme X

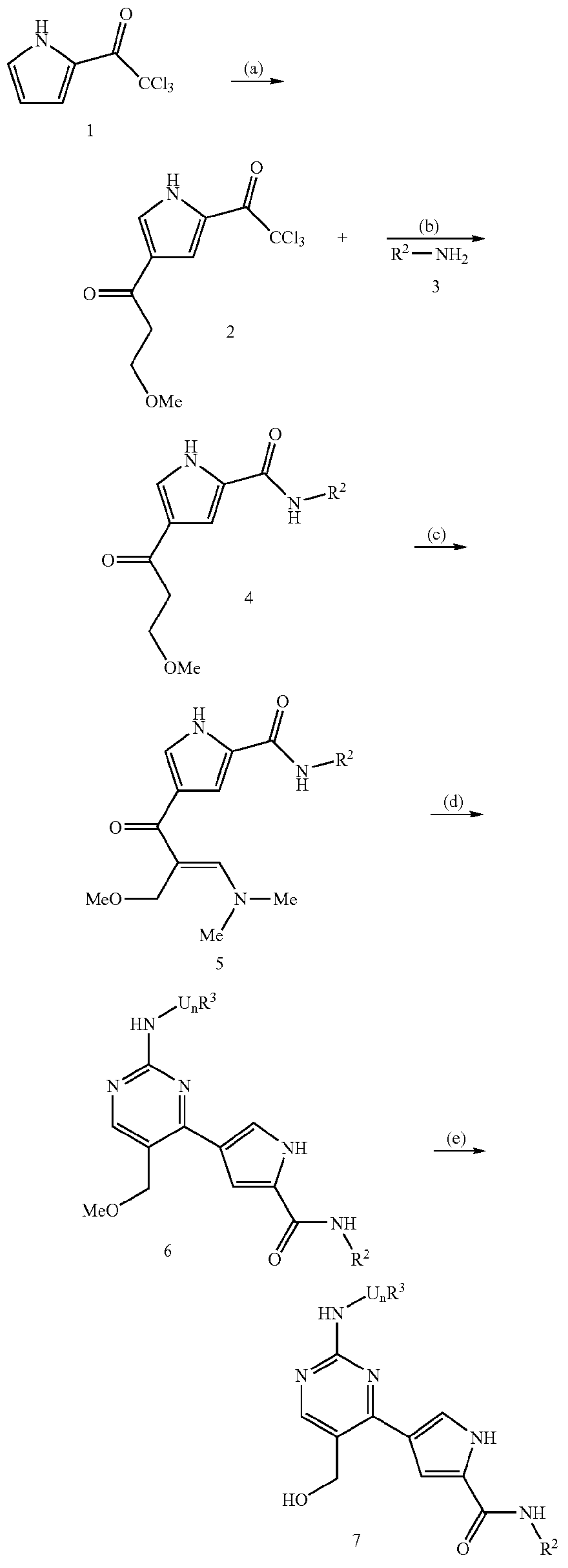

-continued

Reagents and conditions:
(a) $CH_3OCH_2CH_2COCl$, $AlCl_3$, $CH_2Cl_2$, 2.5 hours, RT;
(b) DMF, 24 hrs, room temperature; (c) $(Me_2N)_2$—CHOt-Bu, THF, 24 hrs, room temperature; (d) N-substituted guanidine, EtOH, 12 hours, reflux; (e) $BBr_3$, $CH_2Cl_2$, $Na_2CO_3$.

Scheme X above shows a general synthetic route that is used for preparing compounds of formula III-a where $T_mR^1$ is methoxymethyl or hydroxymethyl. In step (a), 3-methoxypropionyl chloride is combined with compound 1, dichloromethane, and aluminum trichloride to form compound 2.

The formation of amide 4 is achieved by treating compound 2 with an amine 3 in DMF. When amine 3 is a primary amine, the reaction proceeds at ambient temperature. When amine 3 was a secondary amine, the reaction is heated at 50° C. to achieve complete reaction and afford amide 4. The formation of enamine 5 at step (c) is achieved by treating amide 4 with $(Me_2N)_2$-CHOt-Bu at ambient temperature.

The formation of the pyrimidine compound 6 at step (d) is achieved by the treatment of enamine 5 with a guanidine at elevated temperature. Alternatively, use of a substituted guanidine results in an amino substituent.

To form compounds where $T_mR^1$ is hydroxymethyl, intermediate 6 may be treated with $BBr_3$ in dichloromethane to form compounds 7. One of skill in the art would recognize that the hydroxymethyl group of compound 7 could be further derivatized to form a variety of compounds of formula III-a. The details of the conditions used for producing these compounds are set forth in the Examples.

Scheme XI

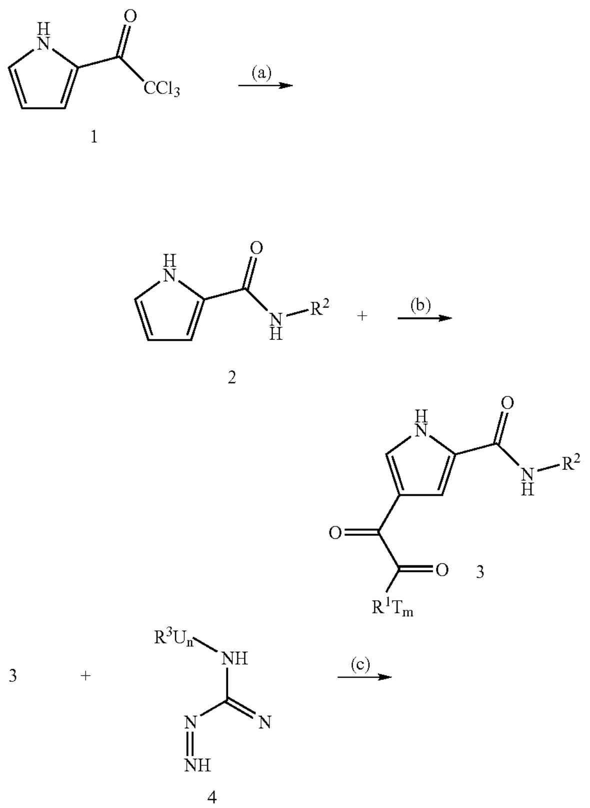

1

2

3

4

-continued

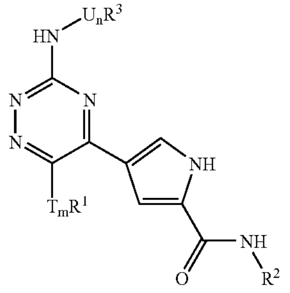

IV-a

Reagent and conditions:
(a) $R^2NH_2$, MeCN, 0° C. to 25° C., 12 hours;
(b) $AlCl_3$, $CH_2Cl_2$, 25° C.; (c) MeOH:$H_2O$ (2:1), 37° C.

Scheme XI above shows a general method for preparing the triazine compounds of formula IV-a. Step (a) is performed in the manner described at Scheme I, step (b) above. Step (b) is performed in the manner described at Scheme I, step (a) above. The formation of the triazine ring at step (c) may be performed according to the methods described by Hirsch, J.; Petrakova, E.; Feather, M. S.; *J Carbohydr Chem* [JCACDM] 1995, 14 (8), 1179-1186. Alternatively, step (c) may be performed according to the methods described by Siddiqui, A. U.; Satyanarayana, Y.; Rao, U. M.; Siddiqui, A. H.; *J Chem Res, Synop* [JRPSDC] 1995 (2), 43.

Scheme XII

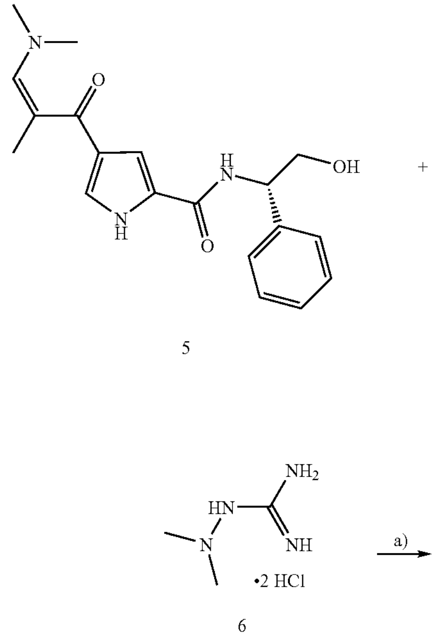

5

6

-continued

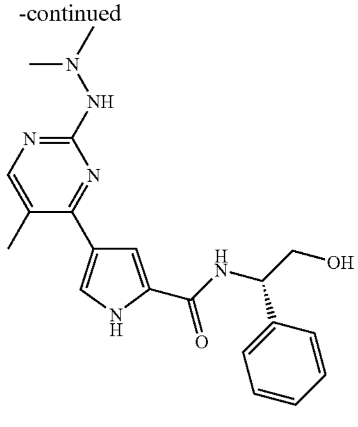

III-a-226

Reagents and conditions:
(a) $K_2CO_3$, DMA, 100° C., 24 hrs.

Using the preparation of compound III-a-226 to illustrate, Scheme XII above shows a general synthetic route that is used for preparing compounds of formula III-a where $U_n$ is $NR^7$. The formation of the pyrimidine compound III-a-226 at step (a) is achieved by the treatment of enamine 5 with a guanidine 6 at elevated temperature. Alternatively, use of a substituted amino guanidine results in an hydrazyno substituent.

In another embodiment, this invention provides a pharmaceutically acceptable composition comprising a compound of formula I', I", I°, III-a, III-a', or III-a°, and a pharmaceutically acceptable carrier.

Another aspect of this invention relates to a method of treating or preventing an ERK2-mediated disease, which method comprises administering to a patient in need of such a treatment a therapeutically effective amount of compound of formula I', I", III-a, III-a', or III-a°, or a pharmaceutically acceptable composition comprising said compound.

Another aspect of this invention relates to a method of inhibiting ERK2 activity in a patient, which method comprises administering to the patient compound of formula I', I", I°, III-a, III-a', or III-a°, or a pharmaceutically acceptable composition comprising said compound.

Another aspect of this invention relates to a method of treating or preventing an Aurora-2-mediated disease, which method comprises administering to a patient in need of such a treatment a therapeutically effective amount of a compound of formula I', I", I°, III-a, III-a', or III-a°, or a pharmaceutically acceptable composition comprising said compound.

Another aspect of this invention relates to a method of inhibiting Aurora-2 activity in a patient, which method comprises administering to the patient a compound of formula I', I", I°, III-a, III-a', or III-a°, or a pharmaceutically acceptable composition comprising said compound.

Another aspect of this invention relates to a method of treating or preventing a GSK-3-mediated disease, which method comprises administering to a patient in need of such treatment a therapeutically effective amount of a compound of formula I', I", I°, III-a, III-a', or III-a°, or a pharmaceutically acceptable composition comprising said compound.

One aspect of this invention relates to a method of enhancing glycogen synthesis and/or lowering blood levels of glucose in a patient in need thereof, which method comprises administering to the patient a therapeutically effective amount of a compound of formula I', I", I°, III-a, III-a', or III-a°, or a pharmaceutically acceptable composition comprising said compound. This method is especially useful for diabetic patients. Another method relates to inhibiting the production of hyperphosphorylated Tau protein, which is useful in halting or slowing the progression of Alzheimer's disease. Another method relates to inhibiting the phosphorylation of β-catenin, which is useful for treating schizophrenia.

Another aspect of this invention relates to a method of inhibiting GSK-3 activity in a patient, which method comprises administering to the patient a compound of formula I', I", I°, III-a, III-a', or III-a°, or a pharmaceutically acceptable composition comprising said compound.

Another aspect of this invention relates to a method of treating or preventing a CDK-2-mediated disease, which method comprises administering to a patient in need of such a treatment a therapeutically effective amount of a compound of formula I', I", I°, III-a, III-a', or III-a°, or a pharmaceutically acceptable composition comprising said compound.

The term "CDK-2-mediated condition" or "disease", as used herein, means any disease or other deleterious condition in which CDK-2 is known to play a role. The term "CDK-2-mediated condition" or "disease" also means those diseases or conditions that are alleviated by treatment with a CDK-2 inhibitor. Such conditions include, without limitation, cancer, Alzheimer's disease, restenosis, angiogenesis, glomerulonephritis, cytomegalovirus, HIV, herpes, psoriasis, atherosclerosis, alopecia, and autoimmune diseases such as rheumatoid arthritis. See Fischer, P. M. and Lane, D. P., *Current Medicinal Chemistry*, 7; 1213-1245 (2000); Mani, S., Wang, C., Wu, K., Francis, R. and Pestell,. R., *Exp. Opin. Invest. Drugs*, 9, 1849 (2000); Fry, D. W. and Garrett, M. D., *Current Opinion in Oncologic, Endocrine & Metabolic Investigational Drugs*, 2, 40-59 (2000).

Another aspect of this invention relates to a method of treating or preventing a Lck-mediated disease, which method comprises administering to a patient in need of such a treatment a therapeutically effective amount of a compound of formula I', I", I°, III-a, III-a', or III-a°; or a pharmaceutically acceptable composition comprising said compound.

The terms "Lck-mediated disease" or "Lck-mediated condition", as used herein, mean any disease state or other deleterious condition in which Lck is known to play a role. The terms "Lck-mediated disease" or "Lck-mediated condition" also mean those diseases or conditions that are alleviated by treatment with an Lck inhibitor. Lck-mediated diseases or conditions include, but are not limited to, autoimmune diseases such as transplant rejection, allergies, rheumatoid arthritis, and leukemia. The association of Lck with various diseases has been described [Molina et al., *Nature*, 357, 161 (1992)].

Another aspect of this invention relates to a method of treating or preventing an AKT3-mediated disease, which method comprises administering to a patient in need of such a treatment a therapeutically effective amount of a compound of formula I', I", I°, III-a, III-a', or III-a°, or a pharmaceutically acceptable composition comprising said compound.

The terms "AKT3-mediated disease" or "AKT3-mediated condition", as used herein, mean any disease state or other deleterious condition in which AKT3 is known to play a role. The terms "AKT3-mediated disease" or "AKT3-mediated condition" also mean those diseases or conditions that are alleviated by treatment with an AKT inhibitor. AKT3- mediated diseases or conditions include, but are not limited to, proliferative disorders, cancer, and neurodegenerative disorders. The association of AKT3 with various diseases has been described [Zang, Q. Y., et al, *Oncogene*, 19 (2000)] and [Kazuhiko, N., et al, The *Journal of Neuroscience*, 20 (2000)].

Another method relates to inhibiting ERK2, Aurora-2, CDK-2, Lck, AKT3, or GSK-3 activity in a biological sample, which method comprises contacting the biological sample with a compound of formula I', I", I°, III-a, III-a', or III-a°, or a pharmaceutically acceptable composition comprising said compound, in an amount effective to inhibit ERK2, Aurora-2, CDK-2, Lck, AKT3, or GSK-3.

Each of the aforementioned methods directed to the inhibition of ERK2, Aurora-2, CDK-2, Lck, AKT3, or GSK-3, or the treatment of a disease alleviated thereby, is preferably carried out with a preferred compound of formula I', I", I°, III-a, III-a', or III-a°, as described above. More preferably, each of the aforementioned. methods is carried out with a preferred compound of formula I', I", I°, III-a', or III-a°, and most preferably with a compound of formula I", I°, III-a', or III-a°.

In order that the invention described herein may be more fully understood, the following examples are set forth. It should be understood that these examples are for illustrative purposes only and are not to be construed as limiting this invention in any manner.

SYNTHETIC EXAMPLES

For compounds where the HPLC Method is designated as "A", the following method was utilized: a gradient of water:MeCN, 0.1% TFA (95:5→0:100) was run over 22 minutes at 1 mL/min and 214 nm. For compounds where the HPLC Method is designated as "B", the following method was utilized: a gradient of water:MeCN, 0.1% TFA (90:10→0:100) was run over 8 minutes at 1 mL/min and 214 nm. Each of methods A and B utilize the YMC ODS-AQ 55 120A column with a size of 3.0×150 mm. As used herein, the term "$R_t$" refers to the retention time, in minutes, associated with the compound using the designated HPLC method.

Example 1

1

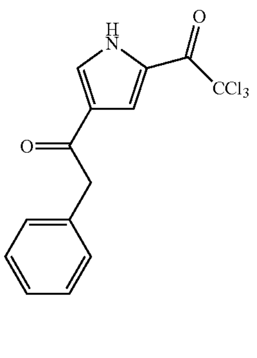

2,2,2-Trichloro-1-(4-phenyl acetyl-1H-pyrrol-2-yl)-ethanone (1): In a dry flask, phenylacetyl chloride (1 equivalent) was combined with 2-trichloroacetyl pyrrole (1 equivalent) in a minimum amount of dichloromethane (DCM) to dissolve the reactants. To the resulting solution, at ambient temperature, was added aluminum trichloride (1 equivalent). After 2 hours, the reaction mixture was applied directly onto a silica gel column. Gradient elution with 10% ethyl acetate to 50% ethyl acetate in hexanes provided compound 1 in 60% yield. $^1H$ NMR ($CDCl_3$) δ 4.0 (s, 2H), 7.1–7.35 (m, 7H), 9.7 (br s, NH). HPLC using method B provided $R_t$ of 4.9 minutes. LC/MS (M+1) 330.2, (M−1) 328.1.

Example 2

2

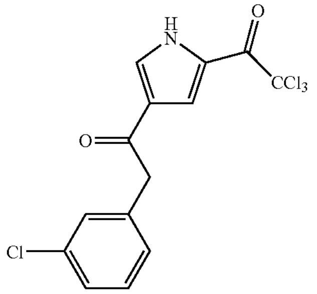

2,2,2-Trichloro-1-(4-(3-Chlorophenyl) acetyl-1H-pyrrol-2-yl)-ethanone (2): In a dry flask, 3-chlorophenylacetyl chloride (1 equivalent) was combined with 2-trichloroacetyl pyrrole (1 equivalent) in a minimum amount of dichloromethane (DCM). To the resulting solution, at ambient temperature, was added aluminum trichloride (1 equivalent). After 2 hours, the reaction mixture was applied directly onto a silica gel column. Gradient elution with 10% ethyl acetate to 50% ethyl acetate in hexanes provided compound 2. HPLC using method A provided $R_t$ of 15 minutes

Example 3

3

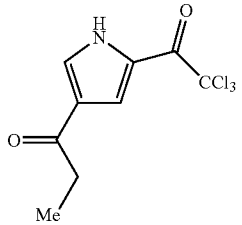

1-[5-(2,2,2-Trichloro-acetyl)-1H-pyrrol-3-yl)-propan-1-one (3): In a dry flask, 3-proprionyl chloride (1 equivalent) was combined with 2-trichloroacetyl pyrrole (1 equivalent) in a minimum amount of dichloromethane (DCM). To the resulting solution, at ambient temperature, was added aluminum trichloride (1 equivalent). After 2 hours, the reaction mixture was applied directly onto a silica gel column. Gradient elution with 10% ethyl acetate to 50% ethyl acetate in hexanes provided compound 3

Example 4

4

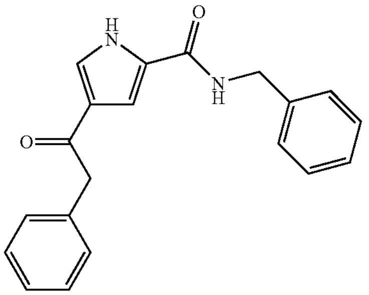

4-Phenylacetyl-1H-pyrrole-2-carboxylic acid benzylamide (4): To a solution of compound 1 (1 equivalent) in DMF, at ambient temperature, was added benzylamine (1.2 equivalents). After 24 hours, the solvent was evaporated and the crude product 4 was used without purification. HPLC using method B provided $R_t$ of 3.8 minutes. FIA/MS (M+1) 319.3, (M−1) 317.2.

Example 5

5

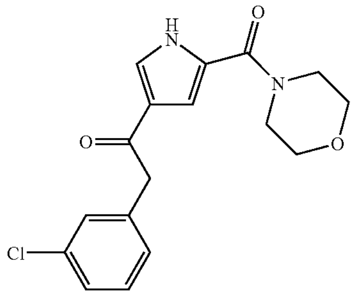

2-(3-Chlorophenyl)1-[5-(morpholine-4-carbonyl)-1H-pyrrol-3-yl]-ethanone (5): To a solution of compound 2 (1 equivalent) in DMF, at ambient temperature, was added morpholine (1.2 equivalents). After 24 hours, the solvent was evaporated and the crude product 5 was used without purification. FIA/MS (M+1) 3.33.3, (M−1) 331.2. $^1$H NMR was consistent with expected structure.

Example 6

6

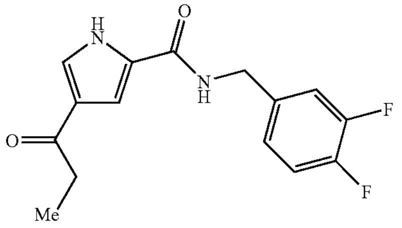

4-Propionyl-1H-pyrrole-2-carboxylic acid 3,4-difluoro-benzylamide (6): To a solution of compound 3 (1 equivalent) in DMF, at ambient temperature, was added 3,4-difluorobenzyl amine (1.2 equivalents). After 24 hours, the solvent was evaporated and the crude product 6 was used without purification.

Example 7

7

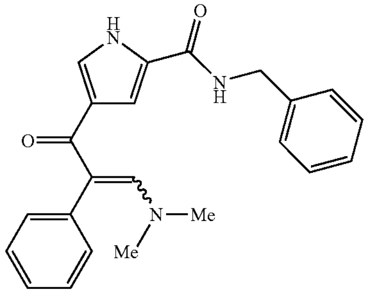

4-(3-Dimethylamino-2-phenyl-acryloyl)-1H-pyrrole-2-carboxylic acid benzylamide (7): To a solution of compound 4 (1 equivalent) in THF, at ambient temperature, was added $(Me_2N)_2CHOt\text{-}Bu$ (3 equivalents). After 24 hours, the solvent was evaporated and the crude product 7 was used without purification. $^1$H NMR ($CDCl_3$) δ 4.4 (s, 2H), 4.8 (s, NH), 6.8–7.4 (m, 13H).

Example 8

8

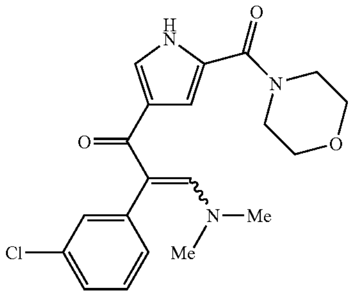

2-(3-Chloro-phenyl)-3-dimethylamino-1-[5-(morpholine-4-carbonyl)-1H-pyrrol-3-yl]-propenone (8): To a solution of compound 5 (1 equivalent) in THF, at ambient temperature, was added $(Me_2N)_2CHOt\text{-}Bu$ (3 equivalents). After 24 hours, the solvent was evaporated and the crude product 8 was used without purification. HPLC using method B provided $R_t$ of 11.2 minutes.

Example 9

III-a-74

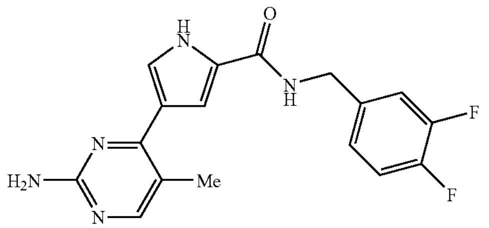

4-(2-Amino-5-methyl-pyrimidin-4-yl)-1H-pyrrole-2-carboxylic acid 3,4-difluoro-benzylamide (III-a-74): Step 1: To a solution of compound 6 (1 equivalent) in THF, at ambient temperature, was added $(Me_2N)_2CHOt\text{-}Bu$ (3 equivalents). After 24 hours, the solvent was evaporated and the crude product was utilized without purification. Step 2: To a solution of the compound formed above at Step 1 (1 equivalent) in ethanol, at ambient temperature, was added guanidine (3 equivalents) and the resulting mixture heated at reflux. After 12 hours, the solvent was evaporated and the crude product purified by preparatory HPLC (reverse phase; 10–90% MeCN in water; 15 minutes) to afford the desired compound III-a-74. HPLC using method B provided $R_t$ of 7.9 minutes. $^1H$ NMR was consistent with expected structure. FIA/MS Obs. M+1/M−1.

Example 10

III-a-72

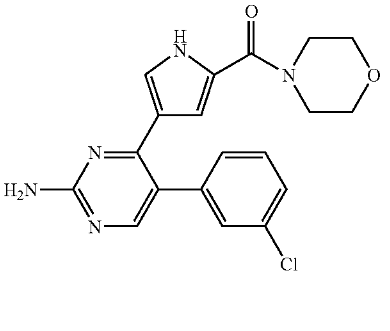

{4-[2-Amino-5-(3-chlorophenyl)-pyrimidine-4-yl]-1H-pyrrol-2-yl}-morpholin-4-yl-methanone (III-a-72): To a solution of compound 8 (1 equivalent) in ethanol, at ambient temperature, was added guanidine (3 equivalents) and the resulting mixture heated at reflux. After 12 hours, the solvent was evaporated and the crude product purified by preparatory HPLC (reverse phase; 10→90% MeCN in water; 15 minutes) to afford the desired compound III-a-72. HPLC using method B, $R_t$=7.9 minutes. $^1H$ NMR was consistent with expected structure. FIA/MS Obs. (M+1) 384.4 amu.

Example 11

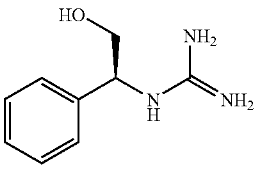

N-(2-Hydroxy-1-(S)-phenyl-ethyl)-guanidine•HCl: (S)-Phenylglycinol (0.38 g, 2.7 mmol) and bis-Boc guanidine-(N)-triflate (0.9 g, 2.3 mmol) were combined in methylene chloride (anhydrous, 5 mL) and stirred at ambient temperature overnight. Completion of the reaction was verified by HPLC. The mixture was diluted with ethyl acetate, washed with 2M sodium bisulfite, brine then dried over $MgSO_4$, filtered and concentrated in vacuo. The bis-Boc guanidine intermediate was treated with 4N HCl/dioxane (5 mL) and stirred at room temperature until deprotection was complete (48 h) to afford the title compound.

Example 12

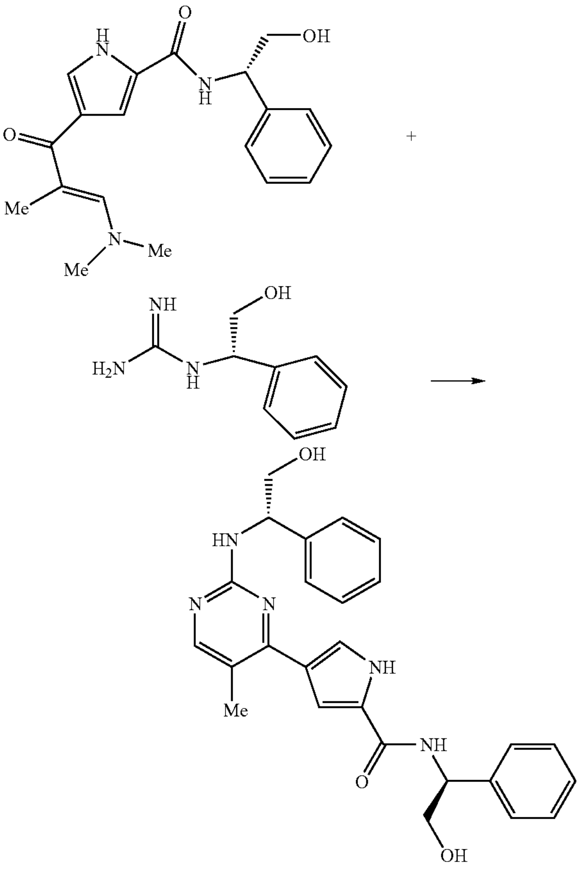

III-a-155

4-[2-(2-Hydroxy-1-(S)-phenyl-ethylamino)-5-methyl-pyrimidin-4-yl]-1H-pyrrole-2-carboxylic acid (2-hydroxy-1-(S)-phenyl-ethyl)-amide (III-a-155): 4-(3-Dimethylamino- 2-methyl-acryloyl)-1H-pyrrole-2-carboxylic acid (2-hydroxy-1-phenyl-ethyl)-amide (100 mg, 0.29 mmol) was combined with N-(S)-phenylglycinol guanidine•HCl (126 mg) and potassium carbonate (121 mg) in N,N-dimethylacetamide (2 mL). The resulting suspension was heated and stirred at 100° C. for 24 hours. The crude material was diluted with ethyl acetate, washed with saturated $NaHCO_3$, brine, dried over MgSO4 and concentrated in vacuo. Purification by prep HPLC (Gilson: Column CombiHT SB-C189 5 μM 21.2 mm×100 mm, eluent=0.1% TFA MeCN/H2O gradient) followed by preparative TLC (silica, 5% MeOH in $CH_2Cl_2$) afforded compound III-a-155 as a pale yellow solid (8.0 mg). HPLC Method B, $R_t$=4.76 minutes; MS (FIA) 458.2 (M+1), 456.1 (M−1); $^1H$ NMR consistent with structure.

Example 13

III-a-162

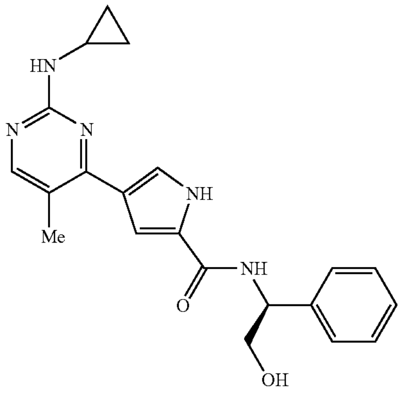

4-(2-Cyclopropylamino-5-methyl-pyrimidin-4-yl)-1H-pyrrole-2-carboxylic acid (2-hydroxy-1-(S)-phenyl-ethyl)-amide (III-a-162): 4-(3-Dimethylamino-2-methyl-acryloyl)-1H-pyrrole-2-carboxylic acid (2-hydroxy-1-phenyl-ethyl)-amide (100 mg, 0.29 mmol) was combined with cyclopropyl guanidine•HCl (80 mg) and potassium carbonate (121 mg) in N,N-dimethylacetamide (2 mL). The resulting suspension was heated and stirred at 100° C. for 24 hours. The crude material was diluted with ethyl acetate, washed with saturated $NaHCO_3$ and brine, dried over MgSO4 then concentrated in vacuo. Purification by preparative TLC (silica, 1:1 EtOAc:Hexanes) afforded III-a-162 as a yellow solid (7.8 mg). HPLC Method B, $R_t$=4.29 minutes; LC/MS(m/z) 378.2 (M+1), 376.2 (M−1); $^1H$ NMR consistent with structure.

Example 14

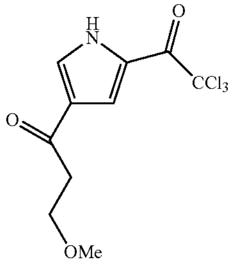

3-Methoxy-1-[5-(2,2,2-trichloro-acetyl)-1H-pyrrol-3-yl]-propan-1-one: To a solution of 2-trichloroacetyl pyrrole (1.0 equivalent, 4.67 g, 22 mmol) in methylene chloride (5 mL) was added 3-methoxypropionyl chloride (1.0 equivalent, 22 mmol) then aluminium trichloride (1.0 equivalent, 2.93 g, 22 mmol) was added in small portions. After 2.5 hours, the crude mixture was chromatographed on silica gel (MeOH 2% in DCM) to afford 3.0 g of the Friedel-Craft product. $^1H$ NMR consistent with structure.

Example 15

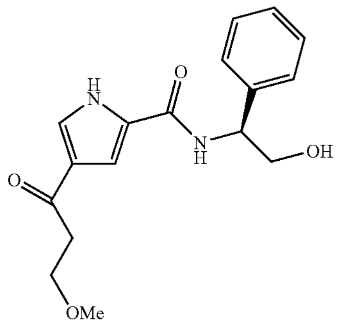

4-(3-Methoxy-propionyl)-1H-pyrrole-2-carboxylic acid (2-hydroxy-1-(S)-phenyl-ethyl)-amide: To a solution of 3-methoxy-1-[5-(2,2,2-trichloro-acetyl)-1H-pyrrol-3-yl]-propan-1-one (3.0 g, 10 mmol) in acetonitrile (50 mL), cooled to 0° C., was added (S)-(+)-phenyl glycinol (1.2 equivalent, 1.65 g, 12 mmol) and the resulting mixture stirred for 3 days at room temperature. The solvent was removed under reduced pressure and the residue purified by chromatography on silica gel (MeOH 5% in DCM) to afford 5.3 g of the title compound as a white solid. HPLC Method B, $R_t$=4.2 minutes; LC/MS(m/z) 317.03 (M+1), 315.00 (M−1); $^1H$ NMR consistent with structure.

Example 16

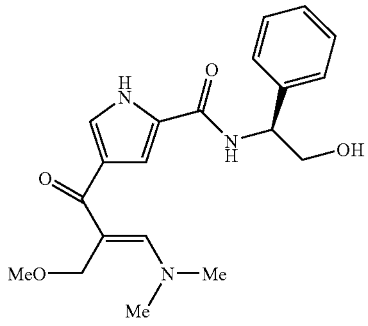

4-(3-Dimethylamino-2-methoxymethyl-acryloyl)-1H-pyrrole-2-carboxylic acid (2-hydroxy-1-(S)-phenyl-ethyl)-amide: 4-(3-Methoxy-propionyl)-1H-pyrrole-2-carboxylic acid (2-hydroxy-1-(S)-phenyl-ethyl)-amide was treated with an excess of Bredereck's reagent in THF at room temperature to 50° C. for 3 days. The solvent was removed under reduced pressure and the concentrate was used directly in the next step. HPLC Method B, $R_t$=5.0 minutes "broad peak".

Example 17

III-a-164

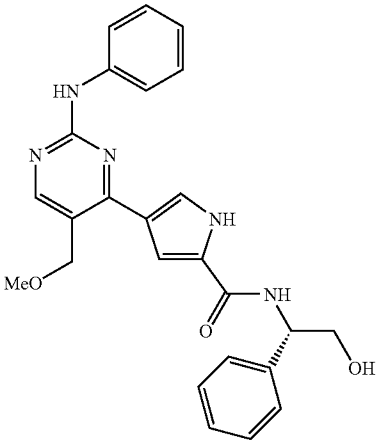

4-(5-Methoxymethyl-2-phenylamino-pyrimidin-4-yl)-1H-pyrrole-2-carboxylic acid (2-hydroxy-1-(S)-phenyl-ethyl)-amide (III-a-164): 4-(3-Dimethylamino-2-methoxymethyl-acryloyl)-1H-pyrrole-2-carboxylic acid (2-hydroxy-1-(S)-phenyl-ethyl)-amide (0.27 mmol) was combined with phenyl guanidine (73 mg) in N,N-dimethylacetamide (2 mL) and the resulting suspension was heated at 90° C. for 35 hours. The reaction mixture was diluted with ethyl acetate, washed with saturated $NaHCO_3$ and brine, dried over $MgSO_4$ and concentrated in vacuo. The crude product was purified by prep HPLC (Gilson: Column=CombiHT SB-C189 5 μM, 21.2 mm×100 mm, eluent=0.1% TFA MeCN/H2O gradient) to afford III-a-164 as a yellow solid (3.2 mg). LC/MS(m/z) 444.16 (M+1), 442.19 (M−1); HPLC Method B, $R_t$=5.16 minutes: $^1$H NMR consistent with structure.

Example 18

III-a-165

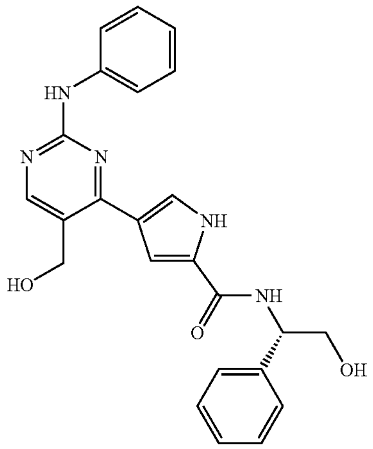

4-(5-Hydroxymethyl-2-phenylamino-pyrimidin-4-yl)-1H-pyrrole-2-carboxylic acid (2-hydroxy-1-(S)-phenyl-ethyl)-amide (III-a-165): To a solution of III-a-164 (15 mg, 0.03 mmol) in dichloromethane (2 mL), cooled to −78° C., was added $BBr_3$ (135 μL, 0.13 mmol). After 15 minutes the reaction was allowed to warm to room temperature. After 45 minutes, the reaction was quenched with a saturated solution of sodium carbonate and the resulting mixture was stirred for an additional 30 minutes before extraction with ethyl acetate. The organic layers were combined and washed with brine then dried over sodium sulfate. The crude mixture was purified by prep TLC (silica, 7% MeOH in $CH_2Cl_2$) to afford III-a-165 as a beige solid (1.6 mg). HPLC Method B, $R_t$=4.54 minutes; LC/MS (m/z) 430.15 (M+1), 428.03 (M−1); $^1$H NMR consistent with structure.

Example 19

III-a-161

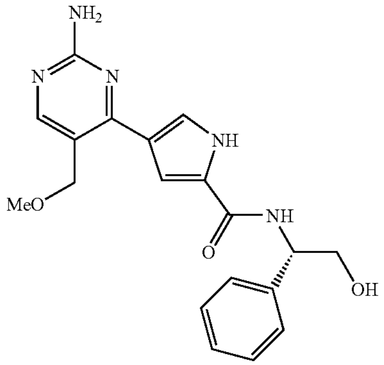

4-(2-Amino-5-methoxymethyl-pyrimidin-4-yl)-1H-pyrrole-2-carboxylic acid (2-hydroxy-1-phenyl-ethyl)-amide (III-a-161): The enamine formed above at Example 16 (0.27 mmol) was combined with guanidine•HCl (51 mg), and $K_2CO_3$ (100 mg) in N,N-dimethylacetamide (4 mL). The heterogenous mixture was heated and stirred at 90° C. for 35 h. The crude material was diluted with ethyl acetate, washed with saturated $NaHCO_3$ and brine, dried ($MgSO_4$) and concentrated in vacuo. Purification by prep HPLC (Gilson: Column=CombiHT SB-C189 5 μM, 21:2 mm×100 mm, eluent=0.1% TFA MeCN/$H_2O$ gradient) afforded III-a-161 as a yellow solid (2.0 mg). LC/MS(m/z) 368.12 (M+1), 366.15 (M−1), $R_t$ (HPLC)=3.77 min, $^1$H NMR consistent with structure.

Example 20

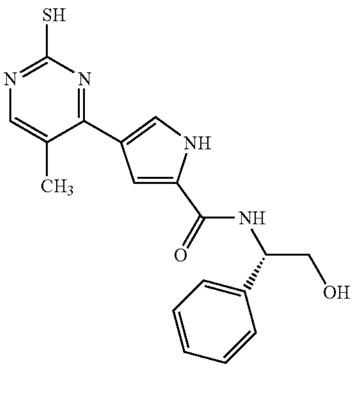

4-(2-Mercapto-5-methyl-pyrimidin-4-yl)-1H-pyrrole-2-carboxylic acid (2-hydroxy-1-(S)-phenyl-ethyl)-amide: 4-(3-Dimethylamino-2-methoxymethyl-acryloyl)-1H-pyrrole-2-carboxylic acid (2-hydroxy-1-(S)-phenyl-ethyl)-amide (17.6 mmol, 6.0 g) was combined with thiourea (39 mmol, 3.0 g) and potassium carbonate (53 mmol, 7.3 g) in ethanol (50 mL) and the resulting suspension was heated at 90° C. for 24 hrs. The solvent was removed in vacuo and the resulting black solid was diluted with water and the solid was removed by filtration. The solid was washed with ethyl acetate twice and the aqueous solution was acidified to pH 5–6 with HCl (2N). The solid formed was removed by filtration and the aqueous solution was then extracted twice with ethyl acetate. The combined organic phases were dried over sodium sulfate. The solvent was removed under vacuum to afford the title compound as a brown solid (3.0 g, 48% yield). HPLC Method B, $R_t$=3.7 minutes, $^1$H NMR consistent with structure.

Example 21

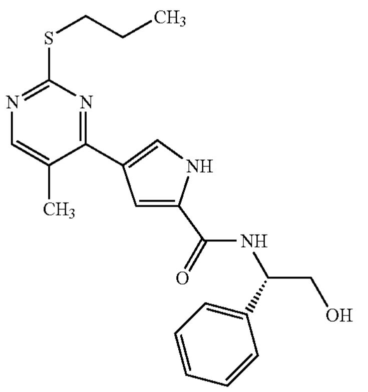

4-(5-Methyl-2-propylsulfanyl-pyrimidin-4-yl)-4H-pyrrole-2-carboxylic acid (2-hydroxy-1-(S)-phenyl-ethyl)-amide: To a solution of 4-(2-mercapto-5-methyl-pyrimidin-4-yl)-1H-pyrrole-2-carboxylic acid (2-hydroxy-1-(S)-phenyl-ethyl)-amide (7.7 mmol, 2.74 mmol) in aqueous ammonia (15%) was added at room temperature n-propyliodide (11.6 mmol, 1.1 mL). The solution was stirred overnight at room temperature. The resulting solid was collected by filtration and used directly for the next step. $^1$H NMR consistent with the structure.

Example 22

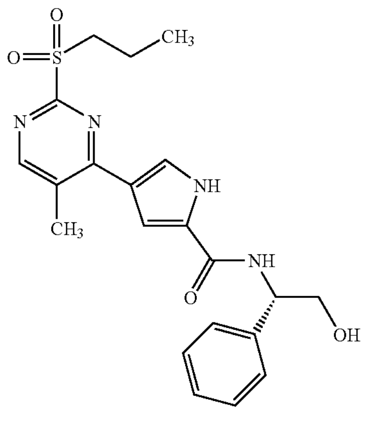

4-[5-Methyl-2-(propane-1-sulfonyl)-pyrimidin-4-yl]-1H-pyrrole-2-carboxylic acid (2-hydroxy-1-(S)-phenyl-ethyl)-amide: The thiopropyl compound (7.7 mmol, 3.05 g) prepared at Example 21 above was dissolved in 120 mL of ethanol. To this solution, maintained at room temperature, was added m-CPBA (70% w/w %, 23.1 mmol, 4.0 g). The solution was stirred for an additional. 4 hours at room temperature. The solvent was removed in vacuo and the residue dissolved in ethyl acetate, then washed 4 times with a solution of sodium hydroxide (1N). The organic phase was dried over sodium sulfate and concentrated in vacuo to afford the title compound as a white solid (1.7 g, 51% yield for 2 steps) HPLC Method B, $R_t$=5.4 minutes. $^1$H NMR consistent with the structure.

Example 23

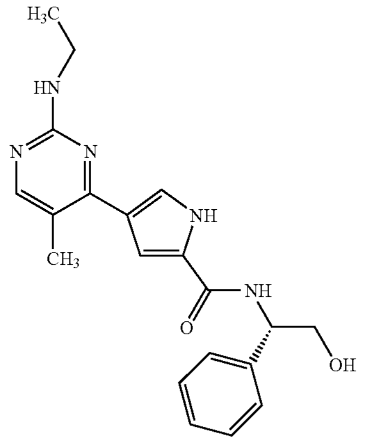

4-(2-Ethylamino-5-methyl-pyrimidin-4-yl)-1H-pyrrole-2-carboylic acid (2-hydroxy-1-(S)-phenyl-ethyl)-amide: To a solution of 4-[5-methyl-2-(propane-1-sulfonyl)-pyrimidin-4-yl]-1H-pyrrole-2-carboxylic acid (2-hydroxy-1-(S)-phenyl-ethyl)-amide (47 μmol, 20 mg) in DMSO (1 mL) was added ethylamine (0.5 mmol, 150 μL). The mixture was heated at 130° C. for 24 hours to afford the title compound. LC/MS(m/z) 366.2 (M+1); HPLC Method B, $R_t$=4.2 minutes; $^1$H NMR consistent with the structure.

Example 24

III-a-226

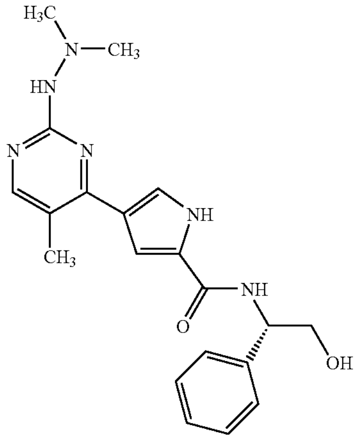

4-[2-(N',N'-Dimethyl-hydrazino)-5-methyl-pyrimidin-4-yl]-1H-pyrrole-2-carboxylic acid (2-hydroxy-1-(S)-phenyl-ethyl)-amide (III-a-226): To a solution of 4-(3-dimethylamino-2-methoxymethyl-acryloyl)-1H-pyrrole-2-carboxylic acid (2-hydroxy-1-(S)-phenyl-ethyl)-amide (0.15 mmol, 50 mg) in DMA (2 mL) was added dimethyl-N,N-aminoguanidine•2HCl (0.17 mmol, 30 mg) and potassium carbonate (0.36 mmol, 50 mg). The reaction Mixture was stirred for 48 hrs at 100° C. The solvent was removed by hi-vacuum "GeneVac" and the residue purified by preparative HPLC (Gilson: Column=CombiHT SB-C189 5 μM 21.2 mm×100 mm, eluent=0.1% TFA MeCN/H2O gradient) followed by preparative TLC (silica, 5% MeOH in $CH_2Cl_2$) "double elutions" afforded compound III-a-226 as a pale yellow solid (1.3 mg). HPLC Method B, $R_t$=4.03 min.; LC/MS (m/z) 381.1 (M+1), 379.1 (M−1); $^1$H NMR consistent with structure.

Example 25

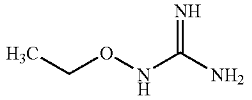

Ethanolguanidine: Ethanolamine hydrochloride (200 mg, 2 mmol) was added to a mixture of N, N'-di-boc -N"-triflylguanidine (800 mg, 2 mmol) and TEA (0.28 mL, 2 mmol) in dichloromethane (10 mL). The mixture was stirred overnight then diluted with EtOAc, washed with sodium bisulfate (2M), saturated sodium bicarbonate, dried over $NaSO_4$ and concentrated in vacuo. The crude residue was purified by flash column chromatography eluting with 20% $CH_2Cl_2$/hexane to afford a white solid (0.56 g, 92%).). $^1$H NMR ($CDCl_3$): δ 4.18 (q, 2H), 1.60 (d, 18H), 1.37 (t, 3H). To this bis-Boc guanidine was added 4M HCl/dioxane (5 mL). The mixture was stirred for 24 h and then concentrated to afford the title compound (0.26 g). $^1$H NMR (MeOD): δ 3.92 (q, 2H), 1.27 (t, 3H). MS (M+1) 104.

Example 26

III-a-195

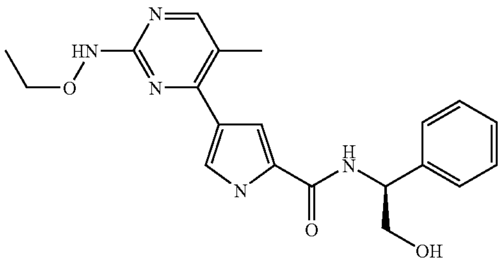

4-(2-Ethanolamino-5-methyl-pyrimidin-4-yl)-1H-pyrrole-2-carboxylic acid (2-hydroxy-1-(s)-phenyl-ethyl)-amide (III-a-195): To a mixture of 4-(3-dimethylamino-2-methyl-acryloyl)-1H-pyrrole-2-carboxylic acid (2-hydroxymethyl-1-(S)-phenyl-ethyl) amide (0.1 mmol) and $K_2CO_3$ (55 mg, 0.4 mmol) in DMF (1 mL) was added ethanolguanidine hydrogen chloride (0.2 mmol). The resulting suspension was stirred for 6 hours at 90° C. The reaction mixture was filtered and the filtrate concentrated in vacuo. The crude residue was purified by preparative HPLC (Gilson: Column=CombiHT SB-C189 5 μM 21.2 mm×100 mm, eluent=0.1% TFA MeCN/H2O gradient) to afford compound III-a-195 as yellow oil (21 mg). HPLC (method B) $R_t$=4.08 min; MS (M+1) 382.1.

Example 27

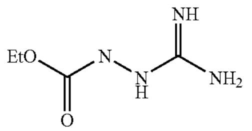

Ethyl carbamate guanidine: Ethylcarbazate (208 mg, 2 mmol) was added to a solution of N'N'-di-boc N"-triflylguanidine (800 mg, 2 mmol) in dichloromethane (10 mL). The mixture was stirred for overnight then diluted with EtOAc, washed with sodium bisulfat (2M), saturated sodium bicarbonate, dried over anhydrous $NaSO_4$ and concentrated in vacuo. The crude residue was purified by flash column chromatography eluting with 30% EtOAc/hexane to afford a white solid (0.55 g). To this bis-boc guanidine was added 4M HCl/Dioxane (5 mL). The mixture was stirred for 24 hours and then concentrated to afford the title compound. $^1$H NMR (MeOD): δ 3.4.18 (d, 2H), 3.26 (s, 1H), 1.28 (t, 3H). MS (M+1) 134.

Example 28

III-a-218

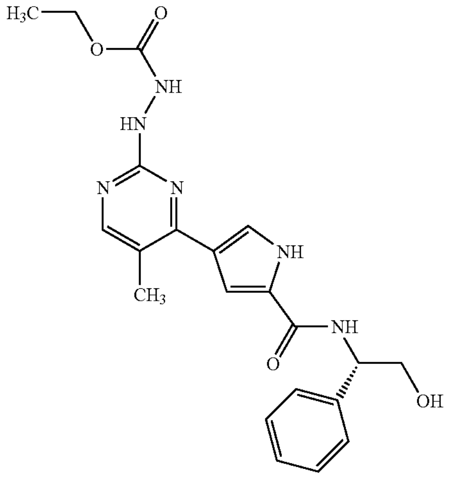

4-(2-Ethyl carbamate-5-methyl-pyrimidin-4-yl)-1H-pyrrole-2-carboxylic acid (2-hydroxy-1-(s)-phenyl-ethyl)-amide (III-a-218): To a mixture of 4-(3-dimethylamino-2-methyl-acryloyl)-1H-pyrrole-2-carboxylic acid (2-hydroxymethyl-1-(S)-phenyl-ethyl) amide (0.1 mmol) and $K_2CO_3$ (55 mg, 0.4 mmol) in DMF (1 mL) was added ethyl carbamate guanidine hydrogen chloride (0.2 mmol). The resulting suspension was stirred for 6 hours at 90° C. The reaction mixture was filtered and the filtrate was concentrated in vacuo. The crude residue was purified by preparative HPLC (Gilson: Column=CombiHT SB-C189 5 μM 21.2 mm×100 mm, eluent=0.1% TFA MeCN/H2O gradient) to afford compound III-a-218 as a yellow oil (10 mg). HPLC (method B) $R_t$=4.03; MS (M+1) 425.1. $^1$H NMR (MeOD) 8.08 (s, 1H); 7.87 (s, 1H); 7.7 (s, 1H), 7.24–7.5 (m, 5H); 5.15 (t, 1H), 4.2 (m, 2H), 3.85 (m, 2H); 2.5 (s, 3H).

Example 29

We have prepared other compounds of formula III-a by methods substantially similar to those described in the above Examples 1–28 and those illustrated in Schemes I–XII. The characterization data for these compounds is summarized in Table 3 below and includes LC/MS, HPLC, and $^1$H NMR data.

Where applicable, $^1$H NMR data is summarized in Table 3 below wherein "Y" designates $^1$H NMR data is available and was found to be consistant with structure. Compound numbers correspond to the compound numbers listed in Table 1.

TABLE 3

Characterization Data for Selected Compounds

| Compound No III-a- | M + 1 | M − 1 | HPLC Method | $R_t$ (min) | $^1$H NMR |
|---|---|---|---|---|---|
| 122 | 352.17 | — | — | — | — |
| 136 | 432.2 | 429.8 | B | 5.53 | — |
| 137 | 444.3 | 442.3 | B | 5.00 | — |
| 138 | 430.2 | 428.3 | B | 4.47 | Y |
| 139 | 458.3 | 456.3 | B | 4.72 | — |
| 140 | 493.3 | 491.3 | B | 4.45 | — |
| 141 | 520.2 | 518.2 | B | 5.98 | — |
| 142 | 436.2 | — | B | 4.0 | — |
| 144 | 440.17 | — | A | 10.1 | Y |
| 145 | 446.2 | 444.1 | B | 5.45 | — |
| 146 | 482.2 | — | B | 5.69 | — |
| 147 | 464.2 | — | B | 5.87 | — |
| 148 | 500.1 | — | B | 6.12 | — |
| 149 | 482.2 | 480.4 | B | 6.11 | — |
| 150 | 428.2 | 426.2 | B | 5.13 | — |
| 153 | 380.2 | 378.2 | B | 4.63 | Y |
| 154 | 420.1 | 418.1 | B | 4.74 | Y |
| 155 | 458.2 | 456.1 | B | 4.76 | Y |
| 156 | 441.13 | — | B | 5.14 | — |
| 157 | 498.2 | — | B | 6.00 | — |
| 159 | 392.2 | 390.1 | B | 4.75 | Y |
| 162 | 378.2 | 376.2 | B | 4.29 | Y |
| 163 | 380.2 | 378.0 | B | 4.65 | Y |
| 180 | 338.15 | — | B | 3.8 | — |
| 181 | 396.22 | — | B | 3.9 | — |
| 182 | 382.18 | — | B | 4.1 | — |
| 183 | 352.17 | — | — | — | — |
| 188 | 367.2 | — | B | 2.86 | Y |
| 190 | 453.1 | — | B | 5.86 | Y |
| 191 | 384.1 | — | B | 4.46 | Y |
| 192 | 384.1 | — | B | 4.41 | Y |
| 214 | 428.1 | — | B | 4.9 | — |
| 215 | 415.1 | — | B | 4.3 | Y |
| 216 | 422.1 | — | B | 4.43 | Y |
| 217 | 422.1 | — | B | 4.44 | — |
| 219 | 429.3 | — | B | 3.64 | Y |
| 221 | 405.19 | — | B | 4.5 | — |
| 227 | 482.4 | — | B | 5.5 | — |
| 229 | 419.03 | — | B | 4.29 | Y |
| 230 | 510.4 | — | B | 5.19 | — |
| 231 | 432.3 | — | B | 5.23 | Y |

Biological Testing

The activity of the present compounds as protein kinase inhibitors may be assayed in vitro, in vivo or in a cell line. In vitro assays include assays that determine inhibition of either the phosphorylation activity or ATPase activity of the activated protein kinase. Alternate in vitro assays quantitate the ability of the inhibitor to bind to the protein kinase. Inhibitor binding may be measured by radiolabelling the inhibitor prior to binding, isolating the inhibitor protein kinase complex and determining the amount of radiolabel bound. Alternatively, inhibitor binding may be determined by running a competition experiment where new inhibitors are incubated with the protein kinase bound to known radioligands. The details of the conditions used for performing these assays are set forth in Examples 30 through 37.

Example 30

ERK Inhibition Assay

Compounds were assayed for the inhibition of ERK2 by a spectrophotometric coupled-enzyme assay (Fox et al (1998) *Protein Sci* 7, 2249). In this assay, a fixed concentration of activated ERK2 (10 nM) was incubated with various concentrations of the compound in DMSO (2.5%) for 10 min. at 30° C. in 0.1 M HEPES buffer, pH 7.5, containing 10 mM $MgCl_2$, 2.5 mM phosphoenolpyruvate, 200 μM NADH, 150 μg/mL pyruvate kinase, 50 μg/mL lactate dehydrogenase, and 200 μM erktide peptide. The reaction was initiated by the addition of 65 μM ATP. The rate of decrease of absorbance at 340 nM was monitored. The $IC_{50}$ was evaluated from the rate data as a function of inhibitor concentration.

Table 4 shows the results of the activity of selected compounds of this invention in the ERK2 inhibition assay. The compound numbers correspond to the compound numbers in Table 1. Compounds having an activity designated as "A" provided a percent inhibition less than or equal to 33%; compounds having an activity designated as "B" provided a percent inhibition of between 24% and 66%; and compounds having an activity designated as "C" provided a provided a percent inhibition of between 67% and 100%. Compounds having an activity designated as "ID" provided a $K_i$ of less than 0.1 micromolar; compounds having an activity designated as "E" provided a $K_i$ of between 0.1 and 1.0 micromolar; and compounds having an activity designated as "F" provided a $K_i$ of greater than 1.0 micromolar.

TABLE 4

ERK2 Inhibitory Activity of Selected Compounds

| No. III-a- | Activity | No. III-a- | Activity | No. III-a- | Activity |
|---|---|---|---|---|---|
| 2 | B | 3 | A | 4 | A |
| 5 | A | 6 | A | 7 | A |
| 8 | A | 9 | A | 10 | A |
| 11 | A | 12 | B | 13 | A |
| 14 | B | 15 | A | 16 | A |
| 17 | A | 18 | A | 19 | A |
| 20 | A | 21 | B | 22 | A |
| 23 | C | 24 | A | 25 | A |
| 26 | A | 27 | A | 28 | A |
| 29 | C | 30 | A | 31 | A |
| 32 | A | 33 | A | 34 | B |
| 35 | B | 36 | B | 37 | C |
| 39 | C | 40 | C | 41 | A |
| 42 | C | 43 | A | 44 | C |
| 45 | B | 46 | A | 47 | C |
| 48 | B | 49 | A | 50 | A |
| 51 | A | 52 | A | 53 | A |
| 54 | A | 55 | A | 56 | A |
| 57 | A | 58 | A | 59 | A |
| 60 | A | 61 | A | 62 | C |

TABLE 4-continued

ERK2 Inhibitory Activity of Selected Compounds

| No. III-a- | Activity | No. III-a- | Activity | No. III-a- | Activity |
|---|---|---|---|---|---|
| 63 | A | 64 | A | 65 | A |
| 66 | A | 67 | A | 68 | A |
| 69 | A | 70 | A | 71 | A |
| 72 | B | 100 | A | 101 | A |
| 102 | A | 103 | F | 104 | A |
| 105 | E | 107 | F | 111 | D |
| 112 | D | 114 | F | 117 | D |
| 120 | E | 121 | A | 122 | C |
| 123 | A | 124 | C | 125 | A |
| 131 | A | 132 | F | 133 | F |
| 134 | D | 135 | C | 139 | D |
| 140 | D | 141 | D | 142 | D |
| 144 | E | 145 | D | 147 | D |
| 148 | D | 149 | D | 150 | D |
| 151 | D | 152 | D | 153 | D |
| 154 | D | 155 | D | 157 | D |
| 158 | D | 159 | D | 160 | E |
| 161 | E | 162 | D | 163 | D |
| 166 | E | 168 | F | 169 | E |
| 170 | F | 171 | F | 172 | F |
| 173 | E | 174 | D | 175 | D |
| 176 | D | 177 | D | 178 | D |
| 179 | D | 180 | F | 184 | E |
| 188 | E | 189 | D | 190 | E |
| 191 | D | 192 | E | 193 | D |
| 194 | D | 195 | D | 196 | D |
| 197 | F | 198 | D | 199 | D |
| 200 | D | 201 | D | 202 | D |
| 203 | D | 204 | D | 205 | D |
| 206 | D | 207 | D | 208 | D |
| 209 | D | 210 | D | 211 | D |
| 212 | D | 213 | D | 214 | D |
| 215 | D | 216 | D | 217 | D |
| 218 | E | 219 | D | 220 | D |
| 221 | D | 222 | D | 223 | D |
| 224 | D | 225 | D | 226 | D |
| 227 | D | 229 | E | 230 | D |
| 231 | D | 232 | D | 233 | D |
| 234 | D | 235 | D | 236 | D |
| 237 | D | 238 | D | — | — |

Example 31

ERK2 Inhibition: Cell Proliferation Assay

Compounds may be assayed for the inhibition of ERK2 by a cell proliferation assay. In this assay, a complete media is prepared by adding 10% fetal bovine serum and penicillin/streptomycin solution to RPMI 1640 medium (JRH Biosciences). Colon cancer cells (HT-29 cell line) are added to each of 84-wells of a 96 well plate at a seeding density of 10,000 cells/well/150 μL. The cells are allowed to attach to the plate by incubating at 37° C. for 2 hours. A solution of test compound is prepared in complete media by serial dilution to obtain the following concentrations: 20 μM, 6.7 μM, 2.2 μM, 0.74 μM, 0.25 μM, and 0.08 μM. The test compound solution (50 μL) is added to each of 72 cell-containing wells. To the 12 remaining cell-containing wells, only complete media (200 μL) is added to form a control group in order to measure maximal proliferation. To the remaining 12 empty wells, complete media is added to form a vehicle control group in order to measure background. The plates are incubated at 37° C. for 3 days. A stock solution of $^3$H-thymidine (1 mCi/mL, New England Nuclear, Boston, Mass.) is diluted to 20 μCi/mL in RPMI medium then 20 μL of this solution is added to each well. The plates are further incubated at 37° C. for 8 hours then harvested and analyzed for $^3$H-thymidine uptake using a liquid scintillation counter.

Compounds III-a-116, III-a-139, and III-a-136 were each shown to have an $IC_{50}$ of less than 0.1 μM.

Example 32

ERK1 Inhibition Assay

Compounds were assayed for the inhibition of ERK1 by a spectrophotometric coupled-enzyme assay (Fox et al (1998) *Protein Sci* 7, 2249). In this assay, a fixed concentration of activated ERK1 (20 nM) was incubated with various concentrations of the compound in DMSO (2.0%) for 10 min. at 30° C. in 0.1 M HEPES buffer, pH 7.6, containing 10 mM $MgCl_2$, 2.5 mM-phosphoenolpyruvate, 200 μM NADH, 30 μg/mL pyruvate kinase, 10 μg/mL lactate dehydrogenase, and 150 μM erktide peptide. The reaction was initiated by the addition of 140 μM ATP (20 μL). The rate of decrease of absorbance at 340 nM was monitored. The $K_i$ was evaluated from the rate data as a function of inhibitor concentration.

Examples of compounds that were found to inhibit ERK1 with an activity of less than 0.1 μM include III-a-202, III-a-204, and III-a-205.

Example 33

GSK-3 Inhibition Assay

Compounds were screened for their ability to inhibit GSK-3β (AA 1–420) activity using a standard coupled enzyme system (Fox et al. (1998) *Protein Sci.* 7, 2249). Reactions were carried out in a solution containing 100 mM HEPES (pH 7.5), 10 mM $MgCl_2$, 25 mM NaCl, 300 μM NADH, 1 mM DTT and 1.5% DMSO. Final substrate concentrations in the assay were 20 μM ATP (Sigma Chemicals, St Louis, Mo.) and 300 μM peptide (HSSPHQS($PO_3H_2$)EDEEE, American Peptide, Sunnyvale, Calif.). Reactions were carried out at 30° C. and 20 nM GSK-3β. Final concentrations of the components of the coupled enzyme system were 2.5 mM phosphoenolpyruvate, 300 μM NADH, 30 μg/ml pyruvate kinase and 10 μg/ml lactate dehydrogenase.

An assay stock buffer solution was prepared containing all of the reagents listed above with the exception of ATP and the test compound of interest. The assay stock buffer'solution (175 μl) was incubated in a 96 well plate with 5 μl of the test compound of interest at final concentrations spanning 0.002 μM to 30 μM at 30° C. for 10 min. Typically, a 12 point titration was conducted by preparing serial dilutions (from 10 mM compound stocks) with DMSO of the test compounds in daughter plates. The reaction was initiated by the addition of 20 μl of ATP (final concentration 20 μM). Rates of reaction were obtained using a Molecular Devices Spectramax plate reader (Sunnyvale, Calif.) over 10 min at 30° C. The $K_i$ values were determined from the rate data as a function of inhibitor concentration.

Table 5 shows the results of the activity of selected compounds of this invention in the GSK3 inhibition assay. The compound numbers correspond to the compound numbers in Table 1. Compounds having an activity designated as "A" provided a $K_i$ of less than 0.1 micromolar; compounds having an activity designated as "B" provided a $K_i$ of between 0.1 and 1.0 micromolar; and compounds having an activity designated as "C" provided a $K_i$ of greater than 1.0 micromolar.

TABLE 5

GSK3 Inhibitory Activity of Selected Compounds

| No. IIIa- | Activity | No. IIIa- | Activity | No. IIIa- | Activity |
|---|---|---|---|---|---|
| 116 | A | 117 | A | 134 | C |
| 136 | A | 137 | A | 138 | A |
| 139 | A | 140 | A | 141 | A |
| 142 | A | 144 | C | 145 | A |
| 146 | B | 147 | A | 148 | A |
| 149 | A | 150 | B | 151 | A |
| 152 | A | 153 | A | 154 | A |
| 155 | B | 156 | B | 157 | A |
| 158 | A | 159 | A | 162 | A |
| 166 | C | 172 | C | 173 | C |
| 174 | A | 175 | B | 176 | A |
| 177 | B | 178 | B | 179 | A |
| 181 | C | 184 | C | 187 | C |
| 188 | C | 189 | C | 190 | B |
| 191 | B | 193 | B | 194 | A |
| 196 | C | 198 | C | 199 | A |
| 200 | C | 201 | B | 202 | C |
| 203 | B | 205 | B | 206 | A |
| 207 | B | 208 | A | 209 | A |
| 210 | C | 211 | B | 212 | A |
| 213 | B | 214 | B | 215 | A |
| 216 | A | 217 | A | 222 | B |
| 223 | A | 224 | A | 225 | A |
| 227 | C | 228 | A | 230 | B |
| 231 | A | 232 | B | 233 | C |

Example 34

Aurora-2 Inhibition Assay

Compounds were screened in the following manner for their ability to inhibit Aurora-2 using a standard coupled enzyme assay (Fox et al (1998) *Protein Sci* 7, 2249).

To an assay stock buffer solution containing 0.1M HEPES 7.5, 10 mM $MgCl_2$, 1 mM DTT, 25 mM NaCl, 2.5 mM phosphoenolpyruvate, 300 mM NADH, 30 mg/ml pyruvate kinase, 10 mg/ml lactate dehydrogenase, 40 mM ATP, and 800 μM peptide (LRRASLG, American Peptide, Sunnyvale, Calif.) was added a DMSO solution of a compound of the present invention to a final concentration of 30 μM. The resulting mixture was incubated at 30° C. for 10 min. The reaction was initiated by the addition of 10 μL of Aurora-2 stock solution to give a final concentration of 70 nM in the assay. The rates of reaction were obtained by monitoring absorbance at 340 nm over a 5 minute read time at 30° C. using a BioRad Ultramark plate reader (Hercules, Calif.). The $K_i$ values were determined from the rate data as a function of inhibitor concentration. Examples of compounds that were found to inhibit Aurora-2 include III-a-116, III-a-117, III-a-136, III-a-138, III-a-139, III-a-140, and III-a-141.

Example 35

CDK-2 Inhibition Assay

Compounds were screened in the following manner for their ability to inhibit CDK-2 using a standard coupled enzyme assay (Fox et al (1998) *Protein Sci* 7, 2249).

To an assay stock buffer solution containing 0.1M HEPES 7.5, 10 mM $MgCl_2$, 1 mM DTT, 25 mM NaCl, 2.5 mM phosphoenolpyruvate, 300 mM NADH, 30 mg/ml pyruvate kinase, 10 mg/ml lactate dehydrogenase, 100 mM ATP, and 100 μM peptide (MAHHHRSPRKRAKKK, American Peptide, Sunnyvale, Calif.) was added a DMSO solution of a compound of the present invention to a final concentration of 30 μM. The resulting mixture was incubated at 3020 C. for 10 min.

The reaction was initiated by the addition of 10 μL of CDK-2/Cyclin A stock solution to give a final concentration of 25 nM in the assay. The rates of reaction were obtained by monitoring absorbance at 340 nm over a 5-minute read time at 3020 C. using a BioRad Ultramark plate reader (Hercules, Calif.). The $K_i$ values were determined from the rate data as a function of inhibitor concentration.

The following compounds were shown to have $K_i$ values than 0.1 μM for CDK-2: III-a-116, III-a-142, III-a-149, and III-a-152.

The following compounds were shown to have $K_i$ values between 0.1 μM and 1 M for CDK-2: III-a-146, III-a-148, III-a-150, III-a-155, III-a-162, and III-a-174.

The following compounds were shown to have $K_i$ values between 1.0 and 20.0 μM for CDK-2: III-a-117, III-a-156, and III-a-159.

Example 36

LCK Inhibition Assay

The compounds were evaluated as inhibitors of human Lck kinase using either a radioactivity-based assay or spectrophotometric assay.

Lck Inhibition Assay A: Radioactivity-based Assay

The compounds were assayed as inhibitors of full length bovine thymus Lck kinase (from Upstate Biotechnology, cat. no. 14-106) expressed and purified from baculo viral cells. Lck kinase activity was monitored by following the incorporation of $^{33}P$ from ATP into the tyrosine of a random poly Glu-Tyr polymer substrate of composition, Glu:Tyr=4:1 (Sigma, cat. no. P-0275). The following were the final concentrations of the assay components: 0.025 M HEPES, pH 7.6, 10 mM $MgCl_2$, 2 mM DTT, 0.25 mg/ml BSA, 10 μM ATP (1–2 μCi $^{33}P$-ATP per reaction), 5 mg/ml poly Glu-Tyr, and 1–2 units of recombinant human Src kinase. In a typical assay, all the reaction components with the exception of ATP were pre-mixed and aliquoted into assay plate wells. Inhibitors dissolved in DMSO were added to the wells to give a final DMSO concentration of 2.5%. The assay plate was incubated at 30° C. for 10 min before initiating the reaction with $^{33}P$-ATP. After 20 min of reaction, the reactions were quenched with 150 μl of 10% trichloroacetic acid (TCA) containing 20 mM $Na_3PO_4$. The quenched samples were then transferred to a 96-well filter plate (Whatman, UNI-Filter GF/F Glass Fiber Filter, cat no. 7700-3310) installed on a filter plate vacuum manifold. Filter plates were washed four times with 10% TCA containing 20 mM $Na_3PO_4$ and then 4 times with methanol. 200 μl of scintillation fluid was then added to each well. The plates were sealed and the amount of radioactivity associated with the filters was quantified on a TopCount scintillation counter. The radioactivity incorporated was plotted as a function of the inhibitor concentration. The data was fitted to a competitive inhibition kinetics model to get the $K_i$ for the compound.

Lck Inhibition Assay B: Spectrophotometric Assay

The ADP produced from ATP by the human recombinant Lck kinase-catalyzed phosphorylation of poly Glu-Tyr substrate was quanitified using a coupled enzyme assay (Fox et al (1998) *Protein Sci* 7, 2249). In this assay one molecule of NADH is oxidised to NAD for every molecule of ADP produced in the kinase reaction. The disappearance of NADH can be conveniently followed at 340 nm.

The following were the final concentrations of the assay components: 0.025 M HEPES, pH 7.6, 10 mM $MgCl_2$, 2 mM DTT, 5 mg/ml poly Glu-Tyr, and 50 nM of recombinant human Lck kinase. Final concentrations of the components of the coupled enzyme system were 2.5 mM phosphoenolpyruvate, 200 μM NADH, 30 μg/ml pyruvate kinase and 10 μg/ml lactate dehydrogenase.

In a typical assay, all the reaction components with the exception of ATP were pre-mixed and aliquoted into assay plate wells. Inhibitors dissolved in DMSO were added to the wells to give a final DMSO. concentration of 2.5%. The assay plate was incubated at 30° C. for 10 min before initiating the reaction with 150 μM ATP. The absorbance change at 340 nm with time, the rate of the reaction, was monitored on a molecular devices plate reader. The data of rate as a function of the inhibitor concentration was fitted to competitive inhibition kinetics model to get the $K_i$ for the compound.

The following compounds were shown to have $K_i$ values than 1 μM for Lck: III-a-170, III-a-171, III-a-172, III-a-173, III-a-181, and III-a-203.

The following compounds were shown to have $K_i$ values between 1.0 and 20.0 μM for Lck: III-a-204, III-a-205, III-a-206, and III-a-207.

Example 37

AKT3 Inhibition Assay

Compounds were screened for their ability to inhibit AKT3 using a standard coupled enzyme assay (Fox et al., Protein Sci., (1998) 7, 2249). Assays were carried out in a mixture of 100 mM HEPES 7.5, 10 mM $MgCl_2$, 25 mM NaCl , 1 mM DTT and 1.5% DMSO. Final substrate concentrations in the assay were 170 μM ATP (Sigma Chemicals) and 200 μM peptide (RPRAATF, American Peptide, Sunnyvale, Calif.). Assays were carried out at 30° C. and 45 nM AKT3. Final concentrations of the components of the coupled enzyme system were 2.5 mM phosphoenolpyruvate, 300 μM NADH, 30 μg/ML pyruvate kinase and 10 μg/ml lactate dehydrogenase.

An assay stock buffer solution was prepared containing all of the reagents listed above, with the exception of AKT3, DTT, and the test compound of interest. 56 μl of the stock solution was placed in a 384 well plate followed by addition of 1 μl of 2 mM DMSO stock containing the test compound (final compound concentration 30 μM). The plate was preincubated for about 10 minutes at 30° C. and the reaction initiated by addition of 10 μl of enzyme (final concentration 45 nM) and 1 mM DTT. Rates of reaction were obtained using a BioRad Ultramark plate reader (Hercules, Calif.) over a 5 minute read time at 30° C. Compounds showing greater than 50% inhibition versus standard wells containing the assay mixture and DMSO without test compound were titrated to determine $IC_{50}$ values.

Selected compounds of this invention that inhibit AKT3 include: III-a-238.

While we have presented a number of embodiments of this invention, it is apparent that our basic construction can be altered to provide other embodiments which utilize the compounds and methods of this invention. Therefore, it will be appreciated that the scope of this invention is to be defined by the appended claims rather than by the specific embodiments which have been represented by way of example.

Appendix A: Names of Table 1 Compound Numbers III-a-

1: 4-(2-Amino-5-phenyl-pyrimidin-4-yl)-1H-pyrrole-2-carboxylic acid dimethylamide;

2: {4-[2-Amino-5-(3-chloro-phenyl)-pyrimidin-4-yl]-1H-pyrrol-2-yl}-pyrrolidin-1-yl-methanone;

3: {4-[2-Amino-5-(3-chloro-2-fluoro-phenyl)-pyrimidin-4-yl]-1H-pyrrol-2-yl}-pyrrolidin-1-yl-methanone;

4: 4-(2-Amino-5-phenyl-pyrimidin-4-yl)-1H-pyrrole-2-carboxylic acid (2-pyridin-3-yl-ethyl)-amide;

5: [4-(2-Amino-5-phenyl-pyrimidin-4-yl)-1H-pyrrol-2-yl]-morpholin-4-yl-methanone;

6: [4-(2-Amino-5-phenyl-pyrimidin-4-yl)-1H-pyrrol-2-yl]-[1,4']bipiperidinyl-1'-yl-methanone;

7: {4-[2-Amino-5-(3,4-dimethoxy-phenyl)-pyrimidin-4-yl]-1H-pyrrol-2-yl}-(3-hydroxy-piperidin-1-yl)-methanone;

8: {4-[2-Amino-5-(3,4-dimethoxy-phenyl)-pyrimidin-4-yl]-1H-pyrrol-2-yl}-[1,4']bipiperidinyl-1'-yl-methanone;

9: [4-(2-Amino-5-m-tolyl-pyrimidin-4-yl)-1H-pyrrol-2-yl]-[1,4']bipiperidinyl-1'-yl-methanone;

10: {4-[2-Amino-5-(3-chloro-2-fluoro-phenyl)-pyrimidin-4-yl]-1H-pyrrol-2-yl}-[1,4']bipiperidinyl-1'-yl-methanone;

11: [4-(2-Amino-5-m-tolyl-pyrimidin-4-yl)-1H-pyrrol-2-yl]-(4-hydroxy-piperidin-1-yl)-methanone;

12: [4-(2-Amino-5-phenyl-pyrimidin-4-yl)-1H-pyrrol-2-yl]-[4-(2-fluoro-phenyl)-piperazin-1-yl]-methanone;

13: [4-(2-Amino-5-phenyl-pyrimidin-4-yl)-1H-pyrrol-2-yl]-(4-phenyl-piperazin-1-yl)-methanone;

14: [4-(2-Amino-5-phenyl-pyrimidin-4-yl)-1H-pyrrol-2-yl]-[4-(4-fluoro-phenyl)-3,6-dihydro-2H-pyridin-1-yl]-methanone;

15: [4-(2-Amino-5-phenyl-pyrimidin-4-yl)-1H-pyrrol-2-yl]-(4-pyridin-2-yl-piperazin-1-yl)-methanone;

16: {4-[2-Amino-5-(3,4-dimethoxy-phenyl)-pyrimidin-4-yl]-1H-pyrrol-2-yl}-morpholin-4-yl-methanone;

17: 4-[2-Amino-5-(3,4-dimethoxy-phenyl)-pyrimidin-4-yl]-1H-pyrrole-2-carboxylic acid (2-pyridin-3-yl-ethyl)-amide;

18: [4-(2-Amino-5-m-tolyl-pyrimidin-4-yl)-1H-pyrrol-2-yl]-morpholin-4-yl-methanone;

19: 4-(2-Amino-5-m-tolyl-pyrimidin-4-yl)-1H-pyrrole-2-carboxylic acid (2-pyridin-3-yl-ethyl)-amide;

20: 4-[2-Amino-5-(3-chloro-phenyl)-pyrimidin-4-yl]-1H-pyrrole-2-carboxylic acid (2-pyridin-3-yl-ethyl)-amide;

21: {4-[2-Amino-5-(3-chloro-phenyl)-pyrimidin-4-yl]-1H-pyrrol-2-yl}-[4-(2-fluoro-phenyl)-piperazin-1-yl]-methanone;

22: {4-[2-Amino-5-(3-chloro-phenyl)-pyrimidin-4-yl]-1H-pyrrol-2-yl}-(4-phenyl-piperazin-1-yl)-methanone;

23: {4-[2-Amino-5-(3-chloro-phenyl)-pyrimidin-4-yl]-1H-pyrrol-2-yl}-[4-(4-fluoro-phenyl)-3,6-dihydro-2H-pyridin-1-yl]-methanone;

24: {4-[2-Amino-5-(3-chloro-phenyl)-pyrimidin-4-yl]-1H-pyrrol-2-yl}-(3,4-dihydro-1H-isoquinolin-2-yl)-methanone;

25: {4-[2-Amino-5-(3-chloro-phenyl)-pyrimidin-4-yl]-1H-pyrrol-2-yl}-(4-pyridin-2-yl-piperazin-1-yl)-methanone;

26: {4-[2-Amino-5-(3-chloro-2-fluoro-phenyl)-pyrimidin-4-yl]-1H-pyrrol-2-yl}-morpholin-4-yl-methanone;

27: {4-[2-Amino-5-(3-chloro-phenyl)-pyrimidin-4-yl]-1H-pyrrol-2-yl}-(4-hydroxy-piperidin-1-yl)-methanone;

28: {4-[2-Amino-5-(3-chloro-phenyl)-pyrimidin-4-yl]-1H-pyrrol-2-yl}-[1,4']bipiperidinyl-1'-yl-methanone;

29: 4-(2-Amino-5-phenyl-pyrimidin-4-yl)-1H-pyrrole-2-carboxylic acid benzyl-methyl-amide;

30: [4-(2-Amino-5-phenyl-pyrimidin-4-yl)-1H-pyrrol-2-yl]-[4-(4-methoxy-phenyl)-piperazin-1-yl]-methanone;

31: [4-(2-Amino-5-phenyl-pyrimidin-4-yl)-1H-pyrrol-2-yl]-(2-hydroxymethyl-piperidin-1-yl)-methanone;

32: [4-(2-Amino-5-phenyl-pyrimidin-4-yl)-1H-pyrrol-2-yl]-(3,4-dihydro-1H-isoquinolin-2-yl)-methanone;

33: 4-[2-Amino-5-(3,4-dimethoxy-phenyl)-pyrimidin-4-yl]-1H-pyrrole-2-carboxylic acid benzyl-methyl-amide;

34: {4-[2-Amino-5-(3,4-dimethoxy-phenyl)-pyrimidin-4-yl]-1H-pyrrol-2-yl}-[4-(4-fluoro-phenyl)-3,6-dihydro-2H-pyridin-1-yl]-methanone;

35: {4-[2-Amino-5-(3,4-dimethoxy-phenyl)-pyrimidin-4-yl]-1H-pyrrol-2-yl}-(3,4-dihydro-1H-isoquinolin-2-yl)-methanone;

36: 4-(2-Amino-5-m-tolyl-pyrimidin-4-yl)-1H-pyrrole-2-carboxylic acid benzyl-methyl-amide;

37: [4-(2-Amino-5-m-tolyl-pyrimidin-4-yl)-1H-pyrrol-2-yl]-(4-phenyl-piperazin-1-yl)-methanone;

38: [4-(2-Amino-5-m-tolyl-pyrimidin-4-yl)-1H-pyrrol-2-yl]-(4-methyl-[1,4]diazepan-1-yl)-methanone;

39: [4-(2-Amino-5-m-tolyl-pyrimidin-4-yl)-1H-pyrrol-2-yl]-(3,4-dihydro-1H-isoquinolin-2-yl)-methanone;

40: 4-[2-Amino-5-(3-chloro-phenyl)-pyrimidin-4-yl]-1H-pyrrole-2-carboxylic acid benzyl-methyl-amide;

41: {4-[2-Amino-5-(3-chloro-phenyl)-pyrimidin-4-yl]-1H-pyrrol-2-yl}-(4-methyl-[1,4]diazepan-1-yl)-methanone;

42: 4-[2-Amino-5-(3-chloro-2-fluoro-phenyl)-pyrimidin-4-yl]-1H-pyrrole-2-carboxylic acid benzyl-methyl-amide;

43: {4-[2-Amino-5-(3-chloro-phenyl)-pyrimidin-4-yl]-1H-pyrrol-2-yl}-[2-(2-hydroxy-ethyl)-piperidin-1-yl]-methanone;

44: {4-[2-Amino-5-(3-chloro-2-fluoro-phenyl)-pyrimidin-4-yl]-1H-pyrrol-2-yl}-(4-phenyl-piperazin-1-yl)-methanone;

45: [4-(2-Amino-5-m-tolyl-pyrimidin-4-yl)-1H-pyrrol-2-yl]-[4-(2-fluoro-phenyl)-piperazin-1-yl]-methanone;

46: [4-(2-Amino-5-m-tolyl-pyrimidin-4-yl)-1H-pyrrol-2-yl]-(3-hydroxy-piperidin-1-yl)-methanone;

47: [4-(2-Amino-5-m-tolyl-pyrimidin-4-yl)-1H-pyrrol-2-yl]-[4-(4-methoxy-phenyl)-piperazin-1-yl]-methanone;

48: [4-(2-Amino-5-m-tolyl-pyrimidin-4-yl)-1H-pyrrol-2-yl]-[4-(4-fluoro-phenyl)-3,6-dihydro-2H-pyridin-1-yl]-methanone;

49: {4-[2-Amino-5-(3-chloro-2-fluoro-phenyl)-pyrimidin-4-yl]-1H-pyrrol-2-yl}-[4-(2-fluoro-phenyl)-piperazin-1-yl]-methanone;

50: {4-[2-Amino-5-(3-chloro-2-fluoro-phenyl)-pyrimidin-4-yl]-1H-pyrrol-2-yl}-[4-(4-methoxy-phenyl)-piperazin-1-yl]-methanone;

51: {4-[2-Amino-5-(3-chloro-2-fluoro-phenyl)-pyrimidin-4-yl]-1H-pyrrol-2-yl}-(4-methyl-[1,4]diazepan-1-yl)-methanone;

52: 1-(4-{4-[2-Amino-5-(3-chloro-2-fluoro-phenyl)-pyrimidin-4-yl]-1H-pyrrole-2-carbonyl}-piperazin-1-yl)-ethanone;

53: {4-[2-Amino-5-(3-chloro-2-fluoro-phenyl)-pyrimidin-4-yl]-1H-pyrrol-2-yl}-(3,4-dihydro-1H-isoquinolin-2-yl)-methanone;

54: {4-[2-Amino-5-(3-chloro-phenyl)-pyrimidin-4-yl]-1H-pyrrol-2-yl}-(3-hydroxy-piperidin-1-yl)-methanone;

55: [4-(2-Amino-5-phenyl-pyrimidin-4-yl)-1H-pyrrol-2-yl]-(4-methyl-[1,4]diazepan-1-yl)-methanone;

56: 1-(4-{4-[2-Amino-5-(3,4-dimethoxy-phenyl)-pyrimidin-4-yl]-1H-pyrrole-2-carbonyl}-piperazin-1-yl)-ethanone;

57: {4-[2-Amino-5-(3,4-dimethoxy-phenyl)-pyrimidin-4-yl]-1H-pyrrol-2-yl}-(4-methyl-[1,4]diazepan-1-yl)-methanone;

58: [4-(2-Amino-5-phenyl-pyrimidin-4-yl)-1H-pyrrol-2-yl]-(3-hydroxy-piperidin-1-yl)-methanone;

59: 4-[2-Amino-5-(3-chloro-phenyl)-pyrimidin-4-yl]-1H-pyrrole-2-carboxylic acid methyl-(2-pyridin-2-yl-ethyl)-amide;

60: [4-(2-Amino-5-m-tolyl-pyrimidin-4-yl)-1H-pyrrol-2-yl]-[2-(2-hydroxy-ethyl)-piperidin-1-yl]-methanone;

61: {4-[2-Amino-5-(3-chloro-2-fluoro-phenyl)-pyrimidin-4-yl]-1H-pyrrol-2-yl}-[2-(2-hydroxy-ethyl)-piperidin-1-yl]-methanone;

62: 4-[2-Amino-5-(3-chloro-2-fluoro-phenyl)-pyrimidin-4-yl]-1H-pyrrole-2-carboxylic acid (2-hydroxy-1-methyl-2-phenyl-ethyl)-methyl-amide;

63: {4-[2-Amino-5-(3-chloro-2-fluoro-phenyl)-pyrimidin-4-yl]-1H-pyrrol-2-yl}-(4-pyridin-2-yl-piperazin-1-yl)-methanone;

64: [4-(2-Amino-5-phenyl-pyrimidin-4-yl)-1H-pyrrol-2-yl]-(4-hydroxy-piperidin-1-yl)-methanone;

65: {4-[2-Amino-5-(3,4-dimethoxy-phenyl)-pyrimidin-4-yl]-1H-pyrrol-2-yl}-(4-hydroxy-piperidin-1-yl)-methanone;

66: {4-[2-Amino-5-(3-chloro-2-fluoro-phenyl)-pyrimidin-4-yl]-1H-pyrrol-2-yl}-(4-hydroxy-piperidin-1-yl)-methanone;

67: {4-[2-Amino-5-(3,4-dimethoxy-phenyl)-pyrimidin-4-yl]-1H-pyrrol-2-yl}-(4-pyridin-2-yl-piperazin-1-yl)-methanone;

68: {4-[2-Amino-5-(3-chloro-phenyl)-pyrimidin-4-yl]-1H-pyrrol-2-yl}-[4-(2-hydroxy-ethyl)-piperazin-1-yl]-methanone;

69: 1-{4-[4-(2-Amino-5-m-tolyl-pyrimidin-4-yl)-1H-pyrrole-2-carbonyl]-piperazin-1-yl}-ethanone;

70: {4-[2-Amino-5-(3,4-dimethoxy-phenyl)-pyrimidin-4-yl]-1H-pyrrol-2-yl}-[4-(2-fluoro-phenyl)-piperazin-1-yl]-methanone;

71: [4-(2-Amino-5-phenyl-pyrimidin-4-yl)-1H-pyrrol-2-yl]-pyrrolidin-1-yl-methanone;

72: {4-[2-Amino-5-(3-chloro-phenyl)-pyrimidin-4-yl]-1H-pyrrol-2-yl}-morpholin-4-yl-methanone;

73: 4-(2-Amino-5-methyl-pyrimidin-4-yl)-1H-pyrrole-2-carboxylic acid benzylamide;

74: 4-(2-Amino-5-methyl-pyrimidin-4-yl)-1H-pyrrole-2-carboxylic acid 3,4-difluoro-benzylamide;

75: 4-(2-Amino-5-methyl-pyrimidin-4-yl)-1H-pyrrole-2-carboxylic acid (2-hydroxy-1-phenyl-ethyl)-amide;

76: 4-(2-Amino-5-methyl-pyrimidin-4-yl)-1H-pyrrole-2-carboxylic acid 4-fluoro-benzylamide;

77: 4-(2-Amino-5-methyl-pyrimidin-4-yl)-1H-pyrrole-2-carboxylic acid 3-chloro-benzylamide;

78: 4-(2-Amino-5-methyl-pyrimidin-4-yl)-1H-pyrrole-2-carboxylic acid 4-methoxy-benzylamide;

79: 4-(2-Amino-5-methyl-pyrimidin-4-yl)-1H-pyrrole-2-carboxylic acid 3-chloro-4-fluoro-benzylamide;

80: 4-(2-Amino-5-methyl-pyrimidin-4-yl)-1H-pyrrole-2-carboxylic acid (tetrahydro-furan-2-ylmethyl)-amide;

81: 4-(2-Amino-5-methyl-pyrimidin-4-yl)-1H-pyrrole-2-carboxylic acid (tetrahydro-furan-2-ylmethyl)-amide;

82: 4-(2-Amino-5-methyl-pyrimidin-4-yl)-1H-pyrrole-2-carboxylic acid (3-hydroxy-1-phenyl-propyl)-amide;

83: 4-(2-Amino-5-methyl-pyrimidin-4-yl)-1H-pyrrole-2-carboxylic acid (3-hydroxy-1-phenyl-propyl)-amide;

84: 4-(2,5-Diamino-pyrimidin-4-yl)-1H-pyrrole-2-carboxylic acid 3-chloro-4-fluoro-benzylamide;

85: 4-(2-Amino-5-methylamino-pyrimidin-4-yl)-1H-pyrrole-2-carboxylic acid 3-chloro-4-fluoro-benzylamide;

86: 4-(5-Acetylamino-2-amino-pyrimidin-4-yl)-1H-pyrrole-2-carboxylic acid 3-chloro-4-fluoro-benzylamide;

87: 4-[2-Amino-5-(3-methyl-ureido)-pyrimidin-4-yl]-1H-pyrrole-2-carboxylic acid 3-chloro-4-fluoro-benzylamide;

88: 4-(2-Amino-5-hydroxy-pyrimidin-4-yl)-1H-pyrrole-2-carboxylic acid 3-chloro-4-fluoro-benzylamide;

89: 4-(2-Amino-5-methylaminomethyl-pyrimidin-4-yl)-1H-pyrrole-2-carboxylic acid 3-chloro-4-fluoro-benzylamide;

90: 4-(2-Amino-5-hydroxymethyl-pyrimidin-4-yl)-1H-pyrrole-2-carboxylic acid 3-chloro-4-fluoro-benzylamide;

91: 4-[2-Cyclohexylamino-5-(3-methyl-ureido)-pyrimidin-4-yl]-1H-pyrrole-2-carboxylic acid 3-chloro-4-fluoro-benzylamide;

92: 4-[2-Acetylamino-5-(3-methyl-ureido)-pyrimidin-4-yl]-1H-pyrrole-2-carboxylic acid 3-chloro-4-fluoro-benzylamide;

93: 4-(5-Hydroxy-2-methanesulfonylamino-pyrimidin-4-yl)-1H-pyrrole-2-carboxylic acid 3-chloro-4-fluoro-benzylamide;

94: 4-(2-Amino-5-methanesulfonyl-pyrimidin-4-yl)-1H-pyrrole-2-carboxylic acid 3-chloro-4-fluoro-benzylamide;

95: 4-(2-Amino-5-hydroxymethyl-pyrimidin-4-yl)-1H-pyrrole-2-carboxylic acid 3,4-difluoro-benzylamide;

96: 4-(2-Cyclohexylamino-5-methyl-pyrimidin-4-yl)-1H-pyrrole-2-carboxylic acid 3,4-difluoro-benzylamide;

97: 4-[2-Amino-5-(3,5-dichloro-phenyl)-pyrimidin-4-yl]-1H-pyrrole-2-carboxylic acid (pyridin-4-ylmethyl)-amide;

98: 4-[5-(3,5-Dichloro-phenyl)-2-phenylamino-pyrimidin-4-yl]-1H-pyrrole-2-carboxylic acid 3-trifluoromethyl-benzylamide;

99: 4-[2-Amino-5-(3,5-dichloro-phenyl)-pyrimidin-4-yl]-1H-pyrrole-2-carboxylic acid (2-hydroxy-1-phenyl-ethyl)-amide;

100: 4-[2-Amino-5-(3,5-dichloro-phenyl)-pyrimidin-4-yl]-1H-pyrrole-2-carboxylic acid (benzo[1,3]dioxol-5-ylmethyl)-amide;

101: 4-[2-Amino-5-(3,5-dichloro-phenyl)-pyrimidin-4-yl]-1H-pyrrole-2-carboxylic acid (2-dimethylamino-2-pyridin-3-yl-ethyl)-amide;

102: 4-[2-Amino-5-(3,5-dichloro-phenyl)-pyrimidin-4-yl]-1H-pyrrole-2-carboxylic acid 4-methanesulfonyl-benzylamide;

103: 4-[5-(3,5-Dichloro-phenyl)-2-phenylamino-pyrimidin-4-yl]-1H-pyrrole-2-carboxylic acid (benzo[1,3]dioxol-5-ylmethyl)-amide;

104: 4-[5-(3,5-Dichloro-phenyl)-2-phenylamino-pyrimidin-4-yl]-1H-pyrrole-2-carboxylic acid (2-morpholin-4-yl-2-pyridin-3-yl-ethyl)-amide;

105: 4-[2-Amino-5-(3-fluoro-5-trifluoromethyl-phenyl)-pyrimidin-4-yl]-1H-pyrrole-2-carboxylic acid (2-hydroxy-1-phenyl-ethyl)-amide;

106: 4-(2-Amino-5-propyl-pyrimidin-4-yl)-1H-pyrrole-2-carboxylic acid (2-pyridin-3-yl-ethyl)-amide;

107: 4-(2-Amino-5-methyl-pyrimidin-4-yl)-1H-pyrrole-2-carboxylic acid (2-pyridin-3'-yl-ethyl)-amide;

108: 4-(5-Methyl-2-methylamino-pyrimidin-4-yl)-1H-pyrrole-2-carboxylic acid (2-pyridin-3-yl-ethyl)-amide;

109: 4-(2-Methylamino-pyrimidin-4-yl)-1H-pyrrole-2-carboxylic acid (2-pyridin-3-yl-ethyl)-amide;

110: 4-(2-Ethylamino-5-methyl-pyrimidin-4-yl)-1H-pyrrole-2-carboxylic acid (2-dimethylamino-ethyl)-amide;

111: 4-(5-Methyl-2-phenylamino-pyrimidin-4-yl)-1H-pyrrole-2-carboxylic acid propylamide;

112: 4-(5-Methyl-2-phenylamino-pyrimidin-4-yl)-1H-pyrrole-2-carboxylic acid (3-phenyl-propyl)-amide;

113: 4-(2-Ethylamino-5-methyl-pyrimidin-4-yl)-1H-pyrrole-2-carboxylic acid (naphthalen-1-ylmethyl)-amide;

114: 4-(2-Ethylamino-5-methyl-pyrimidin-4-yl)-1H-pyrrole-2-carboxylic acid cyclopropylamide;

115: 4-(2-Ethylamino-pyrimidin-4-yl)-1H-pyrrole-2-carboxylic acid 2-trifluoromethyl-benzylamide;

116: 4-(5-Methyl-2-phenylamino-pyrimidin-4-yl)-1H-pyrrole-2-carboxylic acid (2-hydroxy-1-phenyl-ethyl)-amide;

117: 4-(2-Ethylamino-5-methyl-pyrimidin-4-yl)-1H-pyrrole-2-carboxylic acid (2-hydroxy-1-phenyl-ethyl)-amide;

118: 4-(2-Ethylamino-pyrimidin-4-yl)-1H-pyrrole-2-carboxylic acid (4-methyl-cyclohexyl)-amide;

119: 4-(5-Ethyl-2-phenylamino-pyrimidin-4-yl)-1H-pyrrole-2-carboxylic acid isopropylamide;

120: 4-(5-Methyl-2-phenylamino-pyrimidin-4-yl)-1H-pyrrole-2-carboxylic acid (2-amino-ethyl)-amide;

121: 4-(2-Amino-pyrimidin-4-yl)-1H-pyrrole-2-carboxylic acid benzyl-methyl-amide;

122: 4-(2-Amino-pyrimidin-4-yl)-1H-pyrrole-2-carboxylic acid (2-hydroxy-1-methyl-2-phenyl-ethyl)-methyl-amide;

123: 1-{4-[4-(2-Ethylamino-5-methyl-pyrimidin-4-yl)-1H-pyrrole-2-carbonyl]-piperazin-1-yl}-ethanone;

124: 4-(2-Ethylamino-5-methyl-pyrimidin-4-yl)-1H-pyrrole-2-carboxylic acid (3-phenyl-propyl)-amide;

125: 4-(2-Amino-5-ethyl-pyrimidin-4-yl)-1H-pyrrole-2-carboxylic acid [2-(6-methoxy-1H-indol-3-yl)-ethyl]-amide;

126: 4-(5-Methyl-2-phenylamino-pyrimidin-4-yl)-1H-pyrrole-2-carboxylic acid (2-phenoxy-ethyl)-amide;

127: 4-(5-Methyl-2-phenylamino-pyrimidin-4-yl)-1H-pyrrole-2-carboxylic acid (1-methyl-3-phenyl-propyl)-amide;

128: 4-(5-Methyl-2-methylamino-pyrimidin-4-yl)-1H-pyrrole-2-carboxylic acid (1H-benzoimidazol-2-ylmethyl)-amide;

129: 4-(5-Methyl-2-methylamino-pyrimidin-4-yl)-1H-pyrrole-2-carboxylic acid (1-hydroxymethyl-3-methyl-butyl)-amide;

130: 4-(5-Methyl-2-phenylamino-pyrimidin-4-yl)-1H-pyrrole-2-carboxylic acid [1-hydroxymethyl-2-(1H-imidazol-4-yl)-ethyl]-amide;

131: 4-(2-Amino-5-methyl-pyrimidin-4-yl)-1H-pyrrole-2-carboxylic acid (tetrahydro-furan-2-ylmethyl)-amide;

132: 4-[2-(2-Diethylamino-ethylamino)-5-methyl-pyrimidin-4-yl]-1H-pyrrole-2-carboxylic acid 3i4-difluoro-benzylamide;

133: 4-[5-Methyl-2-(2-piperidin-1-yl-quinazolin-4-ylamino)-pyrimidin-4-yl]-1H-pyrrole-2-carboxylic acid benzylamide;

134: 4-(5-Methyl-2-methylamino-pyrimidin-4-yl)-1H-pyrrole-2-carboxylic acid [1-(3-chloro-4-fluoro-phenyl)-2-hydroxy-ethyl]-amide;

135: 4-(5-Methyl-2-phenylamino-pyrimidin-4-yl)-1H-pyrrole-2-carboxylic acid [1-(3-chloro-4-fluoro-phenyl)-2-hydroxy-ethyl]-amide;

136: 4-[2-(3-Fluoro-phenylamino)-5-methyl-pyrimidin-4-yl]-1H-pyrrole-2-carboxylic acid (2-hydroxy-1-phenyl-ethyl)-amide;

137: 4-[2-(3-Methoxy-phenylamino)-5-methyl-pyrimidin-4-yl]-1H-pyrrole-2-carboxylic acid (2-hydroxy-1-phenyl-ethyl)-amide;

138: 4-[2-(3-Hydroxy-phenylamino)-5-methyl-pyrimidin-4-yl]-1H-pyrrole-2-carboxylic acid (2-hydroxy-1-phenyl-ethyl)-amide;

139: 4-[2-(Benzo[1,3]dioxol-5-ylamino)-5-methyl-pyrimidin-4-yl]-1H-pyrrole-2-carboxylic acid (2-hydroxy-1-phenyl-ethyl)-amide;

140: 4-[5-Methyl-2-(4-sulfamoyl-phenylamino)-pyrimidin-4-yl]-1H-pyrrole-2-carboxylic acid (2-hydroxy-1-phenyl-ethyl)-amide;

141: 4-[2-(3-Benzyloxy-phenylamino)-5-methyl-pyrimidin-4-yl]-1H-pyrrole-2-carboxylic acid (2-hydroxy-1-phenyl-ethyl)-amide;

142: 4-[2-(4-Hydroxy-cyclohexylamino)-5-methyl-pyrimidin-4-yl]-1H-pyrrole-2-carboxylic acid (2-hydroxy-1-phenyl-ethyl)-amide;

143: 4-(5-Cyclohexyl-2-phenylamino-pyrimidin-4-yl)-1H-pyrrole-2-carboxylic acid (2-hydroxy-1-phenyl-ethyl)-amide;

144: 4-(5-Cyclopropyl-2-phenylamino-pyrimidin-4-yl)-1H-pyrrole-2-carboxylic acid (2-hydroxy-1-phenyl-ethyl)-amide;

145: 4-(5-Methyl-2-phenylamino-pyrimidin-4-yl)-1H-pyrrole-2-carboxylic acid [1-(3-fluoro-4-methyl-phenyl)-2-hydroxy-ethyl]-amide;

146: 4-(5-Methyl-2-phenylamino-pyrimidin-4-yl)-1H-pyrrole-2-carboxylic acid [2-hydroxy-1-(3-trifluoromethyl-phenyl)-ethyl]-amide;

147: 4-[2-(3-Fluoro-phenylamino)-5-methyl-pyrimidin-4-yl]-1H-pyrrole-2-carboxylic acid [1-(3-fluoro-4-methyl-phenyl)-2-hydroxy-ethyl]-amide;

148: 4-[2-(3-Fluoro-phenylamino)-5-methyl-pyrimidin-4-yl]-1H-pyrrole-2-carboxylic acid [2-hydroxy-1-(3-trifluoromethyl-phenyl)-ethyl]-amide;

149: 4-[5-Methyl-2-(3-trifluoromethyl-phenylamino)-pyrimidin-4-yl]-1H-pyrrole-2-carboxylic acid (2-hydroxy-1-phenyl-ethyl)-amide;

150: 4-(2-Benzylamino-5-methyl-pyrimidin-4-yl)-1H-pyrrole-2-carboxylic acid (2-hydroxy-1-phenyl-ethyl)-amide;

151: 4-[2-(3,4-Dimethyl-phenylamino)-5-methyl-pyrimidin-4-yl]-1H-pyrrole-2-carboxylic acid (2-hydroxy-1-phenyl-ethyl)-amide;

152: 4-[2-(4-Benzyloxy-phenylamino)-5-methyl-pyrimidin-4-yl]-1H-pyrrole-2-carboxylic acid (2-hydroxy-1-phenyl-ethyl)-amide;

153: 4-(2-Isopropylamino-5-methyl-pyrimidin-4-yl)-1H-pyrrole-2-carboxylic acid (2-hydroxy-1-phenyl-ethyl)-amide;

154: 4-[5-Methyl-2-(2,2,2-trifluoro-ethylamino)-pyrimidin-4-yl]-1H-pyrrole-2-carboxylic acid (2-hydroxy-1-phenyl-ethyl)-amide;

155: 4-[2-(2-Hydroxy-1-phenyl-ethylamino)-5-methyl-pyrimidin-4-yl]-1H-pyrrole-2-carboxylic acid (2-hydroxy-1-phenyl-ethyl)-amide;

156: 4-[2-(2-Methoxy-phenylamino)-5-methyl-pyrimidin-4-yl]-1H-pyrrole-2-carboxylic acid (2-hydroxy-1-phenyl-ethyl)-amide;

157: 4-[5-Methyl-2-(4-trifluoromethoxy-phenylamino)-pyrimidin-4-yl]-1H-pyrrole-2-carboxylic acid (2-hydroxy-1-phenyl-ethyl)-amide;

158: 4-(2-Isobutylamino-5-methyl-pyrimidin-4-yl)-1H-pyrrole-2-carboxylic acid (2-hydroxy-1-phenyl-ethyl)-amide;

159: 4-[2-(Cyclopropylmethyl-amino)-5-methyl-pyrimidin-4-yl]-1H-pyrrole-2-carboxylic acid (2-hydroxy-1-phenyl-ethyl)-amide;

160: 4-(5-Methoxymethyl-2-phenylamino-pyrimidin-4-yl)-1H-pyrrole-2-carboxylic acid (2-hydroxy-1-phenyl-ethyl)-amide;

161: 4-(2-Amino-5-methoxymethyl-pyrimidin-4-yl)-1H-pyrrole-2-carboxylic acid (2-hydroxy-1-phenyl-ethyl)-amide;

162: 4-(2-Cyclopropylamino-5-methyl-pyrimidin-4-yl)-1H-pyrrole-2-carboxylic acid (2-hydroxy-1-phenyl-ethyl)-amide;

163: 4-(5-Methyl-2-propylamino-pyrimidin-4-yl)-1H-pyrrole-2-carboxylic acid (2-hydroxy-1-phenyl-ethyl)-amide;

164: 4-(5-Methoxymethyl-2-phenylamino-pyrimidin-4-yl)-1H-pyrrole-2-carboxylic acid (2-hydroxy-1-phenyl-ethyl)-amide;

165: 4-(5-Hydroxymethyl-2-phenylamino-pyrimidin-4-yl)-1H-pyrrole-2-carboxylic acid (2-hydroxy-1-phenyl-ethyl)-amide;

166: 4-[2-(2-Hydroxy-1-phenyl-ethylamino)-5-methyl-pyrimidin-4-yl]-1H-pyrrole-2-carboxylic acid (2-hydroxy-1-phenyl-ethyl)-amide;

167: 4-(2-Ethylamino-5-methyl-pyrimidin-4-yl)-1H-pyrrole-2-carboxylic acid (2-hydroxy-1-methyl-2-phenyl-ethyl)-amide;

168: 4-(2-Ethylamino-5-methyl-pyrimidin-4-yl)-1H-pyrrole-2-carboxylic acid (2-hydroxy-1-methyl-2-phenyl-ethyl)-amide;

169: 4-(2-Ethylamino-5-methyl-pyrimidin-4-yl)-1H-pyrrole-2-carboxylic acid (2-hydroxy-2-phenyl-ethyl)-amide;

170: 4-(2-Ethylamino-5-methyl-pyrimidin-4-yl)-1H-pyrrole-2-carboxylic acid (2-hydroxy-1-hydroxymethyl-2-phenyl-ethyl)-amide;

171: 4-(2-Ethylamino-5-methyl-pyrimidin-4-yl)-1H-pyrrole-2-carboxylic acid (2-hydroxy-1-hydroxymethyl-2-phenyl-ethyl)-amide;

172: 4-(2-Ethylamino-5-methyl-pyrimidin-4-yl)-1H-pyrrole-2-carboxylic acid (3-hydroxy-1-phenyl-propyl)-amide;

173: 4-(2-Ethylamino-5-methyl-pyrimidin-4-yl)-1H-pyrrole-2-carboxylic acid (3-hydroxy-1-phenyl-propyl)-amide;

174: 4-[2-(1-Hydroxymethyl-cyclopropylamino)-5-methyl-pyrimidin-4-yl]-1H-pyrrole-2-carboxylic acid (2-hydroxy-1-phenyl-ethyl)-amide;

175: 4-[2-(2-Hydroxy-ethylamino)-5-methyl-pyrimidin-4-yl]-1H-pyrrole-2-carboxylic acid (2-hydroxy-1-phenyl-ethyl)-amide;

176: 4-[2-(2-Hydroxy-1-methyl-ethylamino)-5-methyl-pyrimidin-4-yl]-1H-pyrrole-2-carboxylic acid (2-hydroxy-1-phenyl-ethyl)-amide;

177: 4-[2-(2-Hydroxy-propylamino)-5-methyl-pyrimidin-4-yl]-1H-pyrrole-2-carboxylic acid (2-hydroxy-1-phenyl-ethyl)-amide;

178: 4-[2-(2-Hydroxy-propylamino)-5-methyl-pyrimidin-4-yl]-1H-pyrrole-2-carboxylic acid (2-hydroxy-1-phenyl-ethyl)-amide;

179: 4-[2-(2-Hydroxy-cyclohexylamino)-5-methyl-pyrimidin-4-yl]-1H-pyrrole-2-carboxylic acid (2-hydroxy-1-phenyl-ethyl)-amide;

121: 4-[2-(2-Hydroxy-1-methyl-ethylamino)-5-methyl-pyrimidin-4-yl]-1H-pyrrole-2-carboxylic acid (2-hydroxy-1-phenyl-ethyl)-amide;

121: 4-[2-(3-Dimethylamino-phenylamino)-5-methyl-pyrimidin-4-yl]-1H-pyrrole-2-carboxylic acid (2-hydroxy-1-phenyl-ethyl)-amide;

180: 4-(2-Amino-pyrimidin-4-yl)-1H-pyrrole-2-carboxylic acid (2-hydroxy-1-methyl-2-phenyl-ethyl)-methyl-amide;

181: 4-(2-Amino-pyrimidin-4-yl)-1H-pyrrole-2-carboxylic acid (2-hydroxy-1-methyl-2-phenyl-ethyl)-ethyl-amide;

183: 4-(2-Amino-pyrimidin-4-yl)-1H-pyrrole-2-carboxylic acid (2-hydroxy-2-phenyl-ethyl)-methyl-amide;

184: {[4-(2-Ethylamino-5-methyl-pyrimidin-4-yl)-1H-pyrrole-2-carbonyl]-amino}-phenyl-acetic acid methyl ester;

186: 4-(2-Amino-pyrimidin-4-yl)-1H-pyrrole-2-carboxylic acid (2-hydroxy-1-methyl-2-phenyl-ethyl)-methyl-amide;

187: 4-(2-Ethylamino-5-methoxymethyl-pyrimidin-4-yl)-1H-pyrrole-2-carboxylic acid (2-hydroxy-1-phenyl-ethyl)-amide;

188: 4-(2-Ethylamino-5-methyl-pyrimidin-4-yl)-1H-pyrrole-2-carboxylic acid (2-hydroxy-1-pyridin-3-yl-ethyl)-amide;

189: 4-(2-Ethylamino-5-hydroxymethyl-pyrimidin-4-yl)-1H-pyrrole-2-carboxylic acid (2-hydroxy-1-phenyl-ethyl)-amide;

190: 4-(2-Ethylamino-5-methyl-pyrimidin-4-yl)-1H-pyrrole-2-carboxylic acid [1-(3-fluoro-5-trifluoromethyl-phenyl)-2-hydroxy-ethyl]-amide;

191: 4-(2-Ethylamino-5-methyl-pyrimidin-4-yl)-1H-pyrrole-2-carboxylic acid [1-(3-fluoro-phenyl)-2-hydroxy-ethyl]-amide;

192: 4-(2-Ethylamino-5-methyl-pyrimidin-4-yl)-1H-pyrrole-2-carboxylic acid [1-(2-fluoro-phenyl)-2-hydroxy-ethyl]-amide;

193: 4-[2-(2-Cyclopropyl-1-hydroxymethyl-ethylamino)-5-methyl-pyrimidin-4-yl]-1H-pyrrole-2-carboxylic acid (2-hydroxy-1-phenyl-ethyl)-amide;

194: 4-[2-(2,3-Dimethyl-phenylamino)-5-methyl-pyrimidin-4-yl]-1H-pyrrole-2-carboxylic acid (2-hydroxy-1-phenyl-ethyl)-amide;

195: 4-(2-Ethoxyamino-5-methyl-pyrimidin-4-yl)-1H-pyrrole-2-carboxylic acid (2-hydroxy-1-phenyl-ethyl)-amide;

196: 4-[2-(1-Hydroxymethyl-2-methyl-propylamino)-5-methyl-pyrimidin-4-yl]-1H-pyrrole-2-carboxylic acid (2-hydroxy-1-phenyl-ethyl)-amide;

197: 4-(2-Ethylamino-5-methyl-pyrimidin-4-yl)-1H-pyrrole-2-carboxylic acid (2-oxo-1-phenyl-propyl)-amide;

198: 4-(2-Ethylamino-5-methyl-pyrimidin-4-yl)-1H-pyrrole-2-carboxylic acid [2-hydroxy-1-(3-trifluoromethyl-phenyl)-ethyl]-amide;

199: 4-[2-(3-Fluoro-phenylamino)-5-methyl-pyrimidin-4-yl]-1H-pyrrole-2-carboxylic acid [2-hydroxy-1-(3-trifluoromethyl-phenyl)-ethyl]-amide;

200: 4-[2-(2-Chloro-phenylamino)-5-methyl-pyrimidin-4-yl]-1H-pyrrole-2-carboxylic acid [2-hydroxy-1-(3-trifluoromethyl-phenyl)-ethyl]-amide;

201: 4-[2-(2-Hydroxy-1-phenyl-ethylamino)-5-methyl-pyrimidin-4-yl]-1H-pyrrole-2-carboxylic acid [2-hydroxy-1-(3-trifluoromethyl-phenyl)-ethyl)-amide;

200: 4-[2-(3-Dimethylamino-phenylamino)-5-methyl-pyrimidin-4-yl]-1H-pyrrole-2-carboxylic acid [2-hydroxy-1-(3-trifluoromethyl-phenyl)-ethyl]-amide;

202: 4-(2-Cyclopropylamino-5-methyl-pyrimidin-4-yl)-1H-pyrrole-2-carboxylic acid [2-hydroxy-1-(3-trifluoromethyl-phenyl)-ethyl]-amide;

203: 4-(2-Cyclopropylamino-5-methyl-pyrimidin-4-yl)-1H-pyrrole-2-carboxylic acid [2-hydroxy-1-(2-methoxy-phenyl)-ethyl]-amide;

204: 4-(2-Cyclopropylamino-5-methyl-pyrimidin-4-yl)-1H-pyrrole-2-carboxylic acid [1-(3-chloro-phenyl)-2-hydroxy-ethyl]-amide;

205: 4–1(2-Cyclopropylamino-5-methyl-pyrimidin-4-yl)-1H-pyrrole-2-carboxylic acid (2-hydroxy-1-m-tolyl-ethyl)-amide;

206: 4-(2-Methoxyamino-5-methyl-pyrimidin-4-yl)-1H-pyrrole-2-carboxylic acid (2-hydroxy-1-phenyl-ethyl)-amide;

207: 4-(2-Isopropoxyamino-5-methyl-pyrimidin-4-yl)-1H-pyrrole-2-carboxylic acid (2-hydroxy-1-phenyl-ethyl)-amide;

208: 4-[2-(3-Dimethylamino-phenylamino)-5-methyl-pyrimidin-4-yl]-1H-pyrrole-2-carboxylic acid (2-hydroxy-1-m-tolyl-ethyl))-amide;

209: 4-[2-(2-Chloro-phenylamino)-5-methyl-pyrimidin-4-yl]-1H-pyrrole-2-carboxylic acid (2-hydroxy-1-m-tolyl-ethyl)-amide;

210: 4-[2-(2-Hydroxy-1-phenyl-ethylamino)-5-methyl-pyrimidin-4-yl]-1H-pyrrole-2-carboxylic acid (2-hydroxy-1-m-tolyl-ethyl)-amide;

211: 4-[2-(2,3-Dimethyl-phenylamino)-5-methyl-pyrimidin-4-yl]-1H-pyrrole-2-carboxylic acid (2-hydroxy-1-m-tolyl-ethyl)-amide;

212: 4-[2-(3-Fluoro-phenylamino)-5-methyl-pyrimidin-4-yl]-1H-pyrrole-2-carboxylic acid (2-hydroxy-1-m-tolyl-ethyl)-amide;

213: 4-(2-Acetylamino-5-methyl-pyrimidin-4-yl)-1H-pyrrole-2-carboxylic acid (2-hydroxy-1-phenyl-ethyl)-amide;

214: 4-(5-Methyl-2-o-tolylamino-pyrimidin-4-yl)-1H-pyrrole-2-carboxylic acid (2-hydroxy-1-phenyl-ethyl)-amide;

215: 4-[5-Methyl-2-(pyridin-3-ylamino)-pyrimidin-4-yl]-1H-pyrrole-2-carboxylic acid (2-hydroxy-1-phenyl-ethyl)-amide;

216: 4-{5-Methyl-2-[(tetrahydro-furan-2-ylmethyl)-amino]-pyrimidin-4-yl}-1H-pyrrole-2-carboxylic acid (2-hydroxy-1-phenyl-ethyl)-amide;

217: 4-{5-Methyl-2-((tetrahydro-furan-2-ylmethyl)-amino]-pyrimidin-4-yl}-1H-pyrrole-2-carboxylic acid (2-hydroxy-1-phenyl-ethyl)-amide;

218: N'-{4-[5-(2-Hydroxy-1-phenyl-ethylcarbamoyl)-1H-pyrrol-3-yl]-5-methyl-pyrimidin-2-yl}-hydrazinecarboxylic acid ethyl ester;

219: 4-{5-Methyl-2-[(pyridin-3-ylmethyl)-amino]-pyrimidin-4-yl}-1H-pyrrole-2-carboxylic acid (2-hydroxy-1-phenyl-ethyl)-amide;

220: 4-(2-Cyclopropylmethoxyamino-5-methyl-pyrimidin-4-yl)-1H-pyrrole-2-carboxylic acid (2-hydroxy-1-phenyl-ethyl)-amide;

221: 4-[2-(Isoxazol-3-ylamino)-5-methyl-pyrimidin-4-yl]-1H-pyrrole-2-carboxylic acid (2-hydroxy-1-phenyl-ethyl)-amide;

222: 4-[2-(2-Hydroxy-1-methyl-ethylamino)-5-methyl-pyrimidin-4-yl]-1H-pyrrole-2-carboxylic acid (2-hydroxy-1-m-tolyl-ethyl)-amide;

223: 4-(5-Methyl-2-o-tolylamino-pyrimidin-4-yl)-1H-pyrrole-2-carboxylic acid (2-hydroxy-1-m-tolyl-ethyl)-amide;

224: 4-(5-Methyl-2-o-tolylamino-pyrimidin-4-yl)-1H-pyrrole-2-carboxylic acid [1-(3-chloro-phenyl)-2-hydroxy-ethyl]-amide;

225: 4-[2-(2-Hydroxy-ethoxyamino)-5-methyl-pyrimidin-4-yl]-1H-pyrrole-2-carboxylic acid (2-hydroxy-1-phenyl-ethyl)-amide;

226: 4-[2-(N',N'-Dimethyl-hydrazino)-5-methyl-pyrimidin-4-yl]-1H-pyrrole-2-carboxylic acid (2-hydroxy-1-phenyl-ethyl)-amide;

227: 4-[5-Methyl-2-(2-trifluoromethyl-phenylamino)-pyrimidin-4-yl]-1H-pyrrole-2-carboxylic acid (2-hydroxy-1-phenyl-ethyl)-amide;

228: 4-[5-Methyl-2-(morpholin-4-ylamino)-pyrimidin-4-yl]-1H-pyrrole-2-carboxylic acid (2-hydroxy-1-phenyl-ethyl)-amide;

229: 4-[5-Methyl-2-(5-methyl-isoxazol-3-ylamino)-pyrimidin-4-yl]-1H-pyrrole-2-carboxylic acid (2-hydroxy-1-phenyl-ethyl)-amide;

230: 4-{2-[1-(3-Chloro-4-fluoro-phenyl)-2-hydroxy-ethylamino]-5-methyl-pyrimidin-4-yl}-1H-pyrrole-2-carboxylic acid (2-hydroxy-1-phenyl-ethyl)-amide;

231: 4-(5-Methyl-2-phenylamino-pyrimidin-4-yl)-1H-pyrrole-2-carboxylic acid [1-(3-fluoro-phenyl)-2-hydroxy-ethyl)-amide;

232: 4-[2-(1-Hydroxymethyl-propylamino)-5-methyl-pyrimidin-4-yl]-1H-pyrrole-2-carboxylic acid (1-(3-chloro-phenyl)-2-hydroxy-ethyl]-amide;

233: 4-[2-(2-Hydroxy-1-hydroxymethyl-ethylamino)-5-methyl-pyrimidin-4-yl]-1H-pyrrole-2-carboxylic acid [1-(3-chloro-phenyl)-2-hydroxy-ethyl]-amide;

234: 4-[2-(1-Hydroxymethyl-propylamino)-5-methyl-pyrimidin-4-yl]-1H-pyrrole-2-carboxylic acid (2-hydroxy-1-m-tolyl-ethyl)-amide;

235: 4-[2-(2-Hydroxy-1-hydroxymethyl-ethylamino)-5-methyl-pyrimidin-4-yl]-1H-pyrrole-2-carboxylic acid (2-hydroxy-1-phenyl-ethyl)-amide;

236: 4-[2-(1-Hydroxymethyl-propylamino)-5-methyl-pyrimidin-4-yl]-1H-pyrrole-2-carboxylic acid (2-hydroxy-1-phenyl-ethyl)-amide;

237: 4-[5-Methyl-2-(2-methyl-cyclopropylamino)-pyrimidin-4-yl]-1H-pyrrole-2-carboxylic acid (2-hydroxy-1-phenyl-ethyl)-amide; and 238: 4-(2-Cyanoamino-5-methyl-pyrimidin-4-yl)-1H-pyrrole-2-carboxylic acid (2-hydroxy-1-phenyl-ethyl)-amide.

We claim:

1. A compound of formula I':

I'

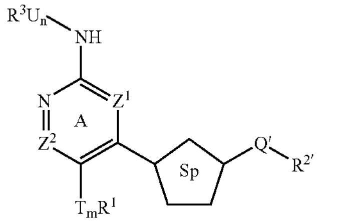

or a pharmaceutically acceptable salt thereof, wherein:

Sp is a 5-membered heteroaromatic ring selected from pyrrole, imidazole, pyrazole, triazole, oxazole, isoxazole, 1,3-thiazole, 1,2-thiazole, or furan, wherein Ring A and $Q'R^{2'}$ are attached to Sp at non-adjacent positions; and wherein Sp has up to two $R^6$ substituents, provided that two substitutable carbon ring atoms in Sp are not simultaneously substituted by $R^6$;

$Z^1$ is CH and $Z^2$ is CH;

T is a linker group selected from —NH—, —$CH_2$—, —CO—, or a saturated or unsaturated $C_{1-6}$ alkylidene chain which is optionally substituted, and wherein up to two saturated carbons of the chain are optionally replaced by —C(O)—, —C(O)C(O)—, —$CONR^7$—, —$CONR^7NR^7$—, —$CO_2$—, —OC(O)—, —$NR^7CO_2$—, —O—, —$NR^7CONR^7$—, —OC(O)$NR^7$—, —$NR^7NR^7$—, —$NR^7CO$—, —S—, —SO—, —$SO_2$—, —$NR^7$—, —$SO_2NR^7$—, or —$NR^7SO_2$—;

Q' is selected from —$CO_2$—, —C(O)$NR^7$— or —$SO_2NR^7$—;

U is selected from —$NR^7$—, —$NR^7CO$—, —$NR^7CONR^7$—, —$NR^7CO_2$—, —O—, —$CONR^7$—, —CO—, —$CO_2$—, —OC(O)—, —$NR^7SO_2$—, —$SO_2NR^7$—, —$NR^7SO_2NR^7$—, or —$SO_2$—;

m and n are each independently selected from zero or one;

$R^1$ is selected from hydrogen, CN, halogen, R, $N(R^7)_2$, OR, or OH;

$R^{2'}$ is selected from —$(CH_2)_yCH(R^5)_2$ or —$(CH_2)_yCH(R^8)CH(R^5)_2$;

y is 0–6;

$R^3$ is selected from $R^7$, R, —$(CH_2)_yCH(R^8)R$, CN, —$(CH_2)_yCH(R^8)CH(R^5)_2$, or —$(CH_2)_yCH(R^8)N(R^4)_2$;

each R is independently selected from an optionally substituted group selected from $C_{1-6}$ aliphatic, $C_{6-10}$ aryl, a heteroaryl ring having 5–10 ring atoms, or a heterocyclyl ring having 3–10 ring atoms;

each $R^4$ is independently selected from R, $R^7$, —$COR^7$, —$CO_2R$, —$CON(R^7)_2$, —$SO_2R^7$, —$(CH_2)_yR^5$, or —$(CH_2)_yCH(R^5)_2$;

each $R^5$ is independently selected from R, OR, $CO_2R$, $(CH_2)_yN(R^7)_2$, $N(R^7)_2$, $OR^7$, $SR^7$, $NR^7COR^7$, $NR^7CON(R^7)_2$, $CON(R^7)_2$, $SO_2R^7$, $NR^7SO_2R^7$, $COR^7$, CN, or $SO_2N(R^7)_2$;

each $R^6$ is independently selected from $R^7$, F, Cl, $OR^7$, $SR^7$, $NR^7COR^7$, $NR^7CON(R^7)_2$; $CON(R^7)_2$, $SO_2R^7$, $NR^7SO_2R^7$, $COR^7$, CN, or $SO_2N(R^7)_2$;

each $R^7$ is independently selected from hydrogen or an optionally substituted $C_{1-6}$ aliphatic group, or two $R^7$ on the same nitrogen are taken together with the nitrogen to form a 5–8 membered heterocyclyl or heteroaryl ring;

$R^8$ is selected from R, $(CH_2)_wOR^7$, $(CH_2)_wN(R^4)_2$, or $(CH_2)_wSR^7$; and each w is independently selected from 0–4.

2. The compound according to claim 1, wherein said compound has one or more features selected from the group consisting of:

(a) $R^3$ is hydrogen, carbocyclyl, —$CH(R^8)R$, or an optionally substituted group selected from $C_{1-4}$ aliphatic, 3–6 membered heterocyclic, or a 5–6 membered aryl or heteroaryl ring;

(b) $T_mR^1$ is hydrogen, amino, OH, 3–6 membered carbocyclyl, or an optionally substituted group selected from $C_{1-6}$ aliphatic or a 5–6 membered aryl or heteroaryl ring; and (c) $R^5$ is R or $OR^7$, wherein R is carbocyclic, or an optionally substituted 5 or 6-membered aryl or heteroaryl ring.

3. The compound according to claim 2, wherein:

(a) $R^3$ is hydrogen, carbocyclyl, —$CH(R^8)R$, or an optionally substituted group selected from $C_{1-4}$ aliphatic, 3–6 membered heterocyclic, or a 5–6 membered aryl or heteroaryl ring;

(b) $T_mR^1$ is hydrogen, amino, OH, 3–6 membered carbocyclyl, or an optionally substituted group selected from $C_{1-6}$ aliphatic or a 5–6 membered aryl or heteroaryl ring; and (c) $R^5$ is R or $OR^7$, wherein R is carbocyclic, or an optionally substituted 5 or 6-membered aryl or heteroaryl ring.

4. The compound according to claim 2, wherein said compound has one or more features selected from the group consisting of:

(a) $R^3$ is selected from hydrogen, methyl, ethyl, propyl, cyclopropyl, cyclohexyl, isopropyl, —$CH(CH_2OH)$phenyl, —$CH(CH_2OH)$ethyl, —$CH(CH_2OH)_2$, —$CH(CH_2OH)$isopropyl, —$CH(CH_2OH)CH_2$cyclopropyl, or an optionally substituted phenyl, benzyl, or isoxazolyl group;

(b) $T_mR^1$ is selected from optionally substituted phenyl, methyl, ethyl, propyl, cyclopropyl, cyclohexyl, $CH_2OCH_3$, $CH_2OH$, OH, $NH_2$, $NHCH_3$, NHAc, NHC(O)$NHCH_3$, or $CH_2NHCH_3$; and (c) $R^5$ is OH, $CH_2OH$, carbocyclic, or an optionally substituted phenyl or pyridyl ring, and Q' is —C(O)NH—.

5. The compound according to claim 4, wherein:

(a) $R^3$ is selected from hydrogen, methyl, ethyl, propyl, cyclopropyl, cyclohexyl, isopropyl, —CH($CH_2OH$)phenyl, —CH($CH_2OH$)ethyl, —CH($CH_2OH)_2$, —CH($CH_2OH$)isopropyl, —CH($CH_2OH$)$CH_2$cyclopropyl, or an optionally substituted phenyl, benzyl, or isoxazolyl group;

(b) $T_mR^1$ is selected from optionally substituted phenyl, methyl, ethyl, propyl, cyclopropyl, cyclohexyl, $CH_2OCH_3$, $CH_2OH$, OH, $NH_2$, $NHCH_3$, NHAc, NHC(O)$NHCH_3$, or $CH_2NHCH_3$; and (c) $R^5$ is OH, $CH_2OH$, carbocyclic, or an optionally substituted phenyl or pyridyl ring, and Q' is —C(O)NH—.

6. The compound according to claim 1, wherein said compound is of formula I":

I"

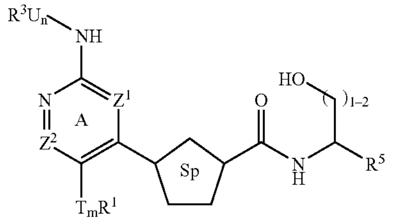

or a pharmaceutically acceptable salt thereof.

7. The compound according to claim 6, wherein said compound has one or more features selected from the group consisting of:

(a) $R^3$ is hydrogen, carbocyclyl, —CH($R^8$)R, or an optionally substituted group selected from $C_{1-4}$ aliphatic, 3–6 membered heterocyclic, or a 5–6 membered aryl or heteroaryl ring;

(b) $T_mR^1$ is hydrogen, $N(R^4)_2$, OH, 3–6 membered carbocyclyl, or an optionally substituted group selected from $C_{1-6}$ aliphatic or a 5–6 membered aryl or heteroaryl ring; and (c) $R^5$ is an optionally substituted 6-membered aryl, heteroaryl, or carbocyclic ring.

8. The compound according to claim 7, wherein:

(a) $R^3$ is hydrogen, carbocyclyl, —CH($R^8$)R, or an optionally substituted group selected from $C_{1-4}$ aliphatic, 3–6 membered heterocyclic, or a 5–6 membered aryl or heteroaryl ring;

(b) $T_mR^1$ is hydrogen, $N(R^4)_2$, OH, 3–6 membered carbocyclyl, or an optionally substituted group selected from $C_{1-6}$ aliphatic or a 5–6 membered aryl or heteroaryl ring; and (c) $R^5$ is an optionally substituted 6-membered aryl, heteroaryl, or carbocyclic ring.

9. The compound according to claim 1, wherein said compound is of formula I°:

I°

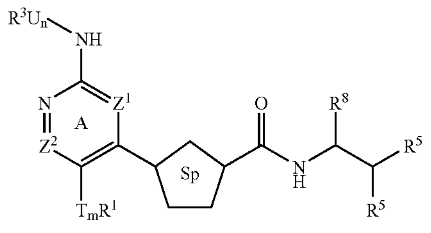

or a pharmaceutically acceptable salt thereof.

10. The compound according to claim 9, wherein said compound has one or more features selected from the group consisting of:

(a) $R^3$ is hydrogen, carbocyclyl, —CH($R^8$)R, or an optionally substituted group selected from $C_{1-4}$ aliphatic, 3–6 membered heterocyclic, or a 5–6 membered aryl or heteroaryl ring;

(b) $T_mR^1$ is hydrogen, amino, OH, 3–6 membered carbocyclyl, or an optionally substituted group selected from $C_{1-6}$ aliphatic or a 5–6 membered aryl or heteroaryl ring; and (c) $R^5$ is R or $OR^7$, wherein R is carbocyclic, or an optionally substituted 5 or 6-membered aryl or heteroaryl ring.

11. The compound according to claim 10, wherein:

(a) $R^3$ is hydrogen, carbocyclyl, —CH($R^8$)R, or an optionally substituted group selected from $C_{1-4}$ aliphatic, 3–6 membered heterocyclic, or a 5–6 membered aryl or heteroaryl ring;

(b) $T_mR^1$ is hydrogen, amino, OH, 3–6 membered carbocyclyl, or an optionally substituted group selected from $C_{1-6}$ aliphatic or a 5–6 membered aryl or heteroaryl ring; and (c) $R^5$ is R or $OR^7$, wherein R is carbocyclic, or an optionally substituted 5 or 6-membered aryl or heteroaryl ring.

12. A composition comprising an effective amount of a compound according to any of claims 1 or 2–11 and a pharmaceutically acceptable carrier.

13. The composition according to claim 12, further comprising an additional therapeutic agent selected from a chemotherapeutic agent or anti-proliferative agent, or an agents for treating diabetes, an anti-inflammatory agent, an immunomodulatory or immunosuppressive agent, an agent for treating neurlogical disorders, an agent for treating cardiovascular disease, an agent for treating liver disease, cholestyramine, an interferon, an anti-viral agents, an agents for treating blood disorders, or an agent for treating immunodeficiency disorders.

14. A method of treating a disease in a patient, wherein the disease is a cancer selected from melanoma, colon cancer, breast cancer, lung cancer, kidney carcinoma, ovarian cancer, pancreatic cancer, or prostate cancer comprising the step of administering to said patient a composition according to claim 12.

15. A method of treating a cardiovascular disease in a patient comprising the step of administering to said patient a composition according to claim 12, wherein said cardiovascular disease is selected from stroke, restenosis, cardiomegaly, atherosclerosis, myocardial infarction, or congestive heart failure.

16. A method of treating a disease in a patient in need thereof, wherein said disease is diabetes, comprising the step of administering to said patient a composition according to claim 12.

17. A method of treating a disease in a patient in need thereof, wherein said disease is Alzheimer's disease, comprising the step of administering to said patient a composition according to claim 12.

18. A method of treating a disease in a patient in need thereof, wherein said disease is schizophrenia, comprising the step of administering to said patient a composition according to claim 12.

19. A method of treating a cancer selected from melanoma, colon cancer, breast cancer, lung cancer, kidney carcinoma, ovarian cancer, pancreatic cancer, or prostate cancer, which method comprises administering to said patient a compound of formula I:

I

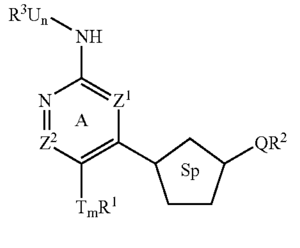

or a pharmaceutically acceptable salt thereof, wherein:

Sp is a 5-membered heteroaromatic ring, selected from pyrrole, imidazole, pyrazole, triazole, oxazole, isoxazole, 1,3-thiazole, 1,2-thiazole, or furan, wherein Ring A and $QR^2$ are attached to Sp at non-adjacent positions; and wherein Sp has up to two $R^6$ substituents, provided that two substitutable carbon ring atoms in Sp are not simultaneously substituted by $R^6$;

$Z^1$ is CH and $Z^2$ is CH;

T is a linker group selected from —NH—, —$CH_2$—, —CO—, or a saturated or unsaturated $C_{1-6}$ alkylidene chain which is optionally substituted, and wherein up to two saturated carbons of the chain are optionally replaced by —C(O)—, —C(O)C(O)—, —$CONR^7$—, —$CONR^7NR^7$—, —$CO_2$—, —OC(O)—, —$NR^7CO_2$—, —O—, —$NR^7CONR^7$—, —OC(O)$NR^7$—, —$NR^7NR^7$—, —$NR^7CO$—, —S—, —SO—, —$SO_2$—, —$NR^7$—, —$SO_2NR^7$—, or —$NR^7SO_2$—;

Q is —$CO_2$—, —C(O)$NR^7$—, or —$S(O)_2NR^7$—;

U is selected from —$NR^7$—, —$NR^7CO$—, —$NR^7CONR^7$—, —$NR^7CO_2$—, —O—, —$CONR^7$—, —CO—, —$CO_2$—, —OC(O)—, —$NR^7SO_2$—, —$SO_2NR^7$—, —$NR^7SO_2NR^7$—, or —$SO_2$—;

m and n are each independently selected from zero or one;

$R^1$ is selected from hydrogen, CN, halogen, R, $N(R^7)_2$, OR, or OH;

$R^2$ is selected from —$(CH_2)_yR^5$, —$(CH_2)_yCH(R^5)_2$, —$(CH_2)_yCH(R^8)CH(R^5)_2$, —$N(R^4)_2$, or —$NR^4(CH_2)_yN(R^4)_2$;

y is 0–6;

$R^3$ is selected from $R^7$, R, —$(CH_2)_yCH(R^8)R$, CN, —$(CH_2)_yCH(R^8)CH(R^5)_2$, or —$(CH_2)_yCH(R^8)N(R^4)_2$;

each R is independently selected from an optionally substituted group selected from $C_{1-6}$ aliphatic, $C_{6-10}$ aryl, a heteroaryl ring having 5–10 ring atoms, or a heterocyclyl ring having 3–10 ring atoms;

each $R^4$ is independently selected from R, $R^7$, —$COR^7$, —$CO_2R$, —$CON(R^7)_2$, —$SO_2R^7$, —$(CH_2)_yR^5$, or —$(CH_2)_yCH(R^5)_2$;

each $R^5$ is independently selected from R, OR, $CO_2R$, $(CH_2)_yN(R^7)_2$, $N(R^7)_2$, $OR^7$, $SR^7$, $NR^7COR^7$, $NR^7CON(R^7)_2$, $CON(R^7)_2$, $SO_2R^7$, $NR^7SO_2R^7$, $COR^7$, CN, or $SO_2N(R^7)_2$;

each $R^6$ is independently selected from $R^7$, F, Cl, $OR^7$, $SR^7$, $NR^7COR^7$, $NR^7CON(R^7)_2$, $CON(R^7)_2$, $SO_2R^7$, $NR^7SO_2R^7$, $COR^7$, CN, or $SO_2N(R^7)_2$;

each $R^7$ is independently selected from hydrogen or an optionally substituted $C_{1-6}$ aliphatic group, or two $R^7$ on the same nitrogen are taken together with the nitrogen to form a 5–8 membered heterocyclyl or heteroaryl ring;

$R^8$ is selected from R, $(CH_2)_wOR^7$, $(CH_2)_wN(R^4)_2$, or $(CH_2)_wSR^7$; and each w is independently selected from 0–4.

20. The method according to claim 19, wherein said compound has one or more features selected from the group consisting of:

(a) $R^3$ is hydrogen, carbocyclyl, —$CH(R^8)R$, or an optionally substituted group selected from $C_{1-4}$ aliphatic, 3–6 membered heterocyclic, or a 5–6 membered aryl or heteroaryl ring;

(b) $T_mR^1$ is hydrogen, amino, OH, 3–6 membered carbocyclyl, or an optionally substituted group selected from $C_{1-6}$ aliphatic or a 5–6 membered aryl or heteroaryl ring;

(c) Q is, —$CO_2$—, —CONH—, or; —$SO_2NH$—;

(d) $R^2$ is —$NR^4(CH_2)_yN(R^4)_2$, —$(CH_2)_yR^5$, —$(CH_2)_yCH(R^5)_2$, or —$(CH_2)_yCH(R^8)CH(R^5)_2$;

(f) $R^4$ is R, $R^7$, or —$(CH_2)_yCH(R^5)_2$; and (g) $R^5$ is an optionally substituted group selected from $C_{1-6}$ aliphatic, phenyl, 5–6 membered heteroaryl, or 5–6 membered heterocyclyl.

21. The method according to claim 20, wherein:

(a) $R^3$ is hydrogen, carbocyclyl, —$CH(R^8)R$, or an optionally substituted group selected from $C_{1-4}$ aliphatic, 3–6 membered heterocyclic, or a 5–6 membered aryl or heteroaryl ring;

(b) $T_mR^1$ is hydrogen, amino, OH, 3–6 membered carbocyclyl, or an optionally substituted group selected from $C_{1-6}$ aliphatic or a 5–6 membered aryl or heteroaryl ring;

(c) Q is —$CO_2$—, —CONH—, —$SO_2NH$—, or —$SO_2NH$—;

(d) $R^2$ is —$NR^4(CH_2)_yN(R^4)_2$, —$(CH_2)_yR^5$, —$(CH_2)_yCH(R^5)_2$, or —$(CH_2)_yCH(R^8)CH(R^5)_2$;

(f) $R^4$ is R, $R^7$, or —$(CH_2)_yCH(R^5)_2$; and (g) $R^5$ is an optionally substituted group selected from $C_{1-6}$ aliphatic, phenyl, 5–6 membered heteroaryl, or 5–6 membered heterocyclyl.

22. The method according to claim 20, wherein said compound has one or more features selected from the group consisting of:

(a) $R^3$ is selected from hydrogen, methyl, ethyl, propyl, cyclopropyl, cyclohexyl, isopropyl, —$CH(CH_2OH)$phenyl, —$CH(CH_2OH)$ethyl, —$CH(CH_2OH)_2$, —$CH(CH_2OH)$isopropyl, —$CH(CH_2OH)CH_2$cyclopropyl, or an optionally substituted phenyl, benzyl, or isoxazolyl group;

(b) $T_mR^1$ is selected from optionally substituted phenyl, methyl, ethyl, propyl, cyclopropyl, cyclohexyl, $CH_2OCH_3$, $CH_2OH$, OH, $NH_2$, $NHCH_3$, NHAc, NHC(O)$NHCH_3$, or $CH_2NHCH_3$;

(c) Q is —CONH—, or —$SO_2NH$—;

(d) $R^2$ is —$(CH_2)_yR^5$, —$(CH_2)_yCH(R^5)_2$, or —$(CH_2)_yCH(R^8)CH(R^5)_2$, wherein $R^8$ is OH or $CH_2OH$; and (e) $R^5$ is —$CH_2OH$, —$(CH_2)_2OH$, isopropyl, or an optionally substituted group selected from pyrrolidin-1-yl, morpholin-4-yl, piperidin-1-yl, piperazin-1-yl, 4-methyl[1,4]diazepan-1-yl, 4-phenyl-piperazine1-yl, pyridin-3-yl, pyridin-4-yl, imidazolyl, furan-2-yl, 1,2,3,4-tetrahydroisoquinoline, tetrahydrofuran-2-yl, cyclohexyl, phenyl, or benzyl.

23. The method according to claim 22, wherein:

(a) $R^3$ is selected from hydrogen, methyl, ethyl, propyl, cyclopropyl, cyclohexyl, isopropyl, —$CH(CH_2OH)$phenyl, —$CH(CH_2OH)$ethyl, —$CH(CH_2OH)_2$, —$CH(CH_2OH)$isopropyl, —$CH(CH_2OH)CH_2$cyclopropyl, or an optionally substituted phenyl, benzyl, or isoxazolyl group;

(b) $T_mR^1$ is selected from optionally substituted phenyl, methyl, ethyl, propyl, cyclopropyl, cyclohexyl, $CH_2OCH_3$, $CH_2OH$, OH, $NH_2$, $NHCH_3$, NHAc, $NHC(O)NHCH_3$, or $CH_2NHCH_3$;

(c) Q is —CONH—, or —$SO_2NH$—;

(d) $R^2$ is —$(CH_2)_yR^5$, —$(CH_2)_yCH(R^5)_2$, or —$(CH_2)_yCH(R^8)CH(R^5)_2$, wherein $R^8$ is OH or $CH_2OH$; and (e) $R^5$ is —$CH_2OH$, —$(CH_2)_2OH$, isopropyl, or an optionally substituted group selected from pyrrolidin-1-yl, morpholin-4-yl, piperidin-1-yl, piperazin-1-yl, 4-methyl[1,4]diazepan-1-yl, 4-phenyl-piperazine-1-yl, pyridin-3-yl, pyridin-4-yl, imidazolyl, furan-2-yl, 1,2,3,4-tetrahydroisoquinoline, tetrahydrofuran-2-yl, cyclohexyl, phenyl, or benzyl.

24. A composition for coating an implantable device comprising a compound according to claim 1 and a carrier suitable for coating said implantable device.

25. An implantable device coated with a composition according to claim 24.

* * * * *